United States Patent [19]

Evers et al.

[11] Patent Number: 4,749,681

[45] Date of Patent: Jun. 7, 1988

[54] POLYALKYL-SUBSTITUTED OXOCYCLOHEPTANE DERIVATIVES, ORGANOLEPTIC USES THEREOF AND PROCESSES FOR PREPARING SAME

[75] Inventors: William J. Evers, Locust; Howard H. Heinsohn, Jr., Freehold, both of N.J.

[73] Assignee: International Flavors & Fragrances Inc., New York, N.Y.

[21] Appl. No.: 53,393

[22] Filed: May 22, 1986

[51] Int. Cl.$^4$ .............................................. A61K 7/46
[52] U.S. Cl. ..................................... 512/8; 568/375; 568/821; 252/174.11; 523/102
[58] Field of Search .................... 512/8; 568/375, 821; 252/174.11; 523/107

[56] References Cited

U.S. PATENT DOCUMENTS 3,869,411  3/1975  Hall et al. ............................ 252/522
4,057,556  11/1977  Bagli et al. ........................... 568/375

OTHER PUBLICATIONS

No. 193008, 9/3/86, Chem. Abstrs., vol. 105, No. 225873y, Matsumoto, et al.
Pinder, "The Chemistry of the Terpenes", published by John Wiley & Sons Inc., 1960, pp. 72 and 73 (title page, data page and pp. 72 and 73 attached).
Hall and Lala, "Cyclization of Dimethyl-1,6-Octadienes", J. Org. Chem., vol. 37, No. 6, 1972, pp. 920 and 921.
Chem. Abstracts, vol. 105, No. 227080m (Miyawaki, et al.).
Abstract of Japanese Published Application J61/218543 (Taiyo Koryo KK) published on Sep. 29, 1986.

Primary Examiner—James H. Reamer
Attorney, Agent, or Firm—Arthur L. Liberman

[57] ABSTRACT

Described are polyalkyl-substituted oxocycloheptane derivatives defined according to the structure:

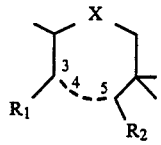

wherein X represents one of the moieties:

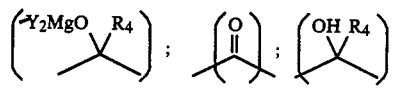

wherein one of the dashed lines is a carbon-carbon double bond and the other of the dashed lines is a carbon-carbon single bond; or both dashed lines are carbon-carbon single bonds; wherein $R_1$ and $R_2$ represents hydrogen or lower alkyl with the proviso that when the dashed line at the 4–5 position is a double bond, $R_2$ is hydrogen and when the dashed line at the 3–4 position is a double bond, $R_1$ is hydrogen; wherein $R_4$ represents $C_1$–$C_4$ lower alkyl; and wherein Y represents chloro or bromo.

Also described are the organoleptic uses of said polyalkyl-substituted oxocycloheptane derivatives in augmenting or enhancing the aroma of perfume compositions, colognes and perfumed articles including solid or liquid aninonic, cationic, nonionic or zwitterionic detergents, fabric softener articles, fabric softener compositions and perfumed polymers.

Also described are the processes for preparing said polyalkyl-substituted oxocycloheptane derivatives.

15 Claims, 45 Drawing Sheets

GLC PROFILE FOR EXAMPLE I.

NMR SPECTRUM FOR EXAMPLE I.

GLC PROFILE FOR EXAMPLE II.

NMR SPECTRUM FOR EXAMPLE II.

FIG. 8 NMR SPECTRUM FOR EXAMPLE III

GLC PROFILE FOR EXAMPLE IV.

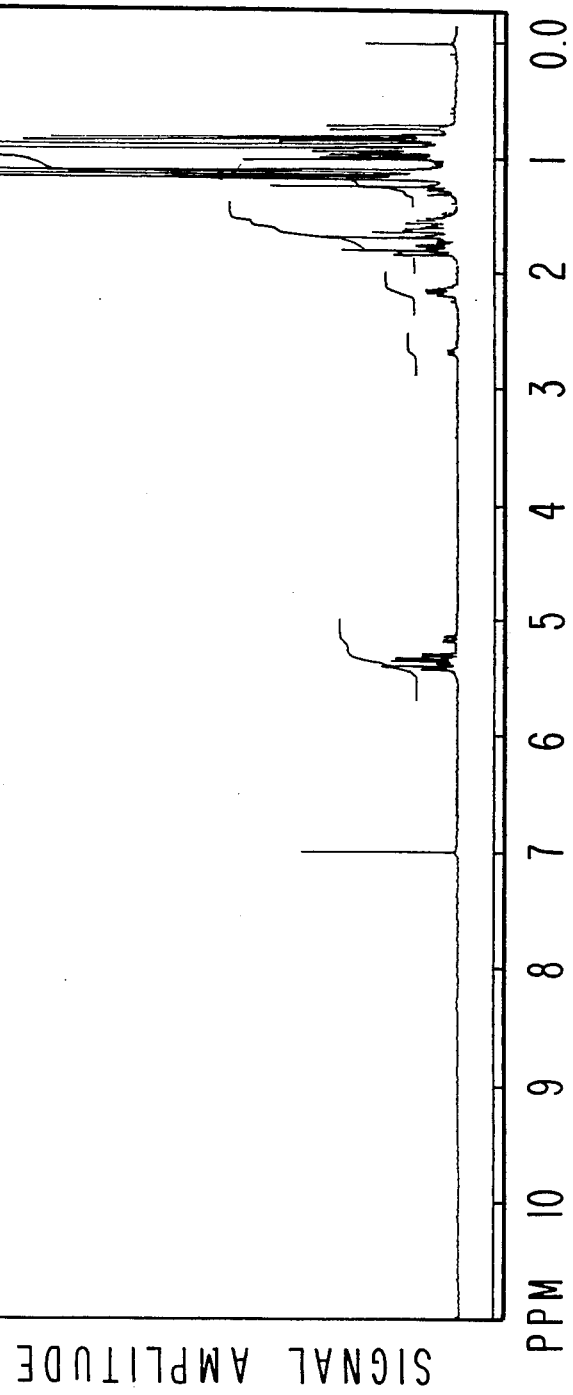
FIG. II-A
NMR SPECTRUM FOR EXAMPLE IV.

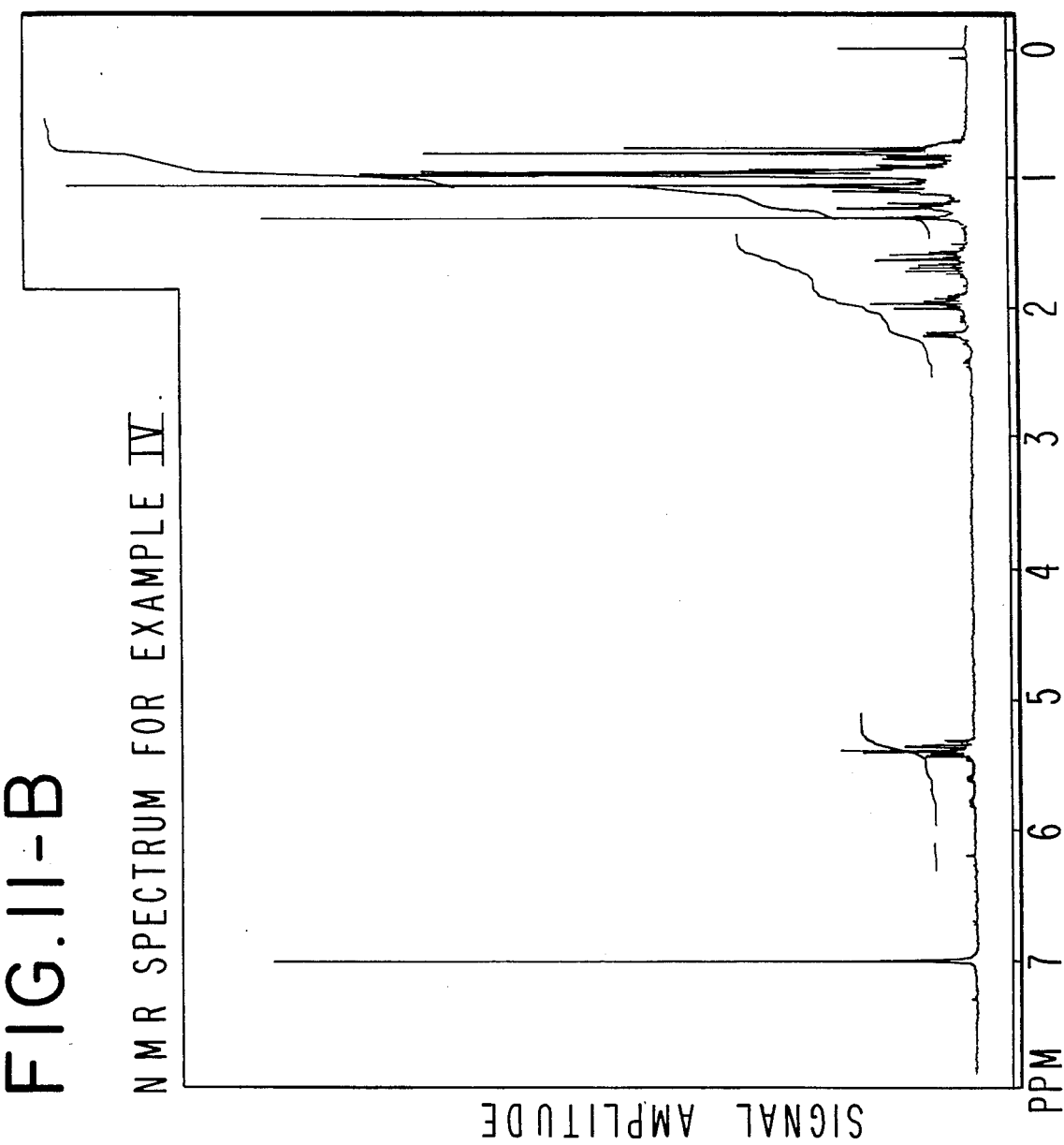
FIG.II-B NMR SPECTRUM FOR EXAMPLE IV.

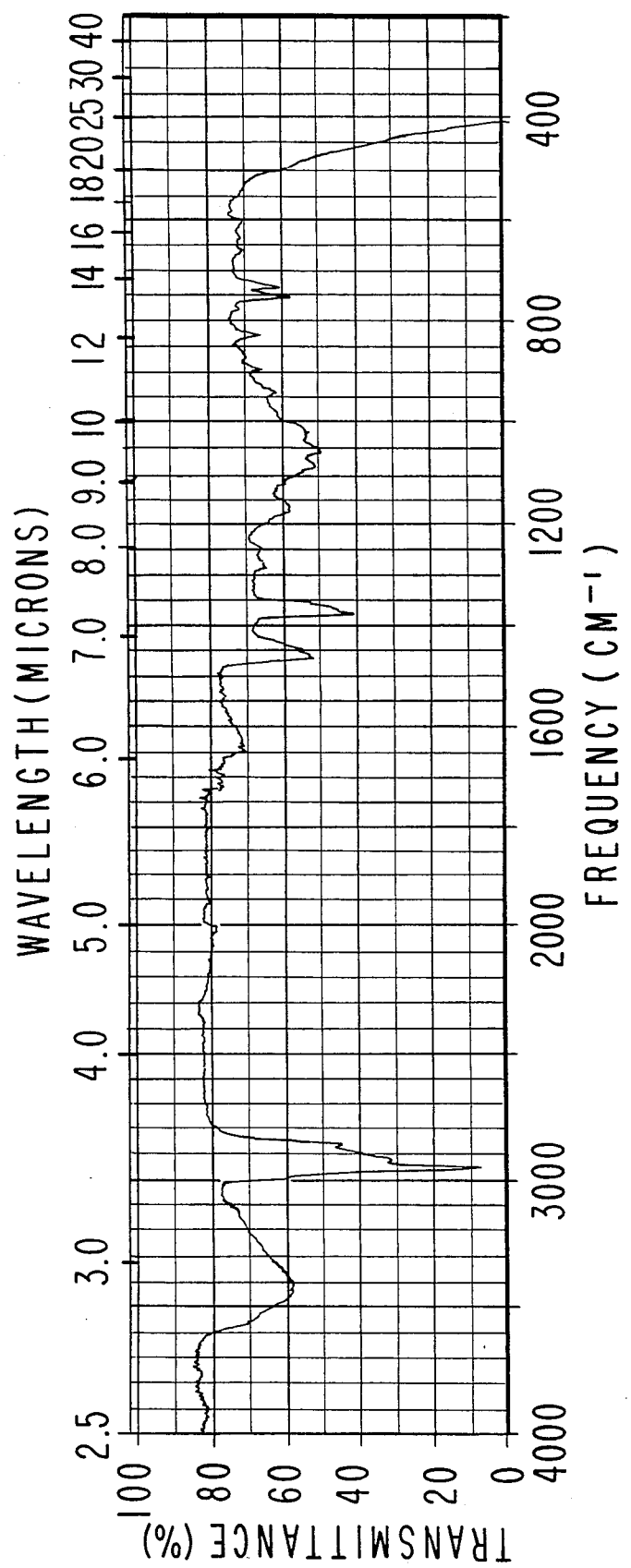
FIG.12-A
IR SPECTRUM FOR EXAMPLE IV.

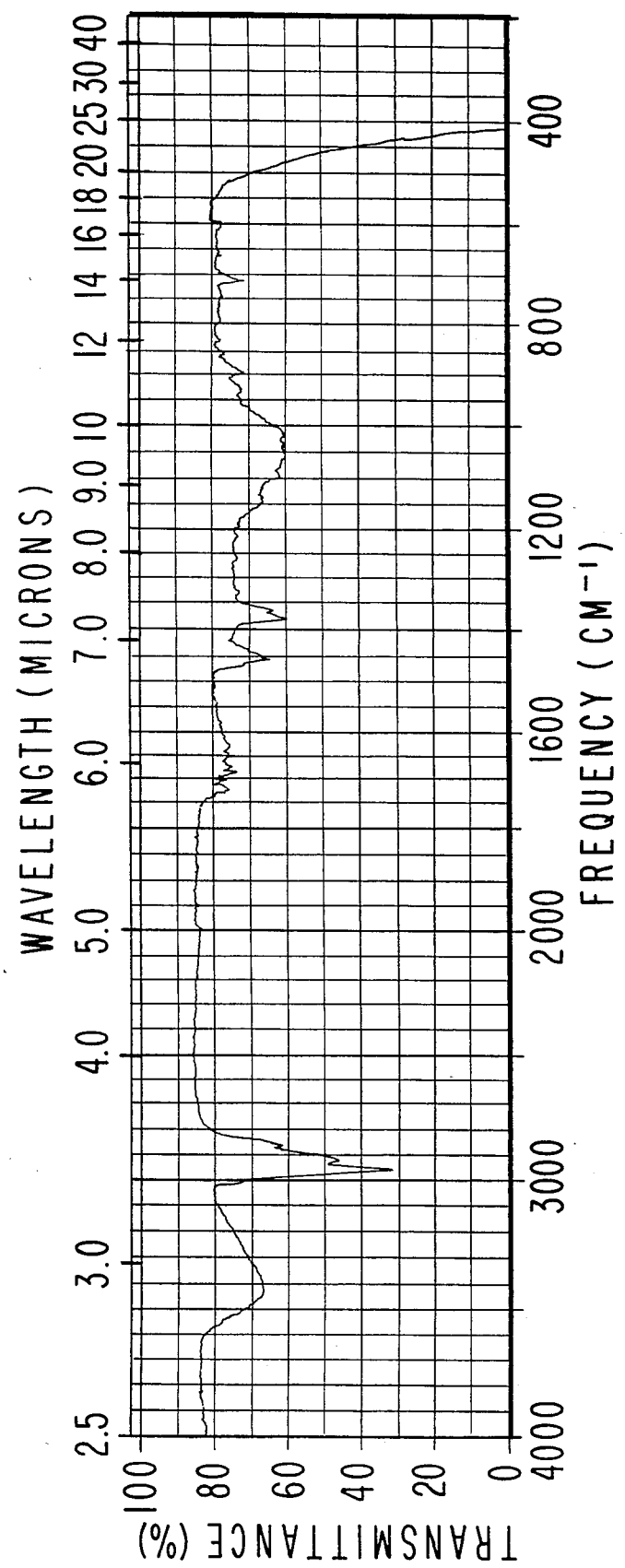

GLC PROFILE FOR EXAMPLE Ⅴ.

FIG. 14 NMR SPECTRUM FOR EXAMPLE V.

IR SPECTRUM FOR EXAMPLE V.

GLC PROFILE FOR EXAMPLE VI.

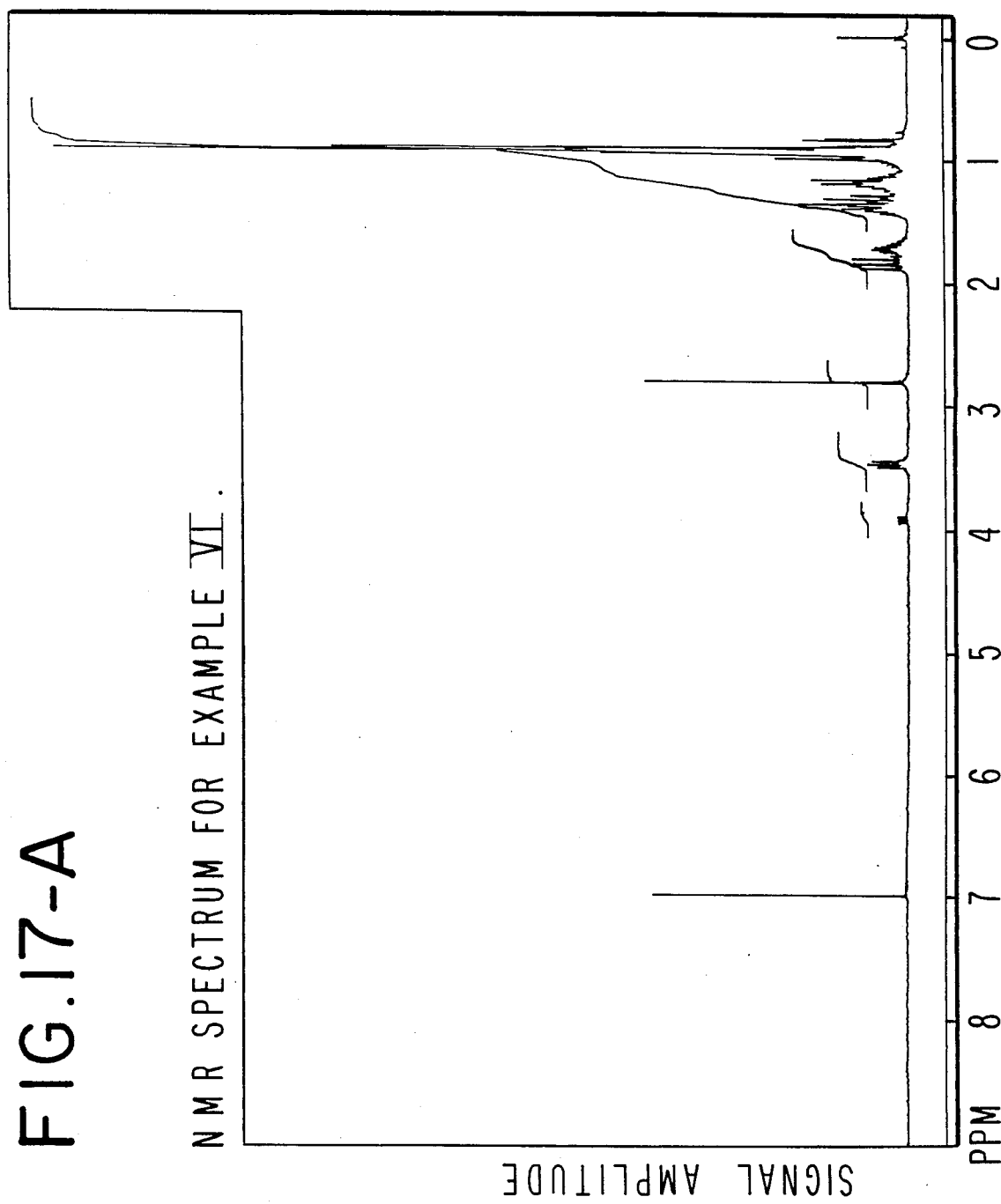
FIG. 17-A  NMR SPECTRUM FOR EXAMPLE VI.

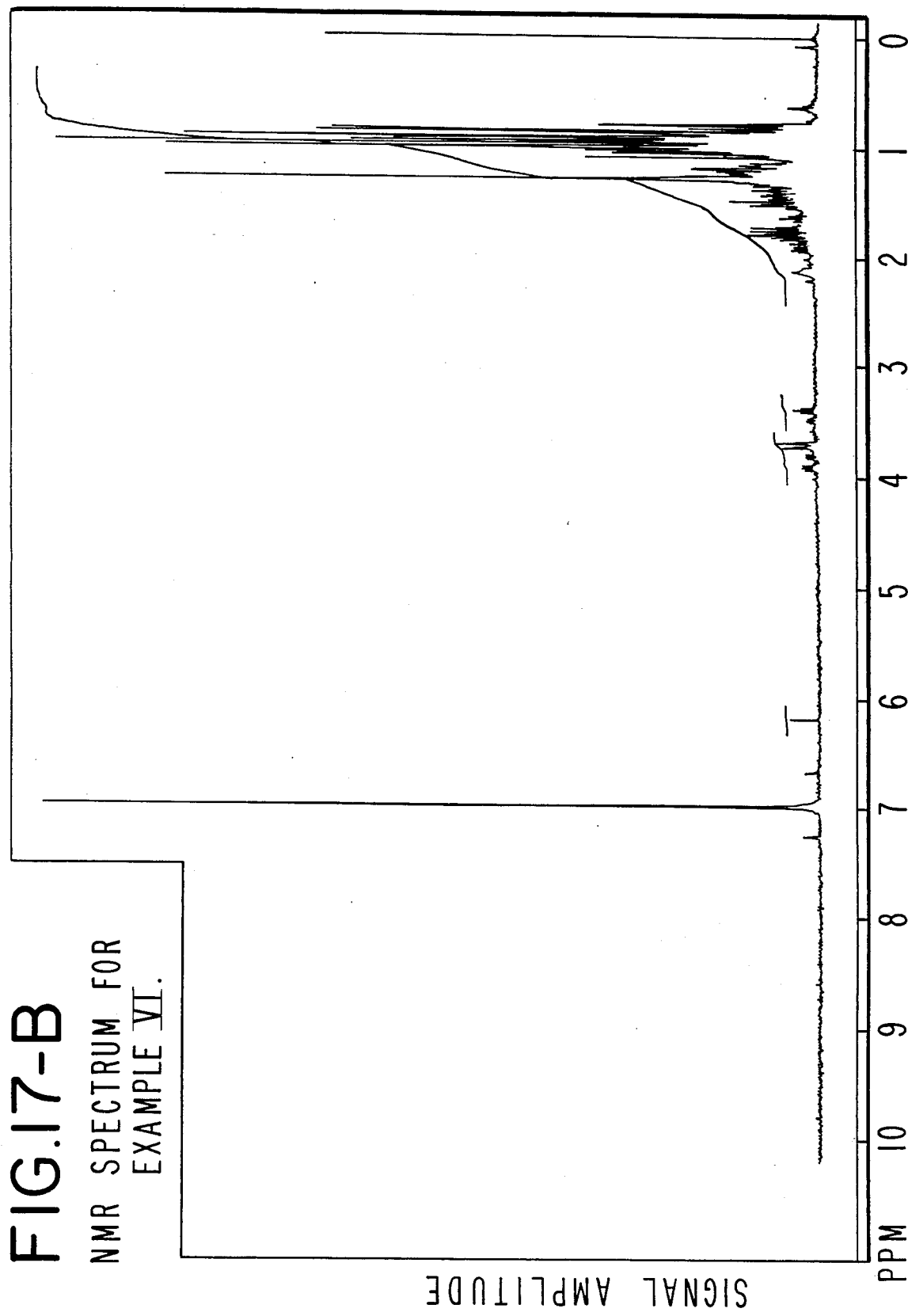

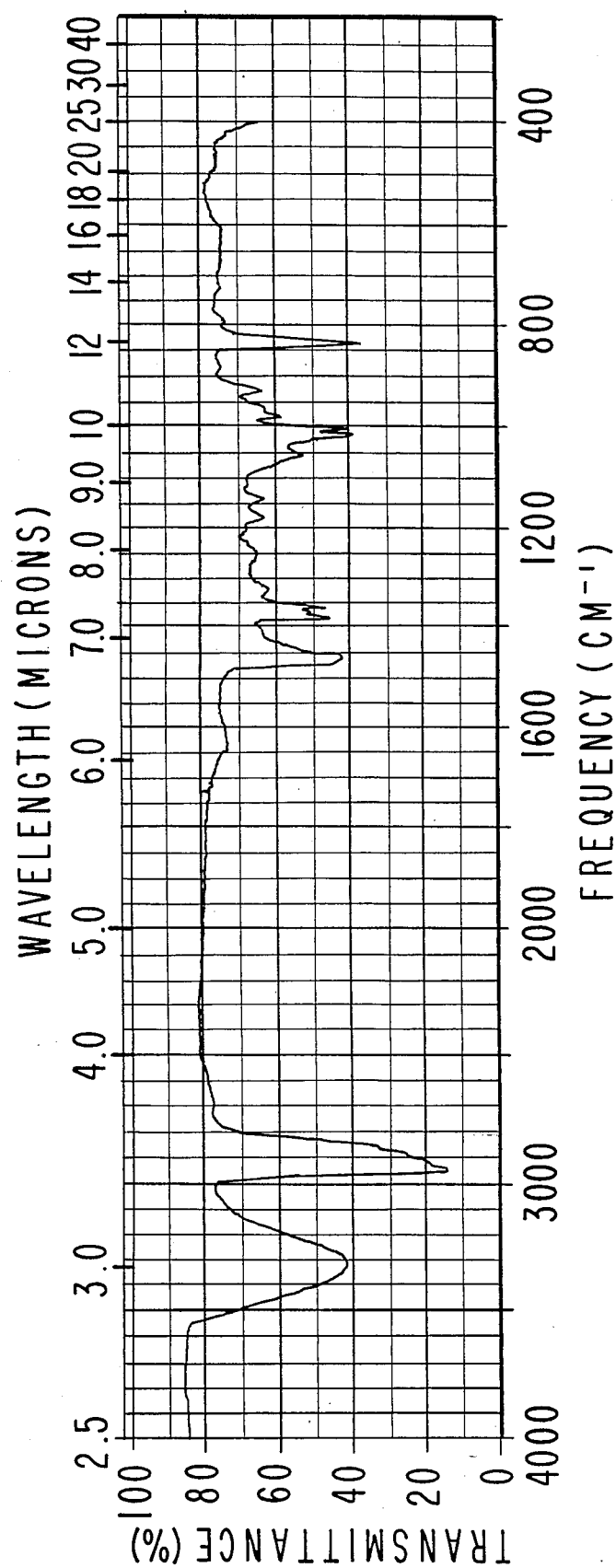

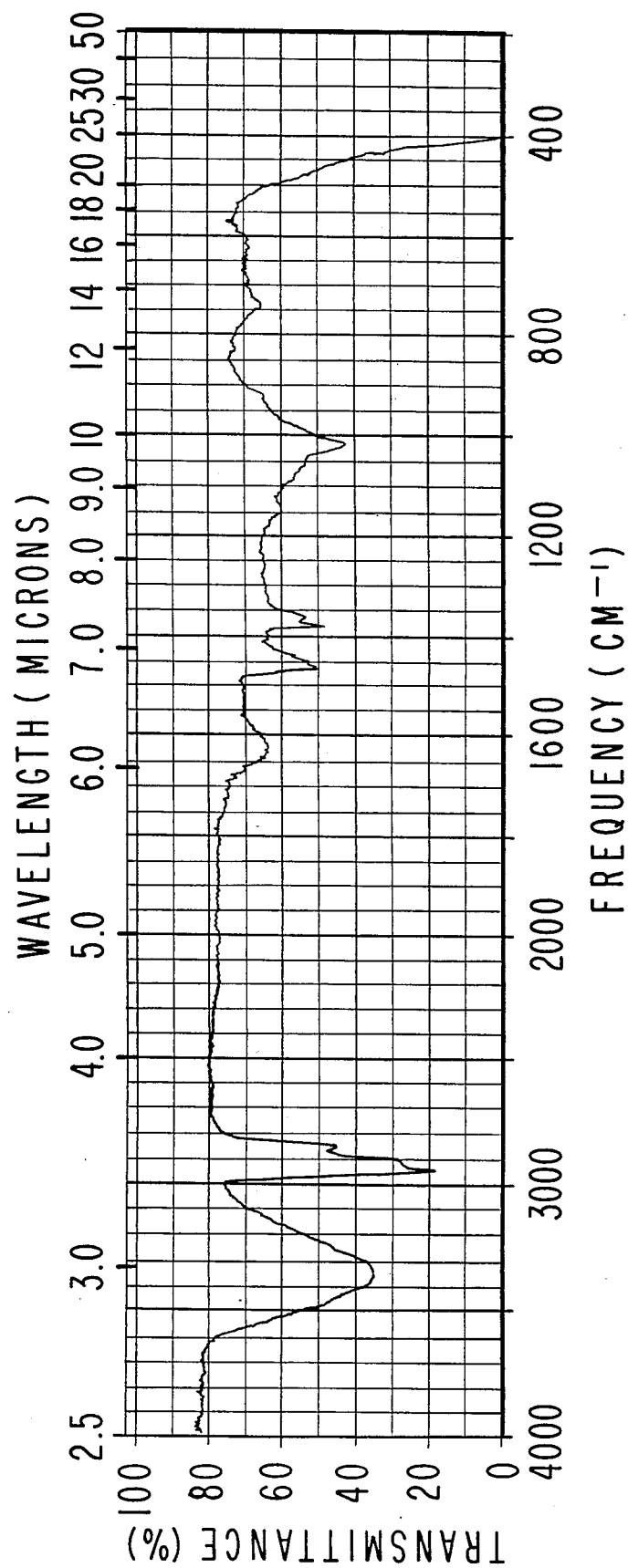
FIG.18-B
IR SPECTRUM FOR EXAMPLE VI.

GLC PROFILE FOR EXAMPLE VII.

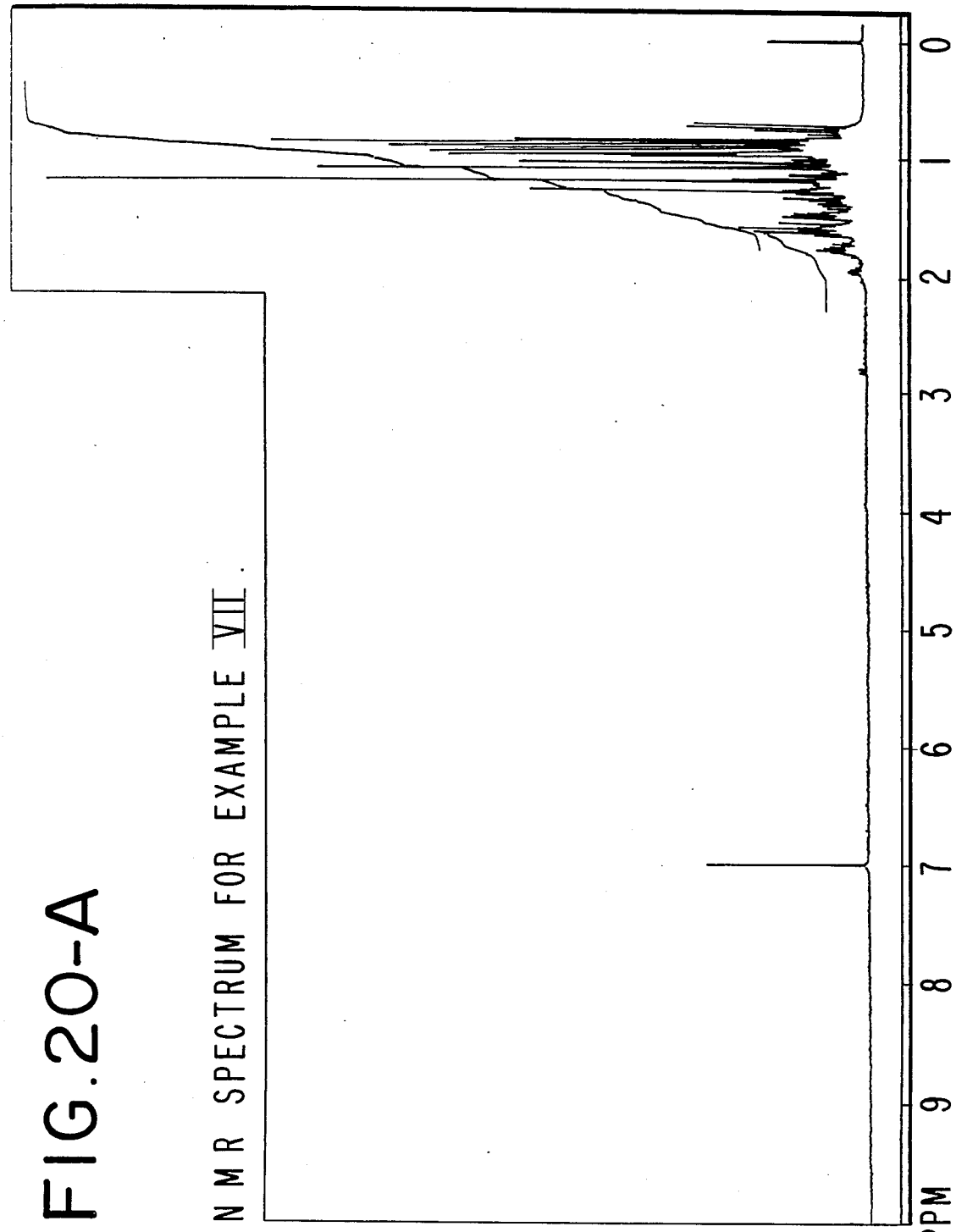
FIG.20-A NMR SPECTRUM FOR EXAMPLE VII

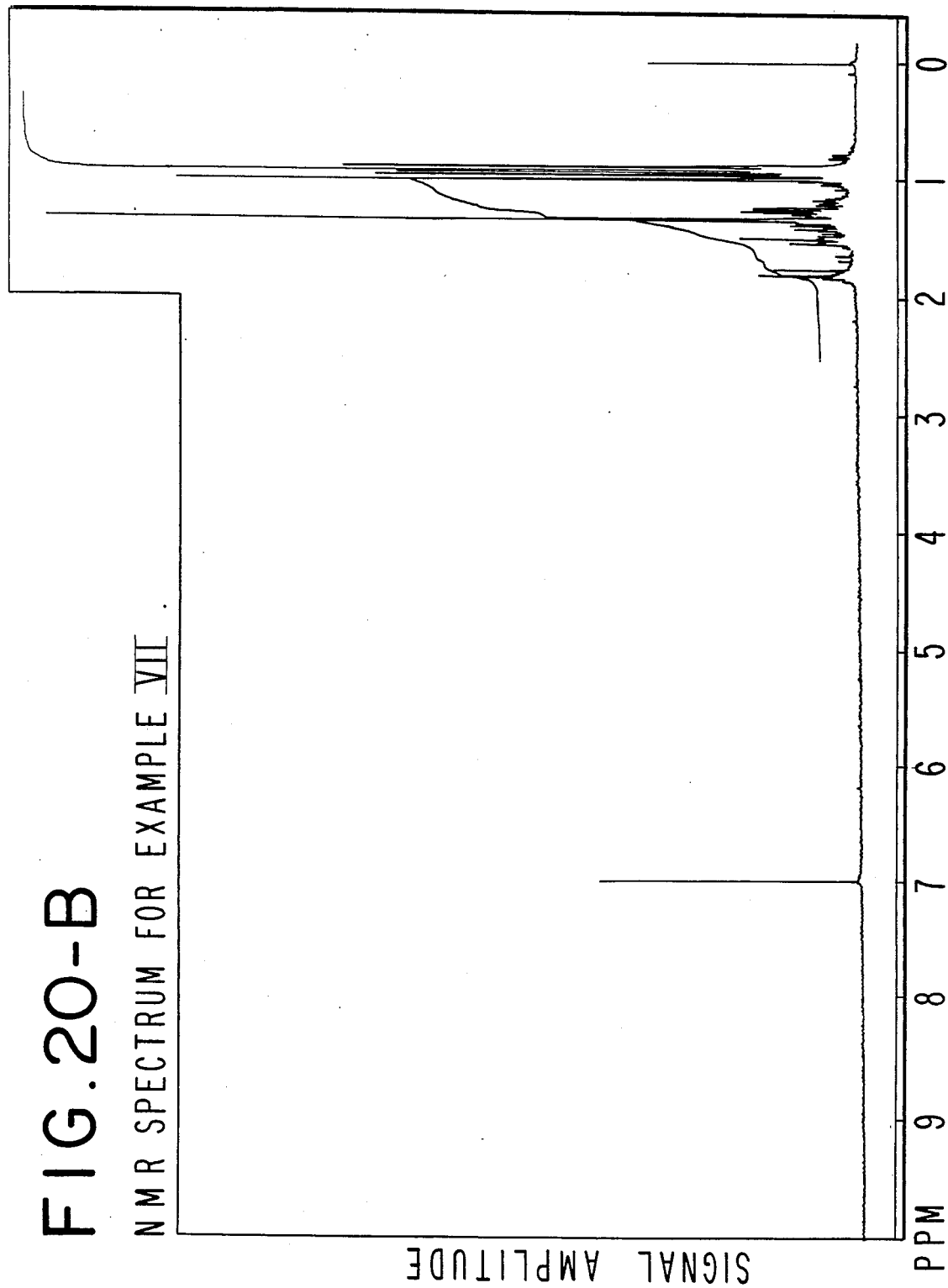
FIG. 20-B NMR SPECTRUM FOR EXAMPLE VII

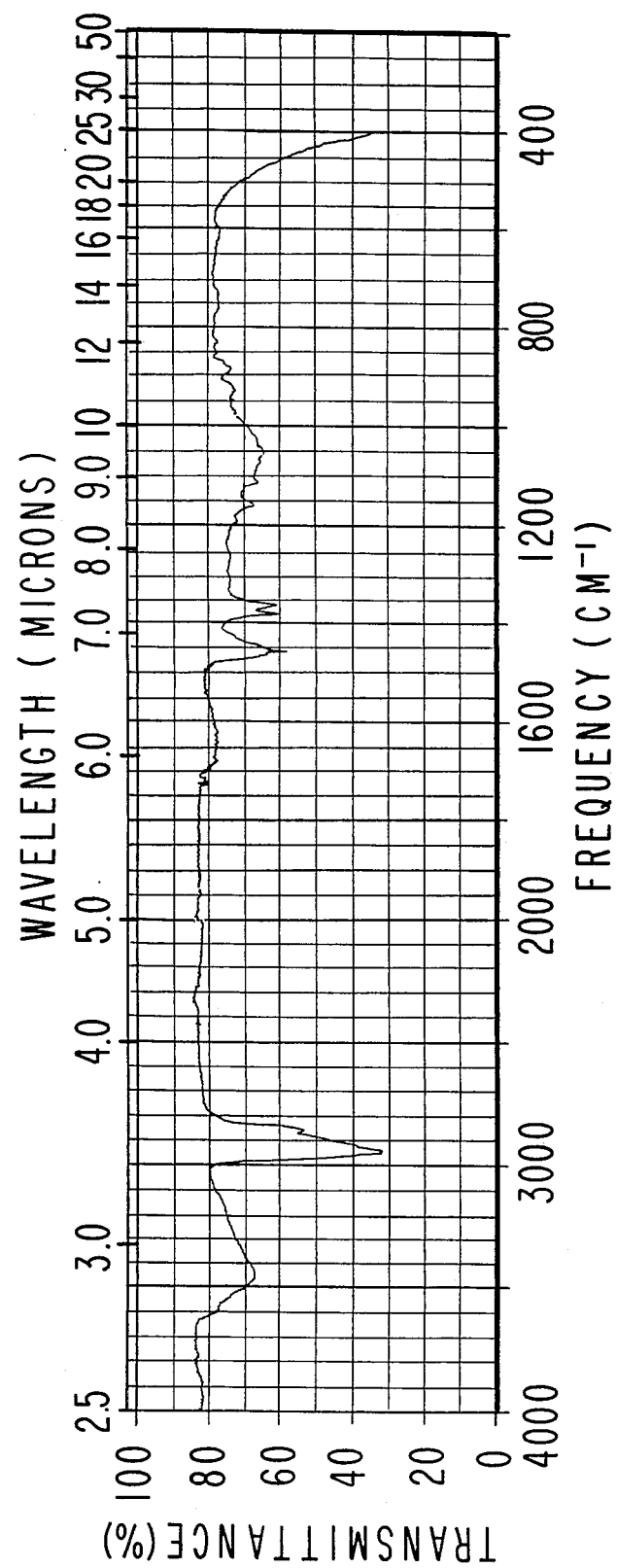

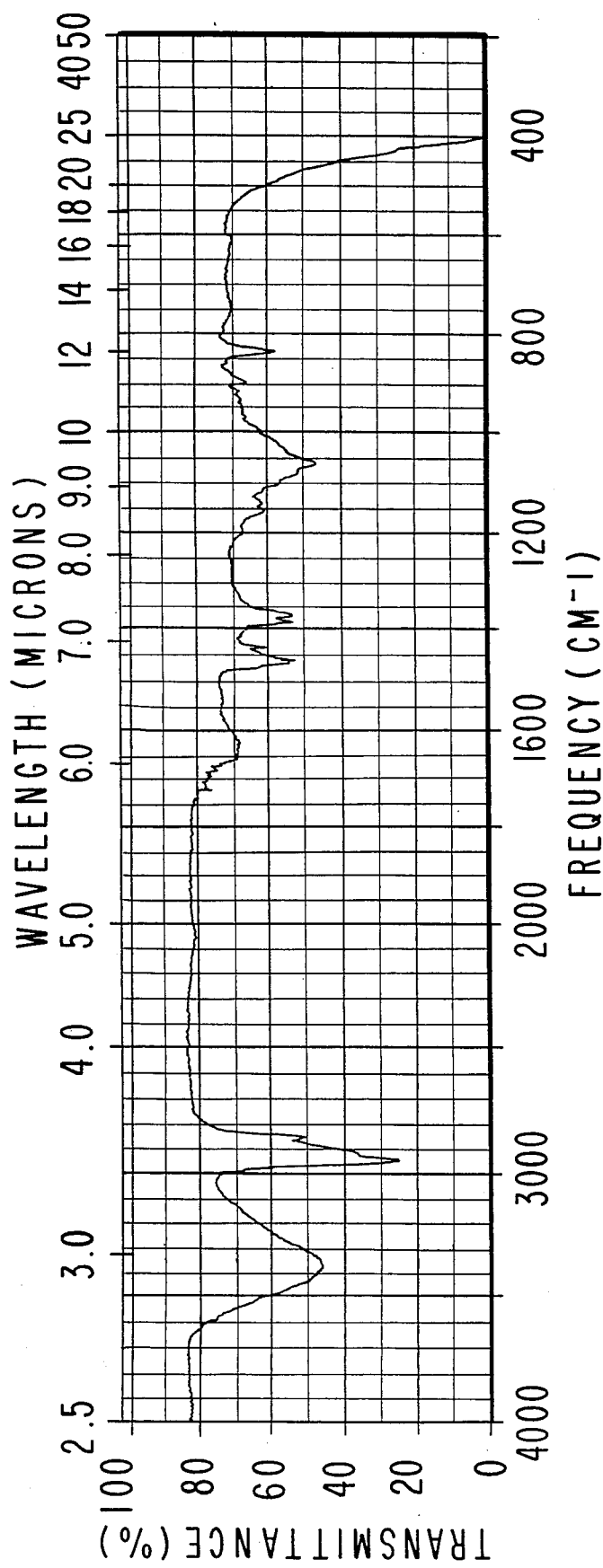

GLC PROFILE FOR EXAMPLE VIII.

FIG. 23 NMR SPECTRUM FOR EXAMPLE VIII.

GLC PROFILE FOR EXAMPLE IX.

FIG. 26 NMR SPECTRUM FOR EXAMPLE IX.

IR SPECTRUM FOR EXAMPLE IX.

GLC PROFILE FOR EXAMPLE X.

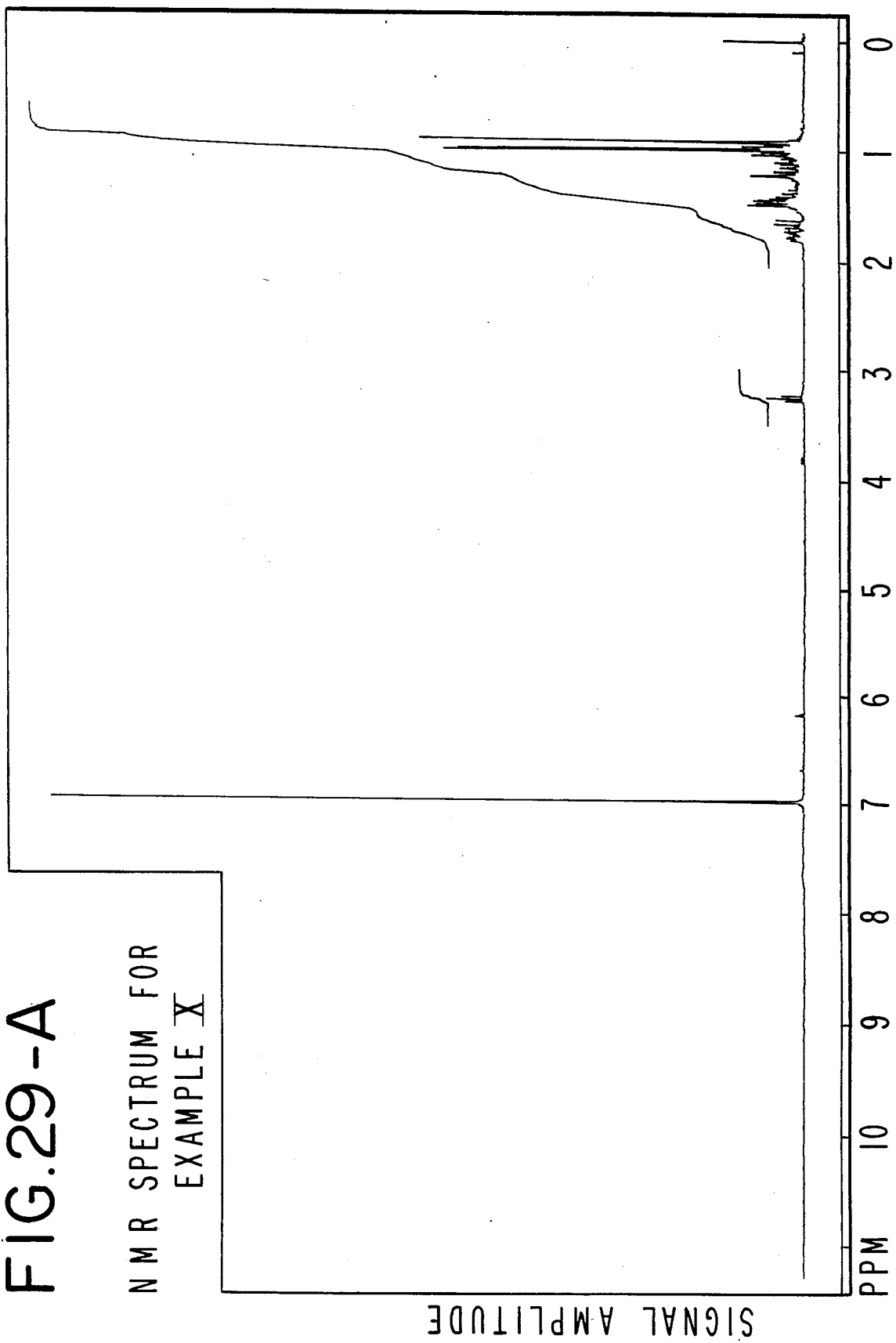
FIG.29-A NMR SPECTRUM FOR EXAMPLE X

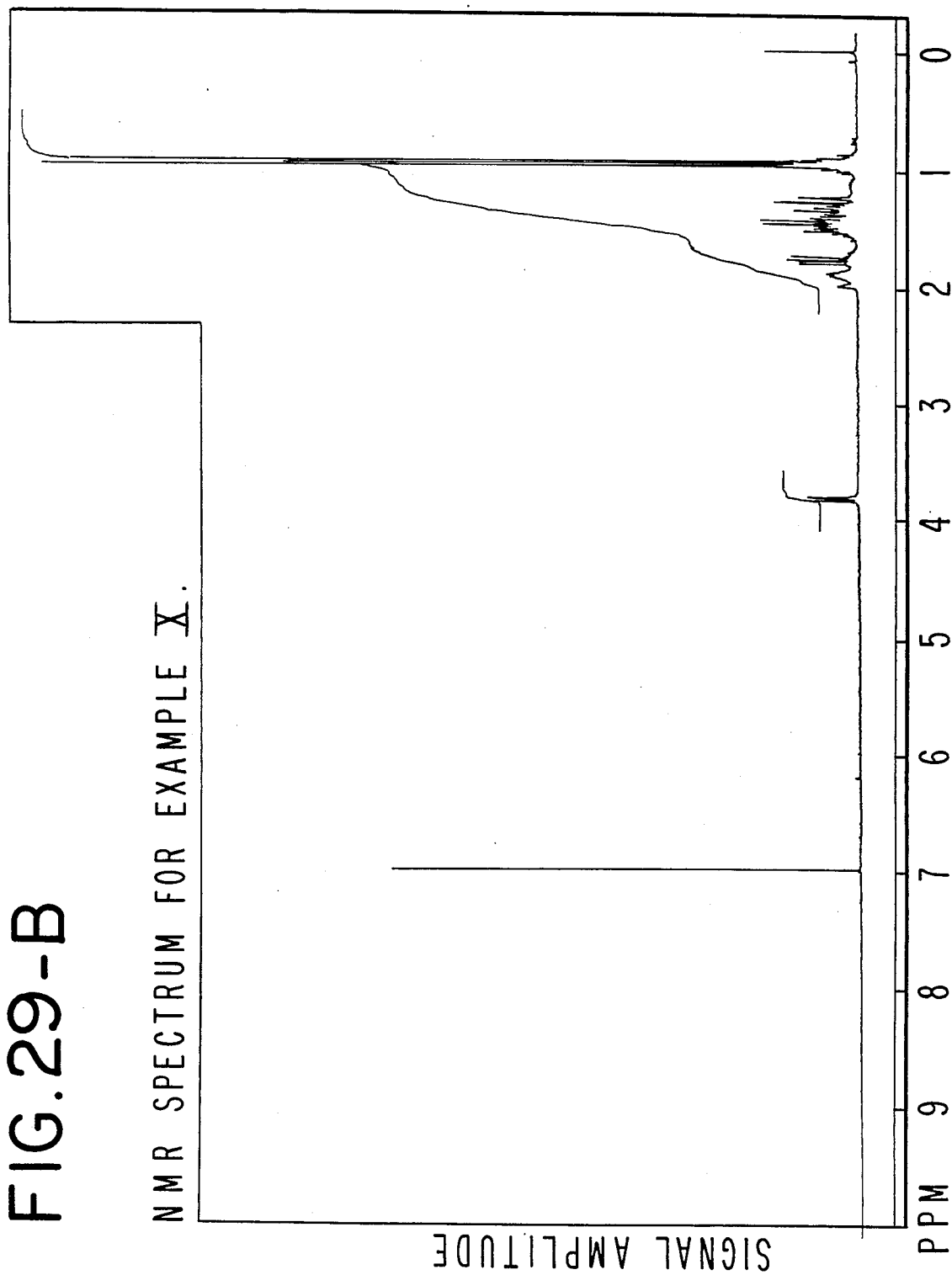
FIG. 29-B NMR SPECTRUM FOR EXAMPLE X.

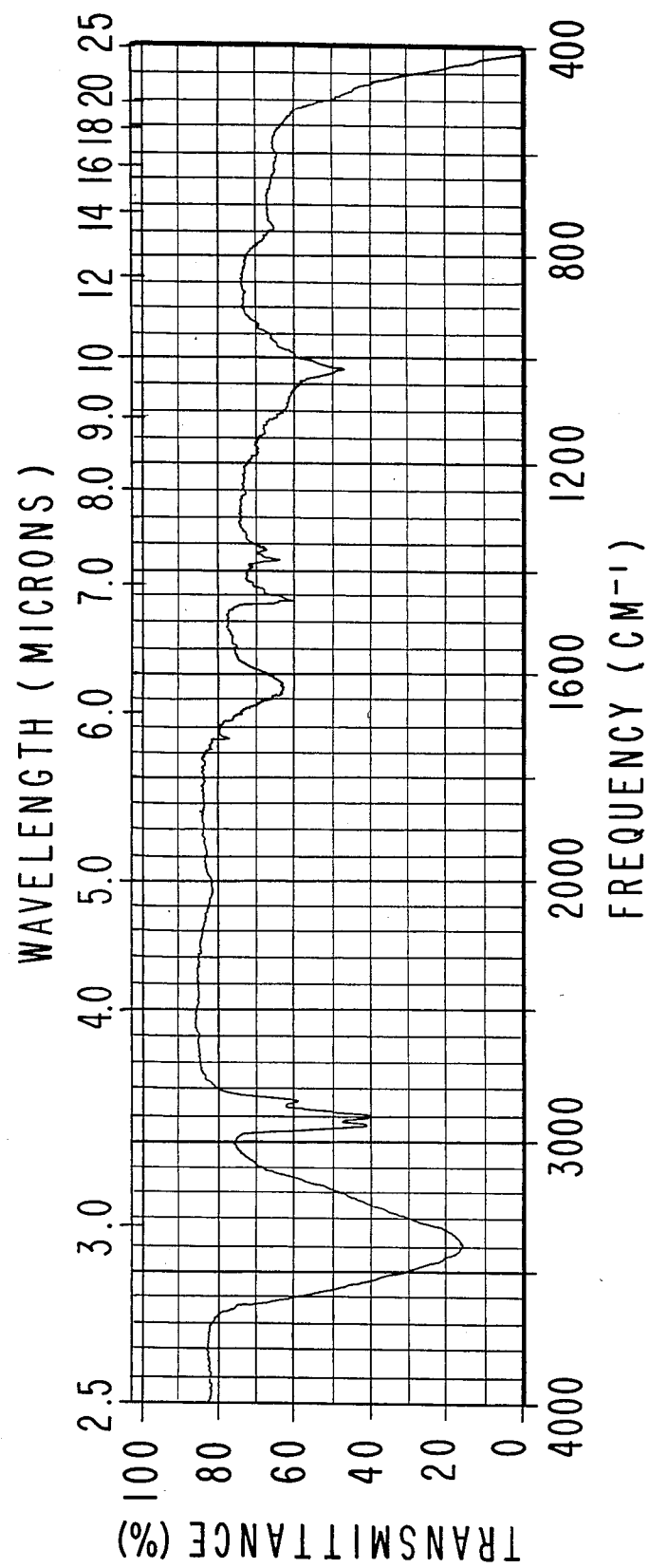

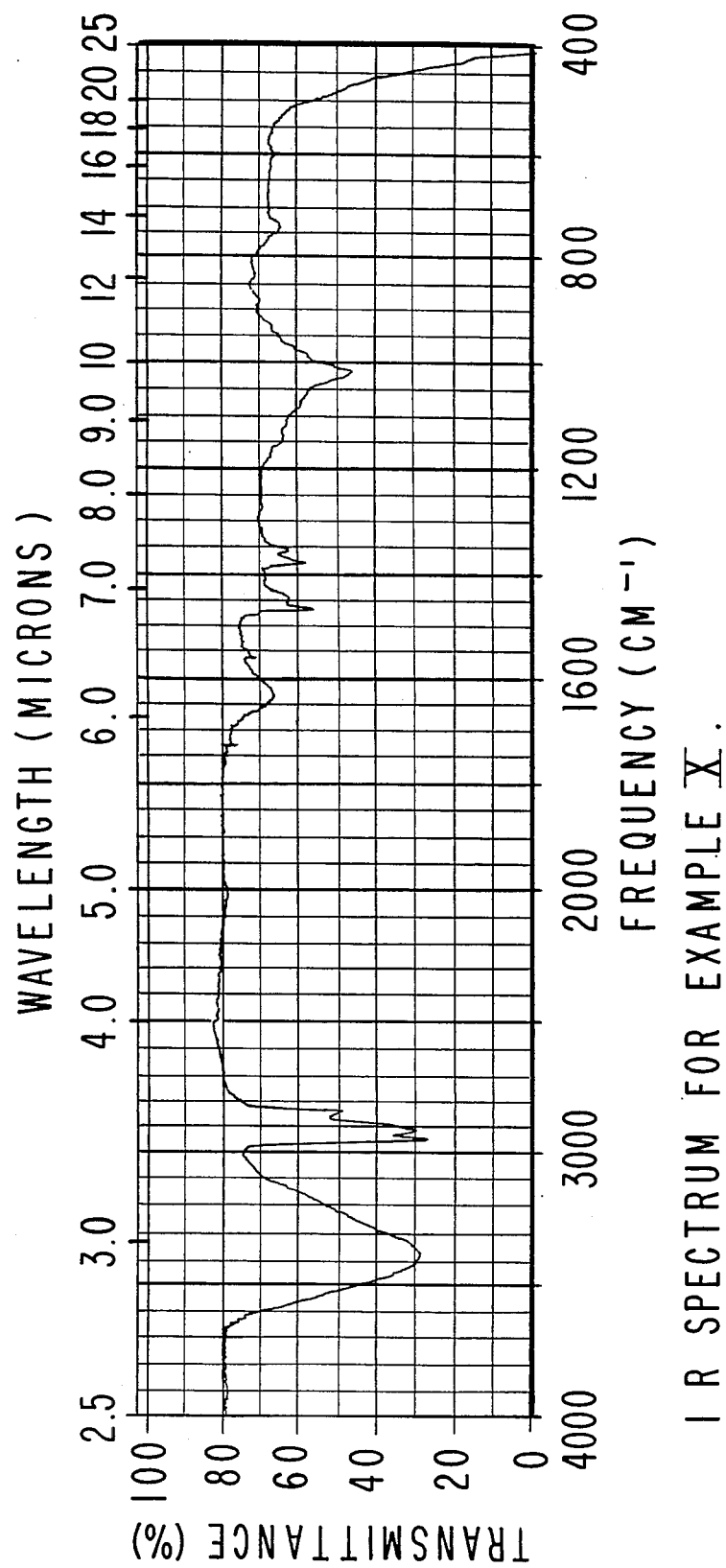
FIG. 30-B
IR SPECTRUM FOR EXAMPLE X.

GLC PROFILE FOR EXAMPLE XI.

FIG. 32 NMR SPECTRUM FOR EXAMPLE XI

IR SPECTRUM FOR EXAMPLE XI

341

GLC PROFILE FOR EXAMPLE XII.

IR SPECTRUM FOR EXAMPLE XII.

POLYALKYL-SUBSTITUTED OXOCYCLOHEPTANE DERIVATIVES, ORGANOLEPTIC USES THEREOF AND PROCESSES FOR PREPARING SAME

BACKGROUND OF THE INVENTION

This invention relates to polyalkyl-substituted oxocycloheptane derivatives defined according to the generic structure:

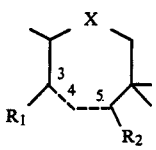

wherein one of the dashed lines is a carbon-carbon double bond and the other of the dashed lines is a carbon-carcon single bond; or both dashed lines are carbon-carbon single bonds; wherein $R_1$ and $R_2$ represents hydrogen or lower alkyl with the proviso that when the dashed line at the 4–5 position is a double bond, $R_2$ is hydrogen and when the dashed line at the 3–4 position is a double bond, $R_1$ is hydrogen; wherein $R_4$ represents $C_1$–$C_4$ lower alkyl; and wherein Y represents chloro or bromo, perfumery uses thereof and processes for preparing same.

Inexpensive chemical compositions of matter which can provide fruity, fresh, minty, earthy, camphoraceous, sweaty, animalic, woody, patchouli-like, rooty, seedy, piney, cedarwood-like, herbaceous, dried fruit and tobacco-like aromas with fruity, dried fruit, rose, orris-like and pennyroyal-like topnotes and with fruity and ionone-like undertones are highly desirable in the art of perfumery. Many of the natural materials which provide such fragrance nuances and contribute such desired nuances to perfumery compositions as well as perfumed articles including solid or liquid anionic, cationic, nonionic or zwitterionic detergents, fabric softener compositions and fabric softener articles as well as perfumed polymers are high in cost, vary in quality from one batch to another and/or are generally subject to the usual variations of natural products.

There is, accordingly, a continuing effort to find synthetic materials which will replace, enhance or augment the esential fragrance notes provided by natural essential oils or compositions thereof. Unfortunately, many of the synthetic materials either have the desired nuances only to a relatively small degree, or else contribute undesirable or unwanted odor to the compositions. The search for materials which can provide a more refined rose aroma, for example, or a more refined musky/animalic aroma, for example, has been difficult and relatively costly in the areas of both natural products and synthetic products.

Provision of the polyalkyl-substituted oxocycloheptane derivatives of our invention is considered to substantially provide solutions for the aforementioned problems.

Oxocycloheptane derivatives which are polyalkyl substituted are known for use in perfumery. However, the specific polyalkyl-substituted oxocycloheptane derivatives of our invention are novel in the form prepared herein and the processes for using same are novel.

Thus, the process described in Example V of U.K. Patent Specification No. 1,159,188 Published on July 23, 1969 (describing 3,3-dimethyl acetyl cyclohexane as a perfume ingredient having a strong minty, herbaceous odor) actually produces a mixture which also contains the compound having the structure:

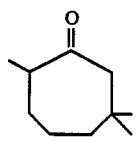

as determined by Hall and Lala, "Cyclization of Dimethyl-1,6-Octadienes, J. Org. Chem. 37, 920 (1972).

Chemical Abstracts, Volume 105, No. 227080a (Abstract of Japan Kokai 61/106532 Published on May 24, 1986) discloses the perfumery use of the compound having the structure:

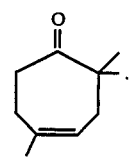

Japan Kokai No. J61/218543 Published on Sept. 29, 1986 discloses the perfumery use of the compound having the structure:

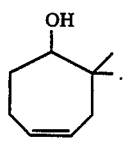

Japan Kokai No. 61/218543 also discloses the perfumery use of the compound having the structure:

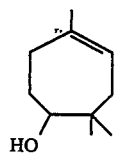

as having a woody and mint aroma. Japan Kokai No. J61/218543 is abstracted at Chemical Abstracts, Volume 106, 120103q (1987).

European Published Patent Application No. 193008 Published on Sept. 3, 1986 (abstracted at Chemical Abstracts, Volume 105, No. 225873y) discloses the perfumery use of the compounds having structures:

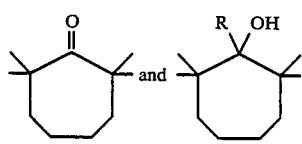

wherein R represents alkyl.

Although the compound having the structure:

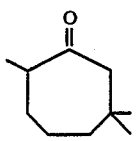

is disclosed as incidentally made in admixture in U.S. Pat. No. 3,869,411, at column 1, the substantially pure form of the compound:

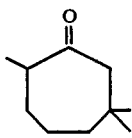

has never been produced and has unobvious, unexpected and advantageous properties in the field of perfumery. Furthermore, none of the other compounds of the genus of polyalkyl-substituted oxocycloheptane derivatives of our invention has been described in the prior art. The compositions of matter of our invention have unexpected, unobvious and advantageous properties when compared with other oxocycloheptanes, which are polyalkyl-substituted of the prior art.

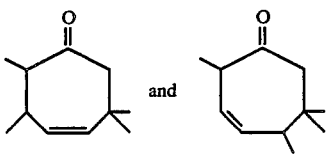

(Conditions: 30 m×0.32 mm SE-30 Column programmed at 100°–180° C. at 8° C. per minute).

Figure 2:
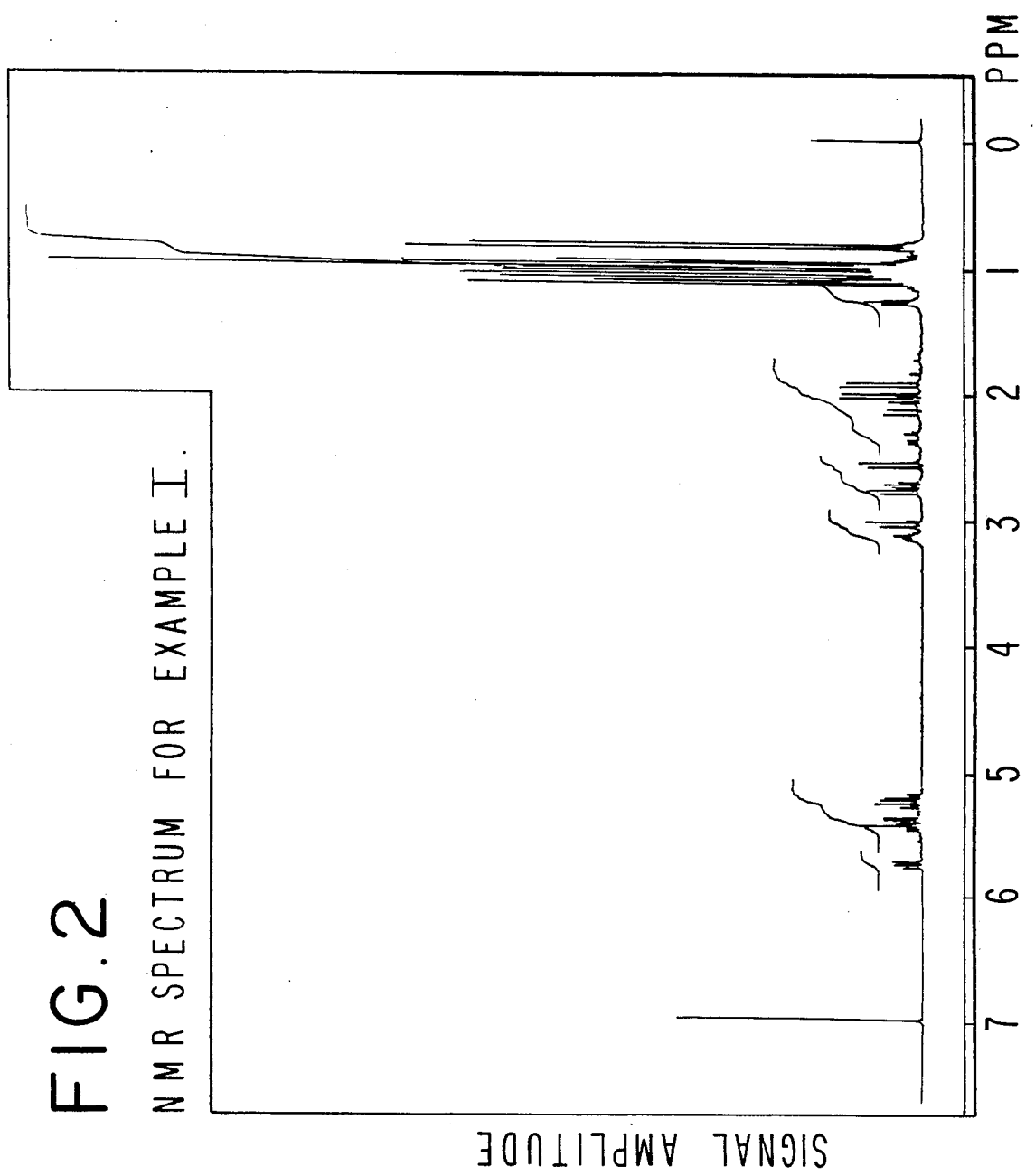

FIG. 2 is the NMR spectrum for the reaction product of Example I containing the compounds having the structures:

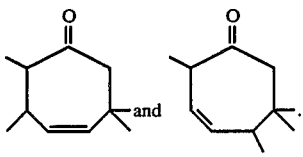

Figure 3:
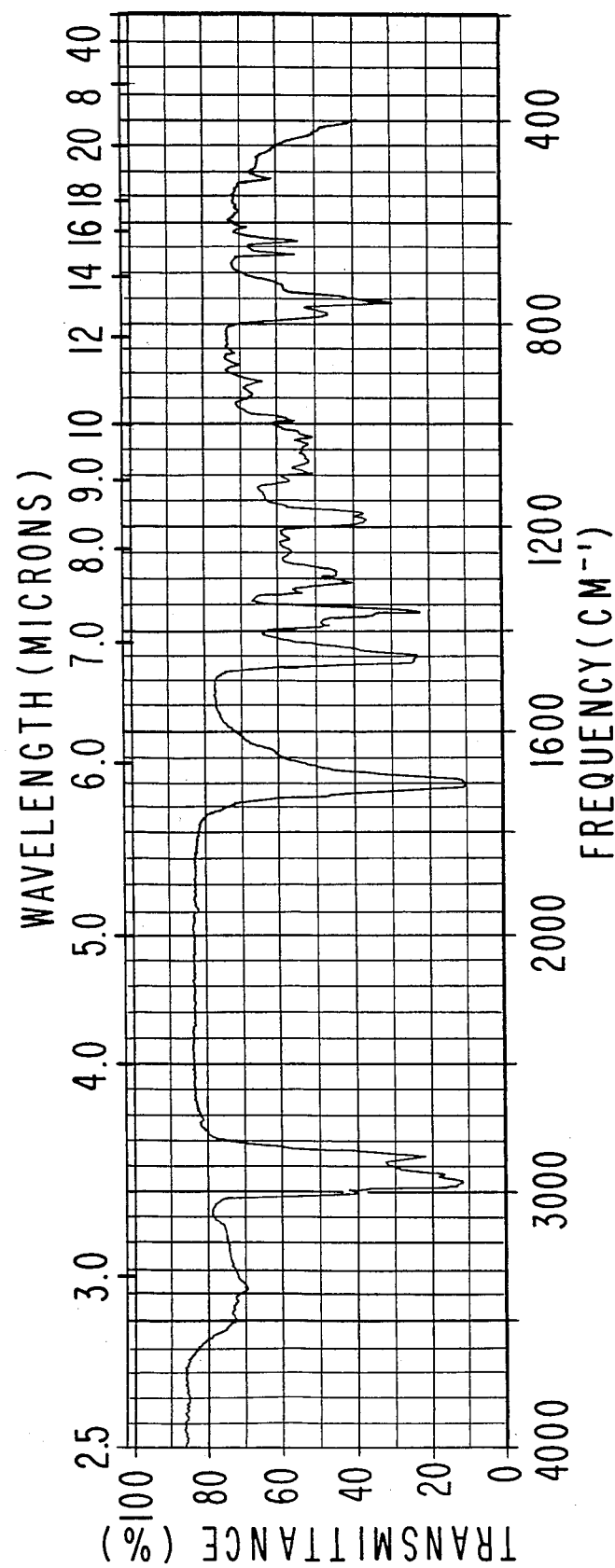

FIG. 3 is the infra-red spectrum for the reaction product of Example I containing the compounds having the structures:

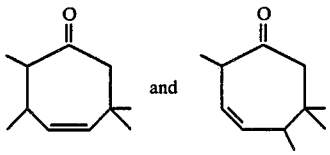

Figure 4:
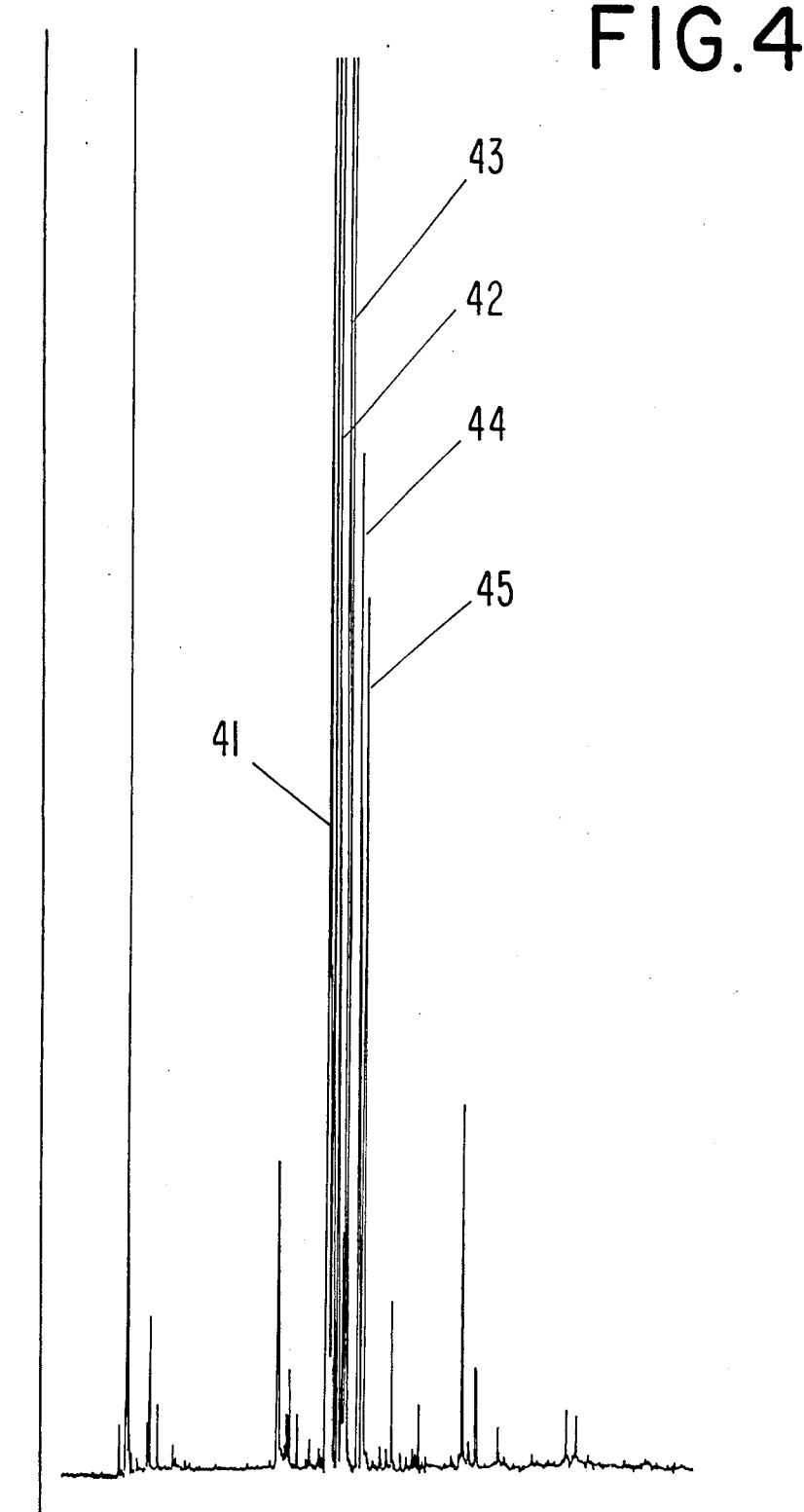

FIG. 4 is the GLC profile for the crude reaction product of Example II containing the compounds having the structures:

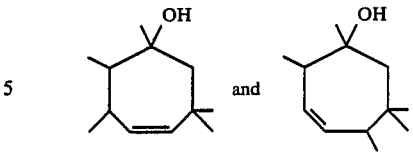

(Conditions: 30 m×0.32 mm carbowax-10 column programmed at 100°–180° C. at 8° C. per minute).

Figure 5:
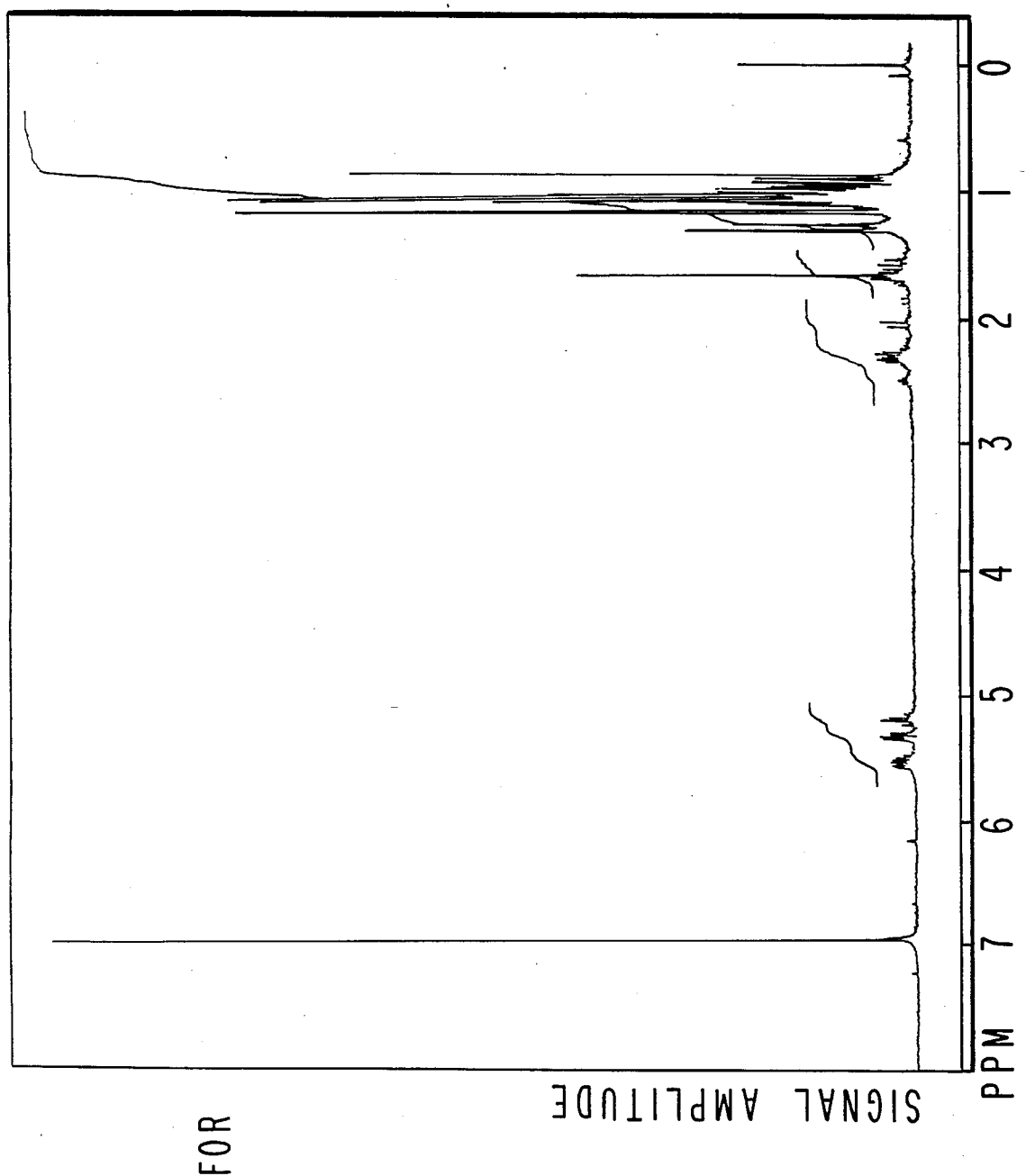

FIG. 5 is the NMR spectrum for the reaction product of Example II containing the compounds having the structures:

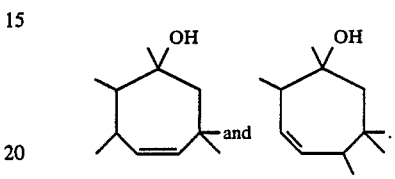

Figure 6:
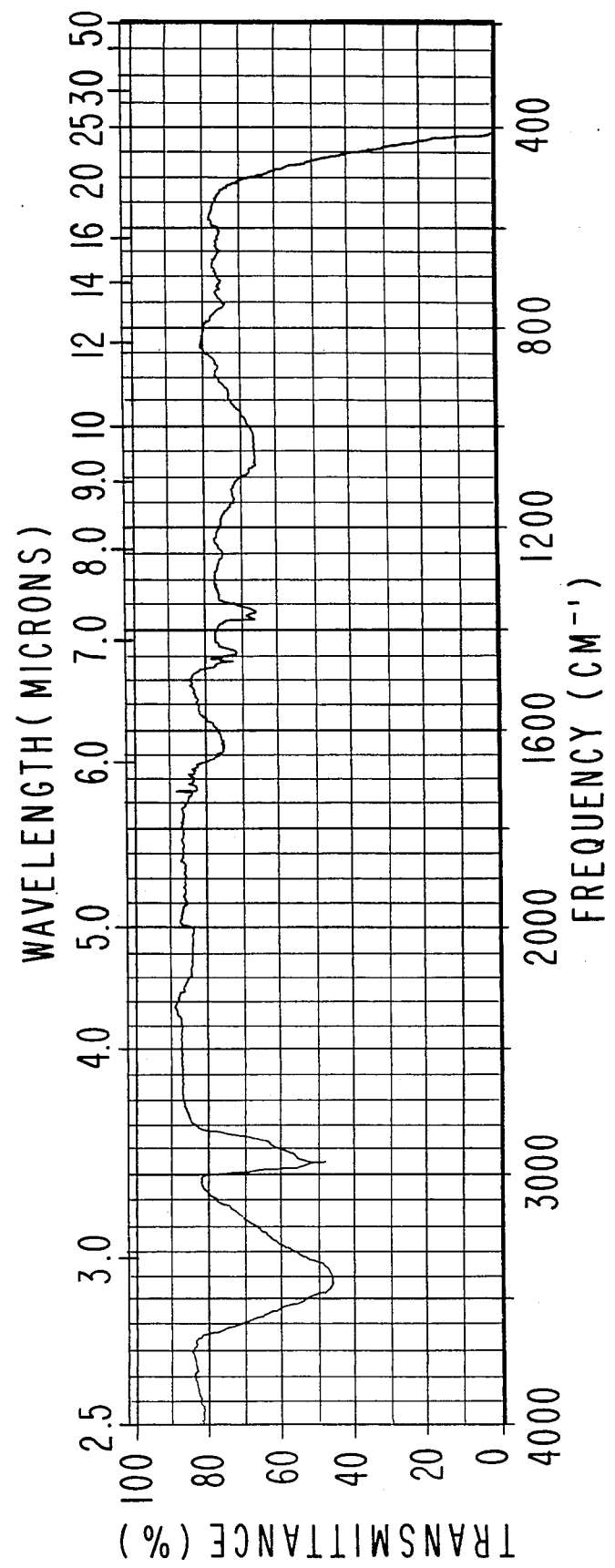

FIG. 6 is the infra-red spectrum for the reaction product of Example II containing the compounds having the structures:

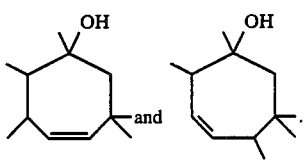

Figure 7:
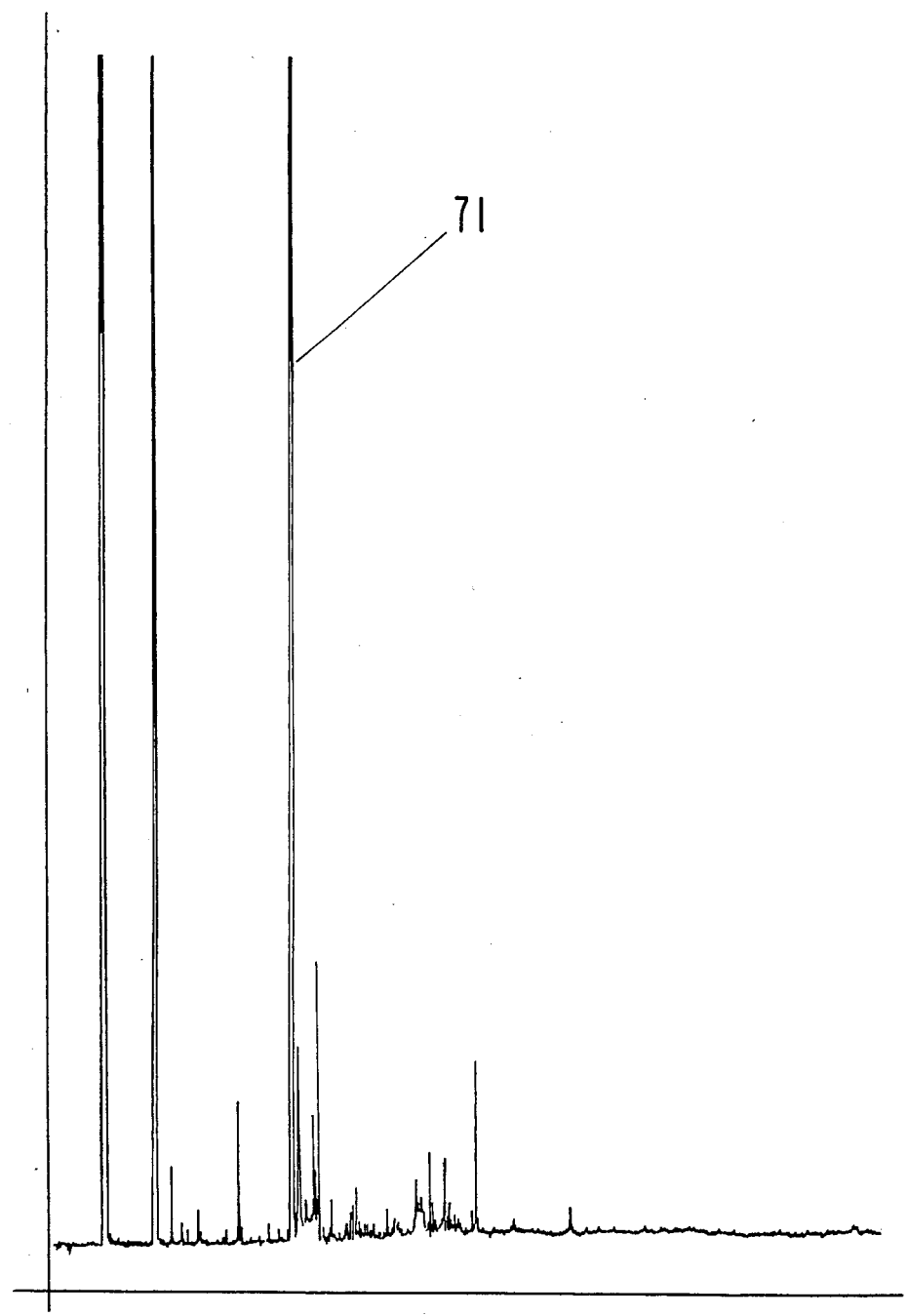

FIG. 7 is the GLC profile for the crude reaction product of Example III containing the compound having the structure:

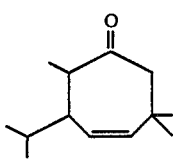

(Conditions: 30 m×0.32 mm carbowax column programmed at 100°–180° C. at 8° C. per minute).

Figure 8:
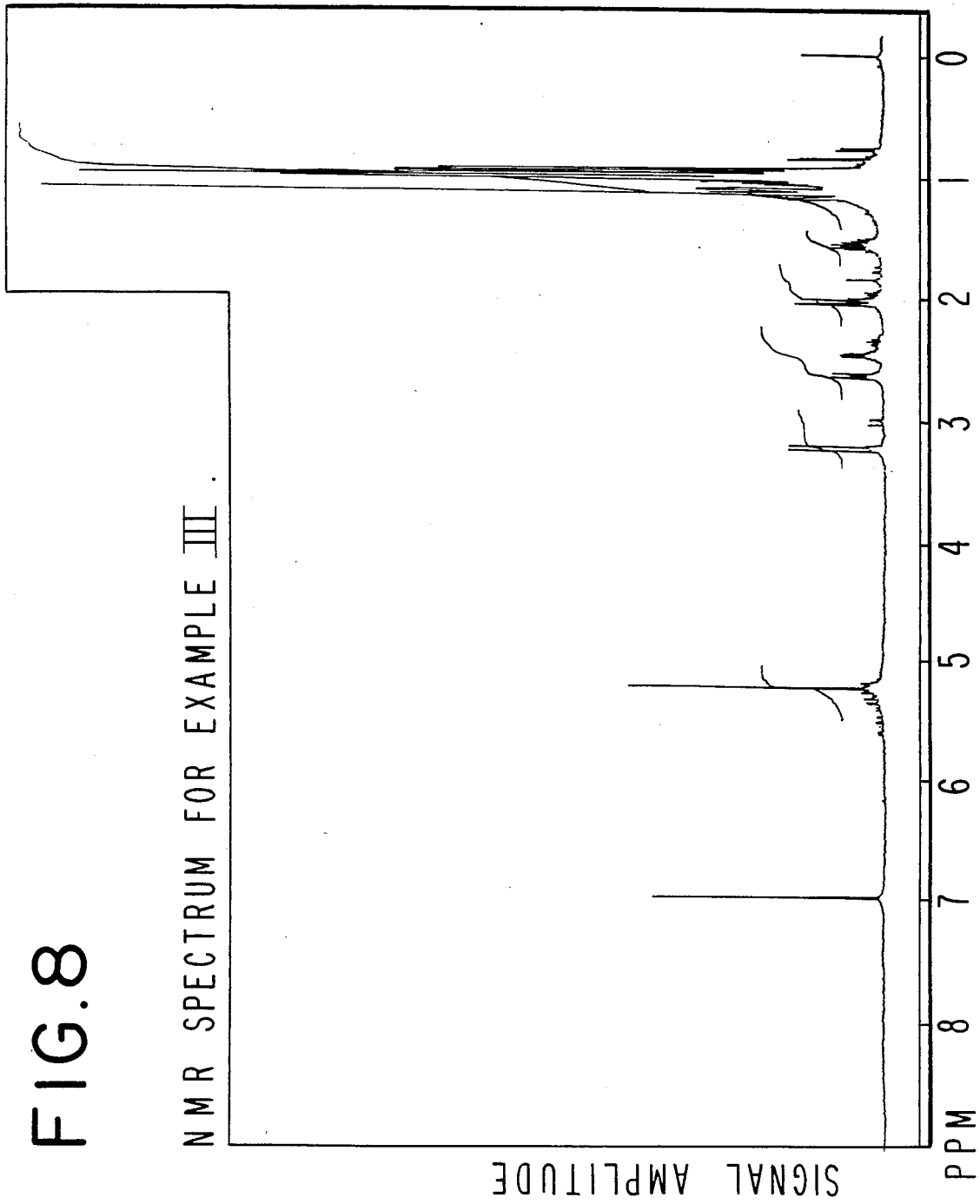

FIG. 8 is the NMR spectrum for the compound having the structure:

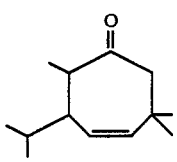

produced according to Example III.

Figure 9:
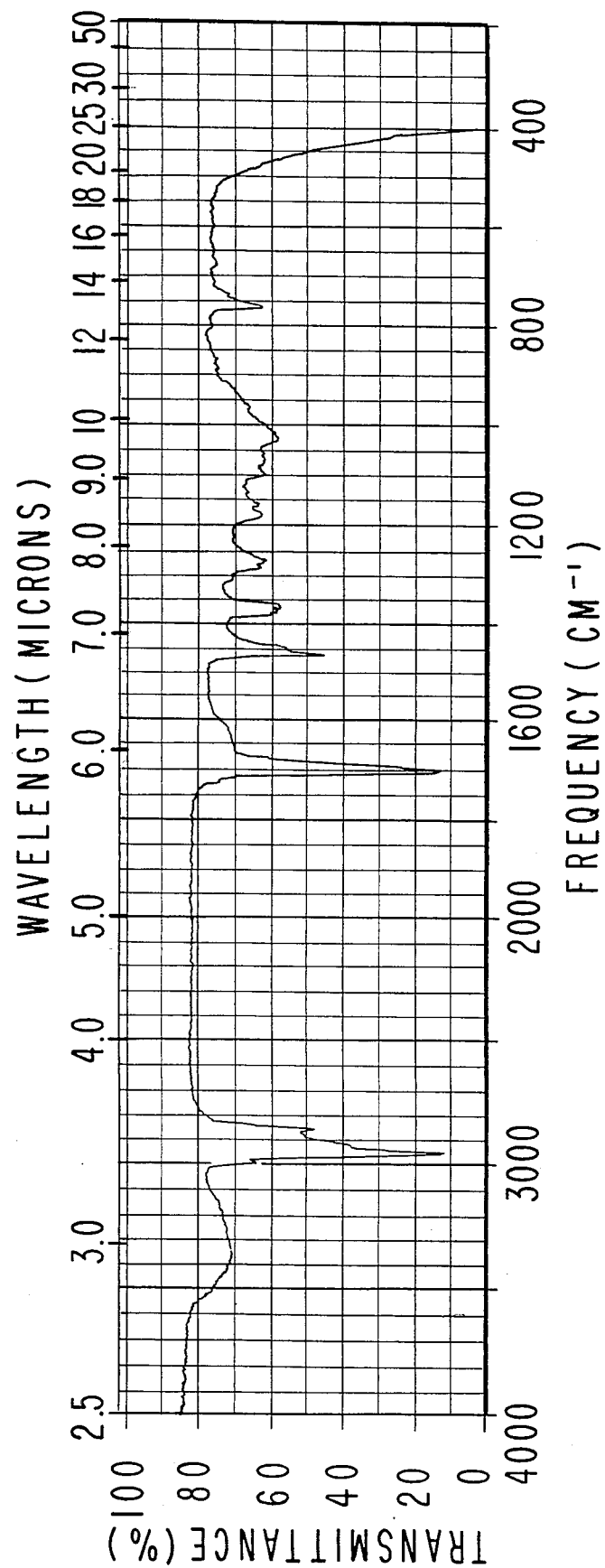

FIG. 9 is the infra-red spectrum for the compound having the structure:

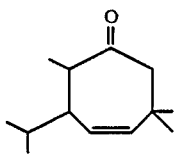

produced according to Example III.

Figure 10:
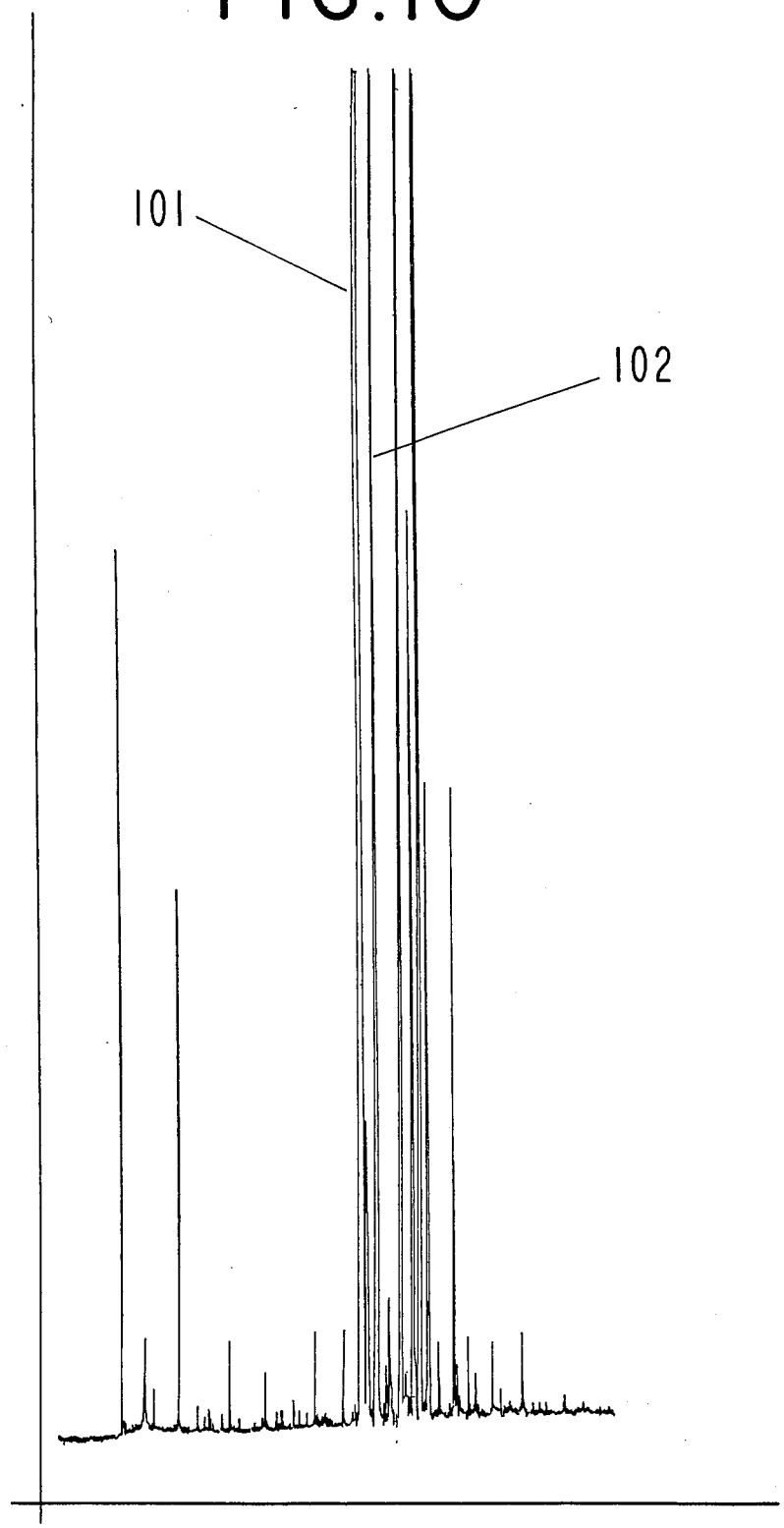

FIG. 10 is the GLC profile for the crude reaction product produced according to Example IV containing the compound having the structure:

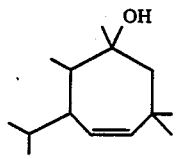

(Conditions: 30 m×0.32 mm carbowax-10 column programmed at 100°-180° C. at 8° C. per minute).

FIG. 11A is the NMR spectrum for peak 101 of the GLC profile of FIG. 10. FIG. 11A is the NMR spectrum for one of the isomers of the compound having the structure:

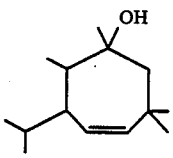

FIG. 11B is the NMR spectrum for the compound of peak 102 of the GLC profile of FIG. 10. FIG. 11B is the NMR spectrum for one of the isomers of the compound having the structure:

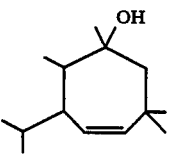

produced according to Example IV.

FIG. 12A is the infra-red spectrum for the compound of peak 101 in FIG. 10 having the structure:

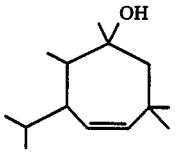

produced according to Example IV. FIG. 12A is the infra-red spectrum for one of the isomers of the compound having the structure:

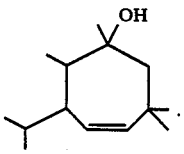

FIG. 12B is the infra-red spectrum for the compound of peak 102 of FIG. 10, one of the isomers of the compound having the structure:

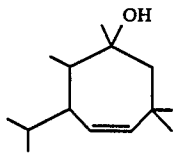

produced according to Example IV.

Figure 13:
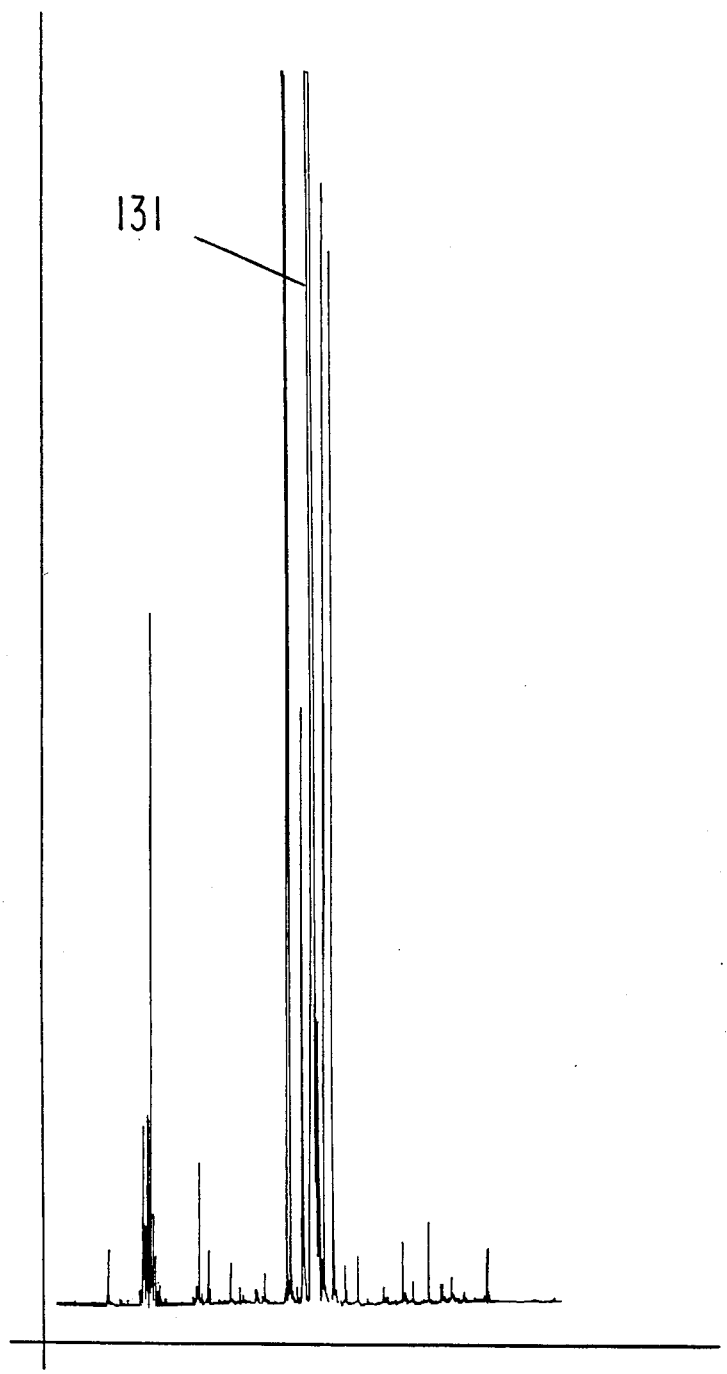

FIG. 13 is the GLC profile for the crude reaction product produced according to Example V containing the compound having the structure:

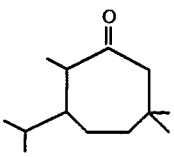

(Conditions: 30 m×0.32 mm carbowax-10 column programmed at 100°-180° C. at 8° C. per minute).

Figure 14:
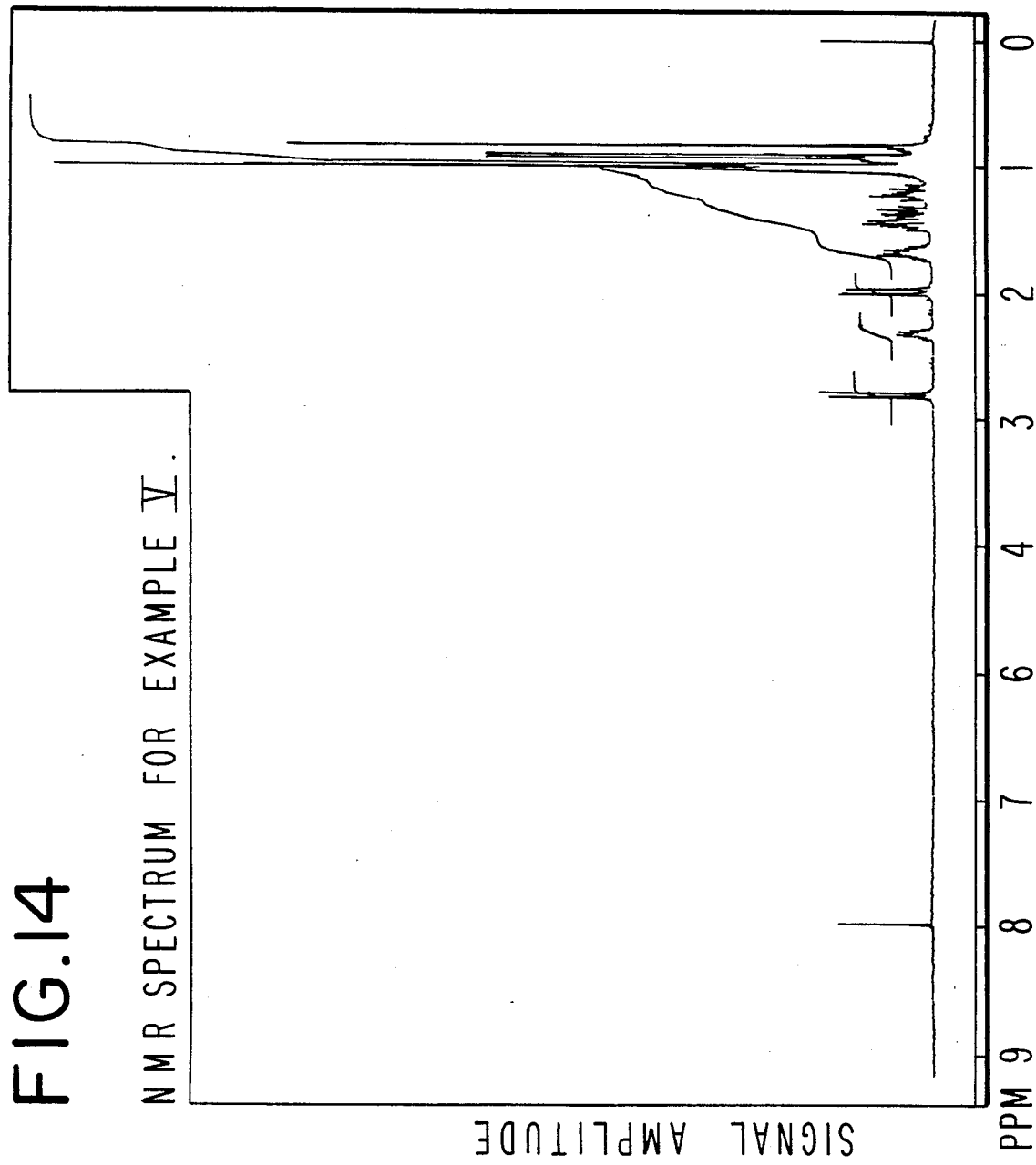

FIG. 14 is the GLC profile for the compound having the structure:

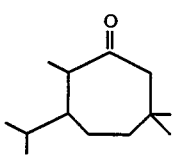

produced according to Example V.

Figure 15:
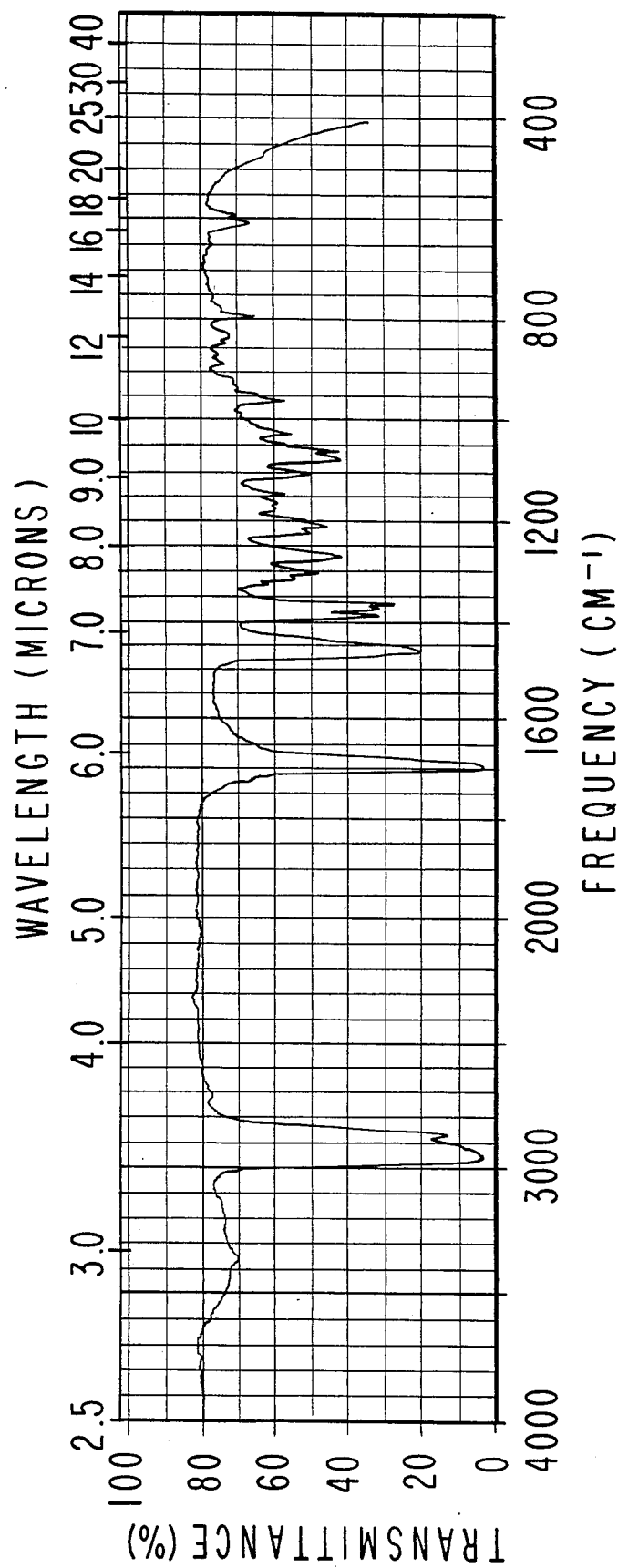

FIG. 15 is the infra-red spectrum for the compound having the structure:

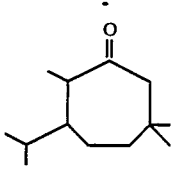

produced according to Example V.

Figure 16:
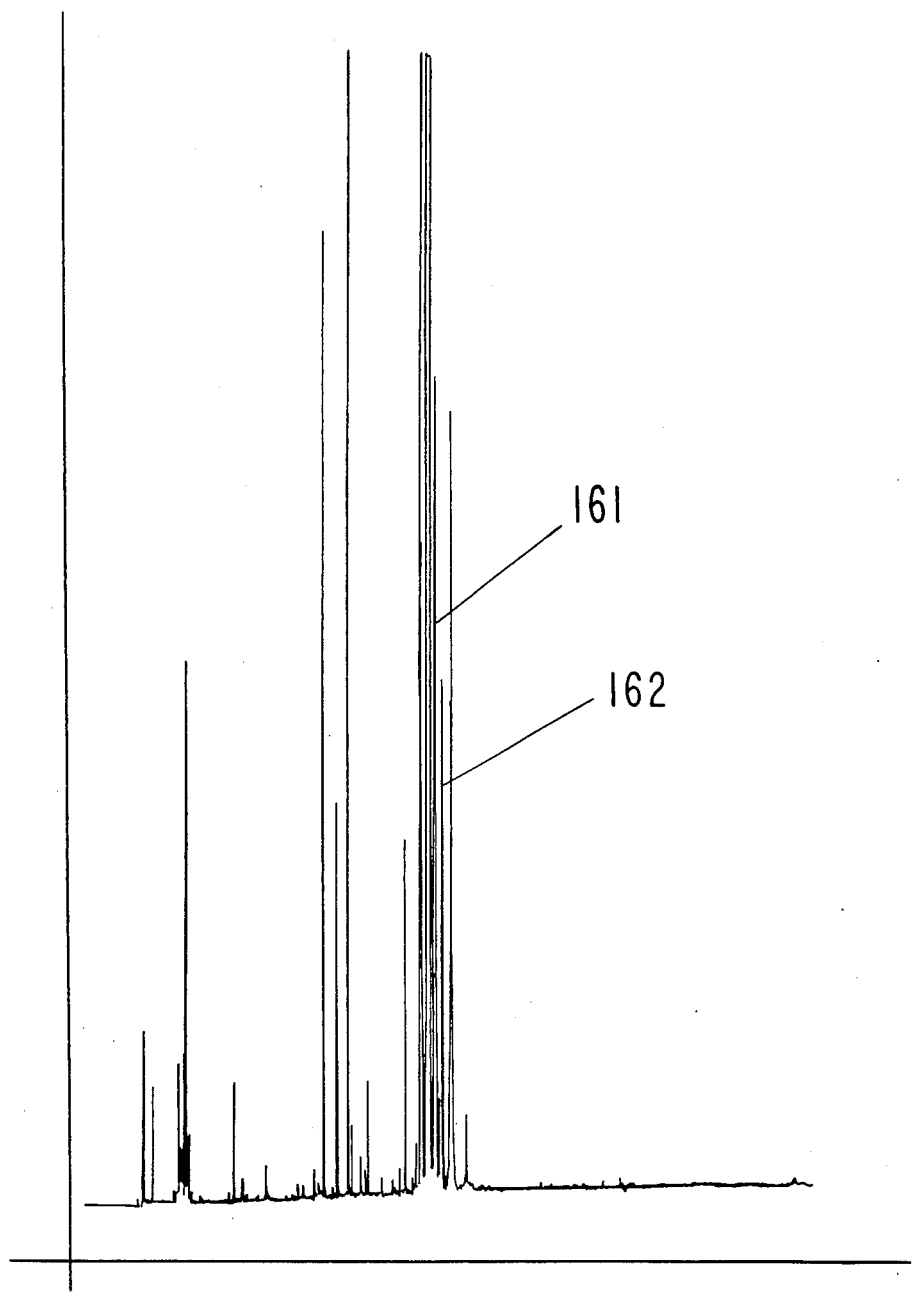

FIG. 16 is the GLC profile for the crude reaction product produced according to Example VI containing isomers of the compound having the structure:

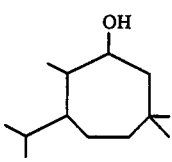

(Conditions: 30 m×0.32 mm carbowax-10 column programmed at 100°-180° C. at 8° C. per minute). The peaks for the isomers of the compound having the structure:

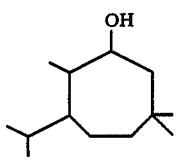

are indicated by reference numerals 161 and 162.

FIG. 17A is the NMR spectrum for one of the isomers produced according to Example VI having the structure:

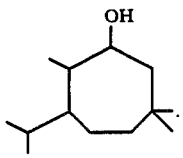

FIG. 17A is the NMR spectrum for peak 161 of FIG. 16.

FIG. 17B is the NMR spectrum for peak 162 of the GLC profile, FIG. 16. FIG. 17B is the NMR spectrum for one of the isomers produced according to Example VI having the structure:

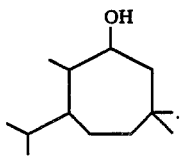

FIG. 18A is the infra-red spectrum for the peak indicated by reference numeral 161 in the GLC profile of FIG. 16. Peak 18A is the infra-red spectrum for one of the isomers of the compound having the structure:

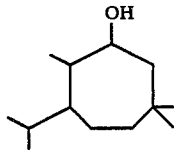

produced according to Example VI.

Figure 19:
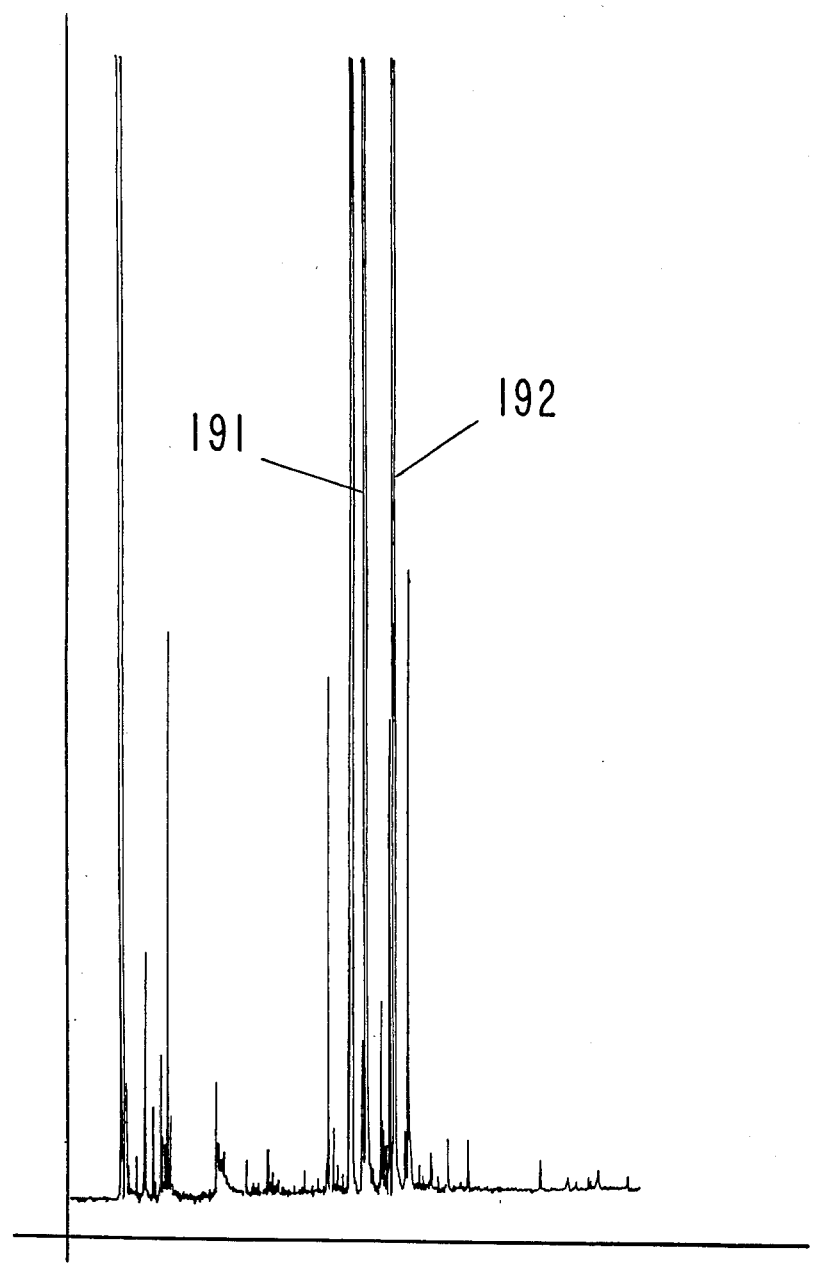

FIG. 18B is the infra-red spectrum for the compound having the structure:

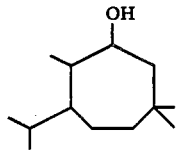

of peak 162 of FIG. 16, the GLC profile for the reaction product of Example VI. FIG. 18B is the infra-red spectrum for one of the isomers of the compound having the structure:

FIG. 19 is the GLC profile for the crude reaction product of Example VII containing the compound having the structure:

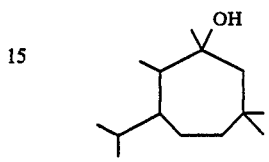

Peaks 191 and 192 are the peaks for the geometric isomers of the compound having the structure:

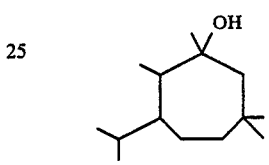

(Conditions: 30 m×0.32 mm carbowax-10 column programmed at 100°–180° C. at 8° C. per minute).

FIG. 20A is the NMR spectrum for an isomer of the compound having the structure:

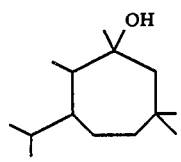

the compound of peak 191 of FIG. 19.

FIG. 20B is the NMR spectrum for an isomer of the compound having the structure:

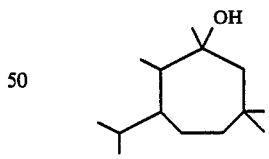

the compound of peak 192 of the GLC profile of FIG. 19.

FIG. 21A is the infra-red spectrum for peak 191, the peak for one of the isomers of the compound having the structure:

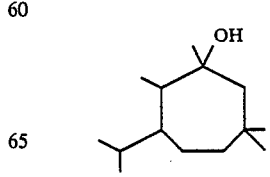

produced according to Example VII.

FIG. 21B is the infra-red spectrum for peak 192 of FIG. 19 for one of the isomers of the compound having the structure:

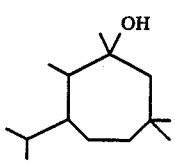

produced according to Example VII.

Figure 22:
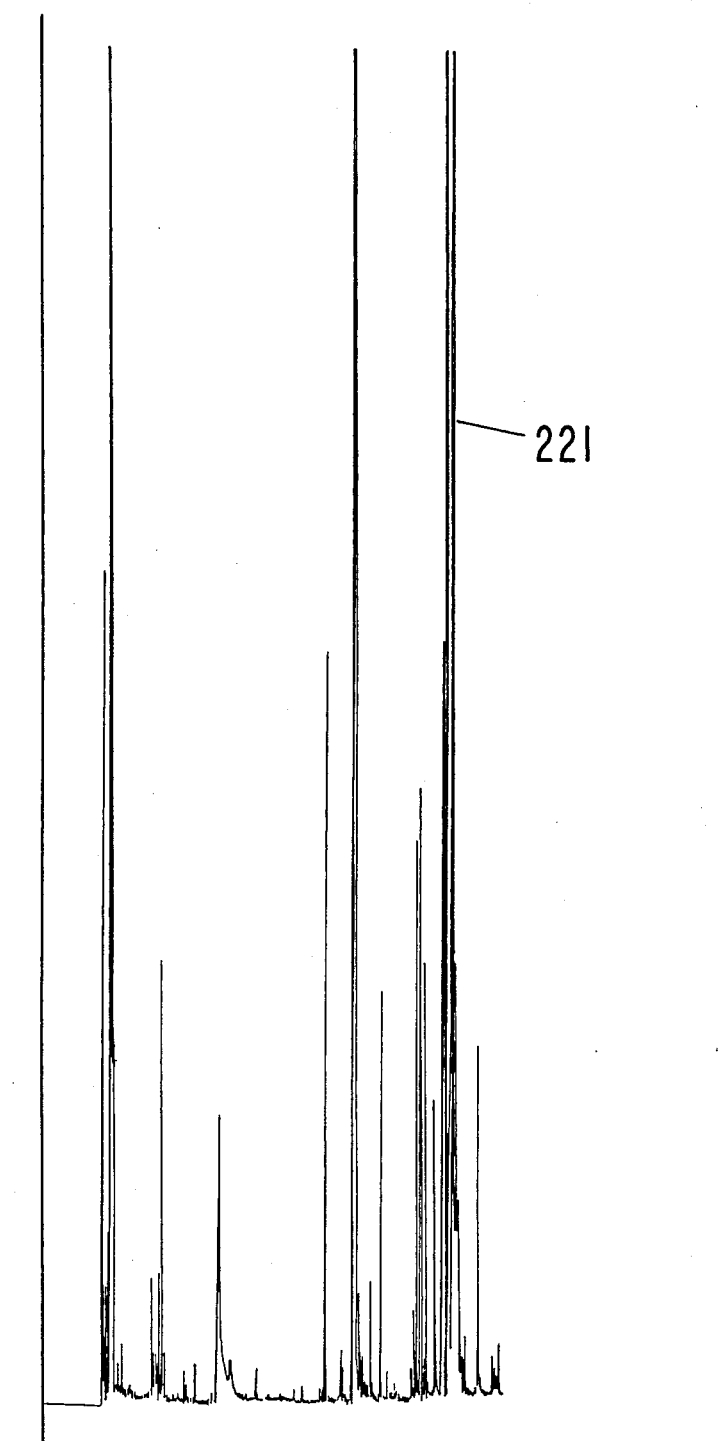

FIG. 22 is the GLC profile for the crude reaction product of Example VIII containing the compound having the structure:

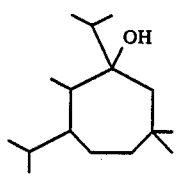

(Conditions: 30 m×0.32 mm supelcowax-10 (carbowax) column programmed at 100°-180° C. at 8° C. per minute).

Figure 23:
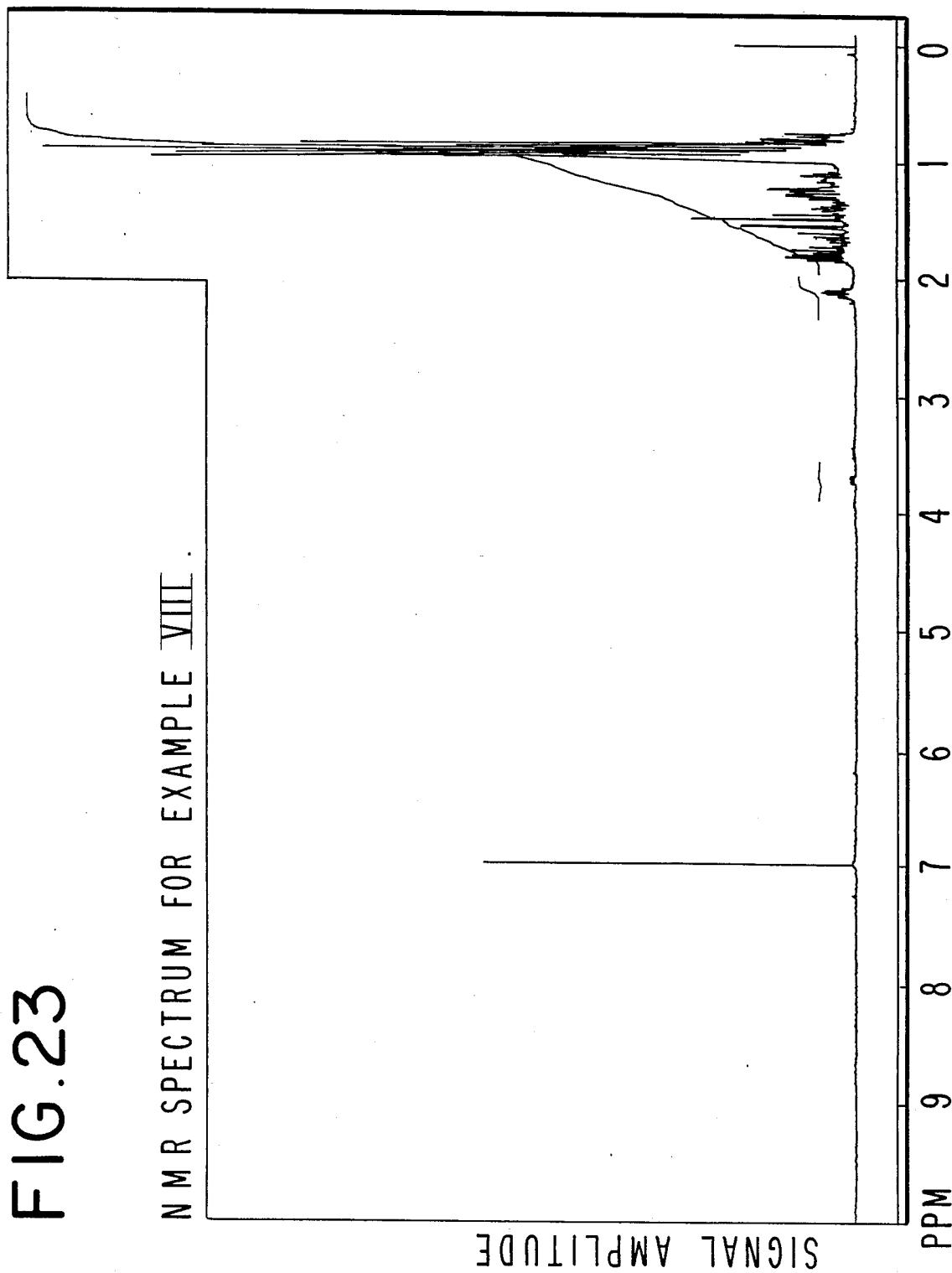

FIG. 23 is the NMR spectrum for the compound having the structure:

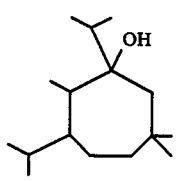

produced according to Example VIII.

Figure 24:
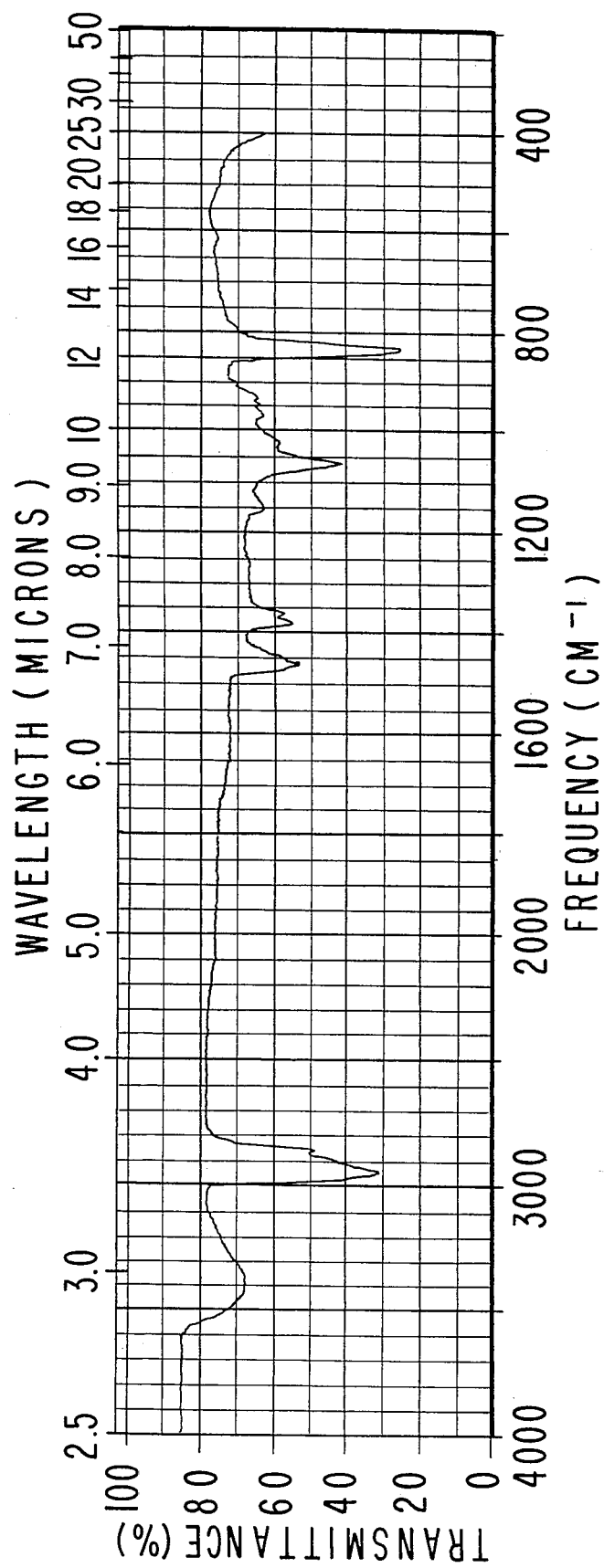

FIG. 24 is the infra-red spectrum for the compound having the structure:

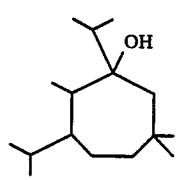

produced according to Example VIII.

Figure 25:
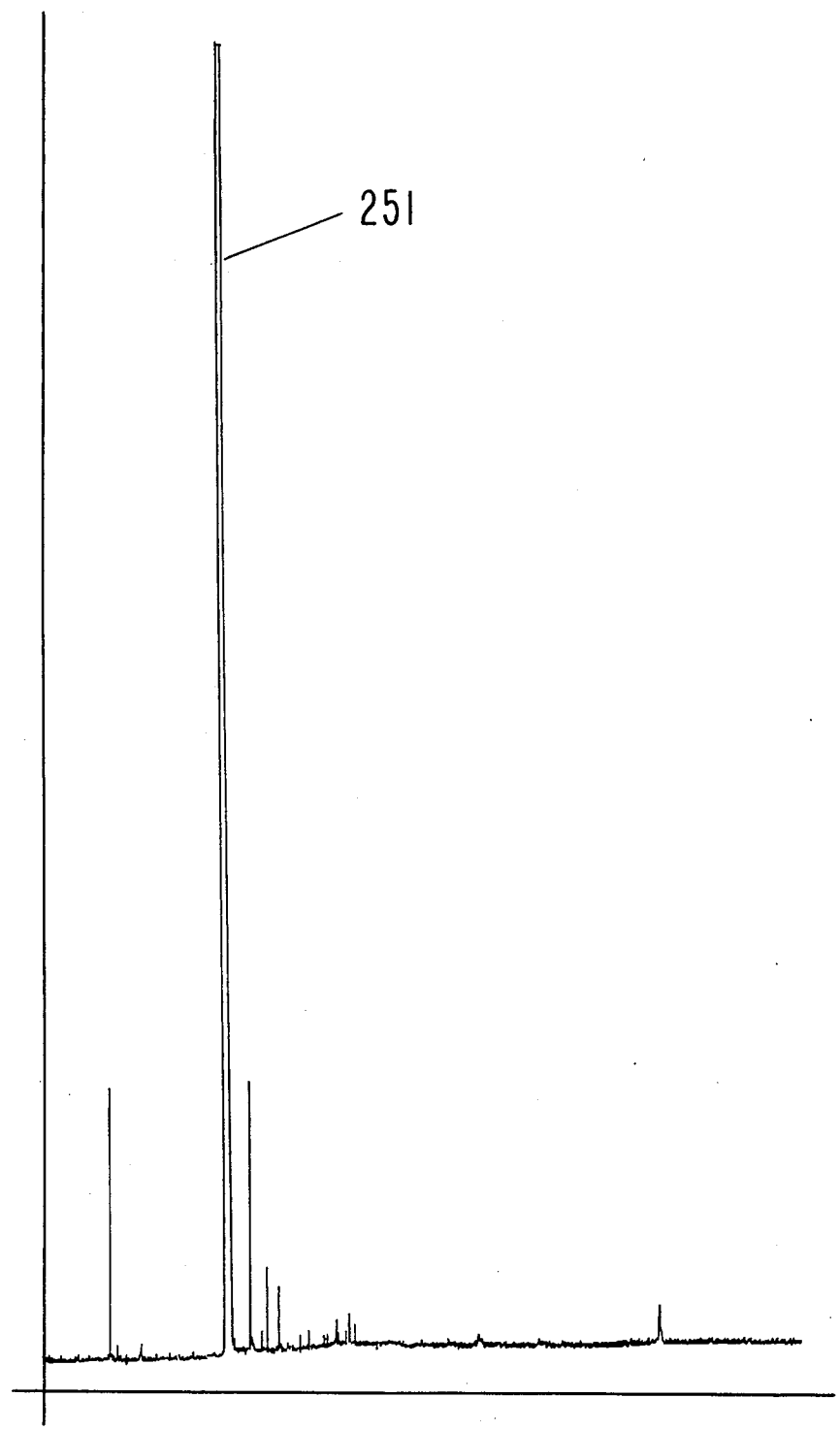

FIG. 25 is the GLC profile for the crude reaction product of Example IX containing the compound having the structure:

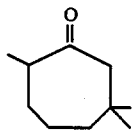

(Conditions: 30 m×0.32 mm supelcowax-10 (carbowax) column programmed at 100°-180° C. at 8° C. per minute).

Figure 26:
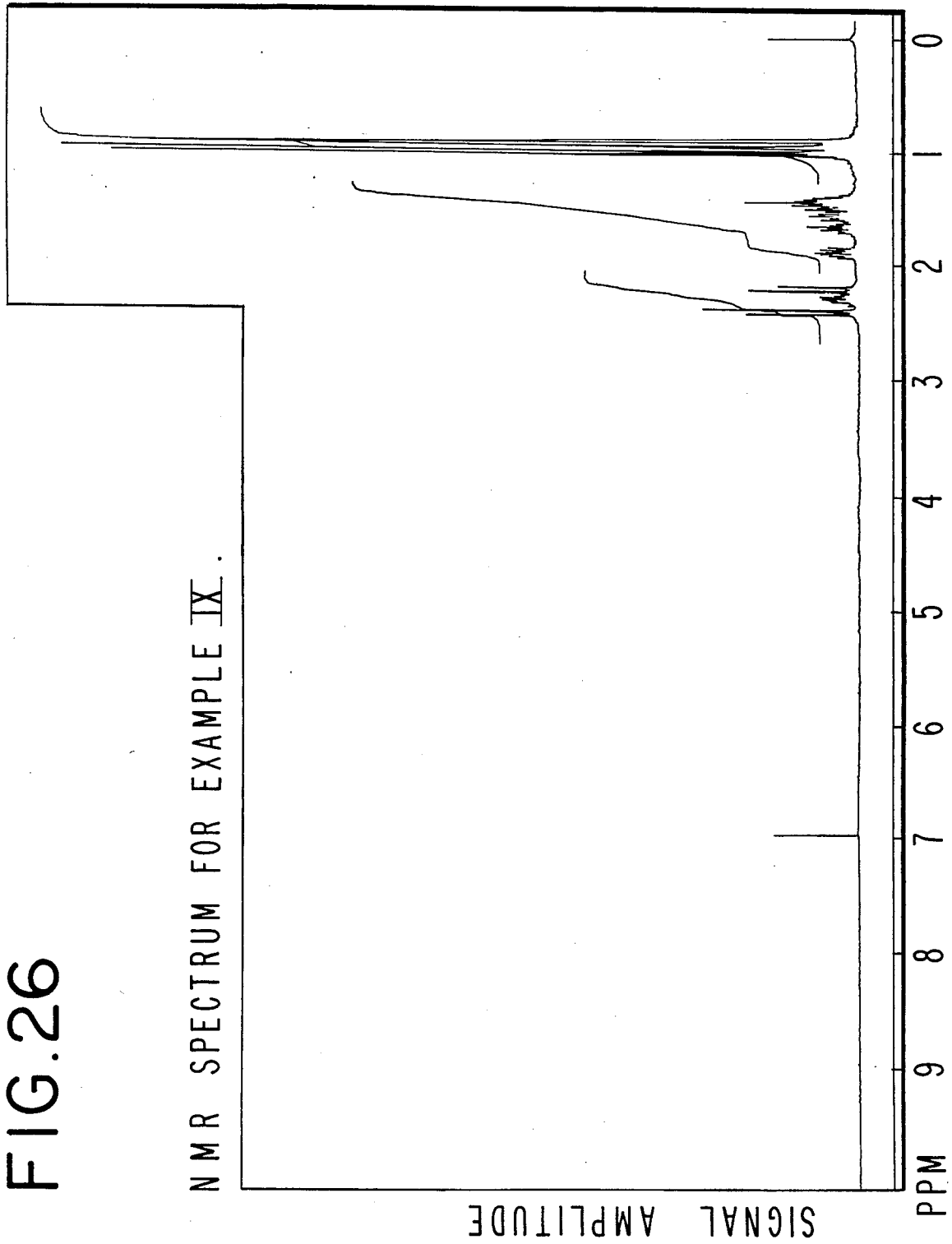

FIG. 26 is the NMR spectrum for the compound having the structure:

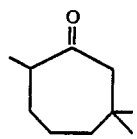

produced according to Example IX.

Figure 27:
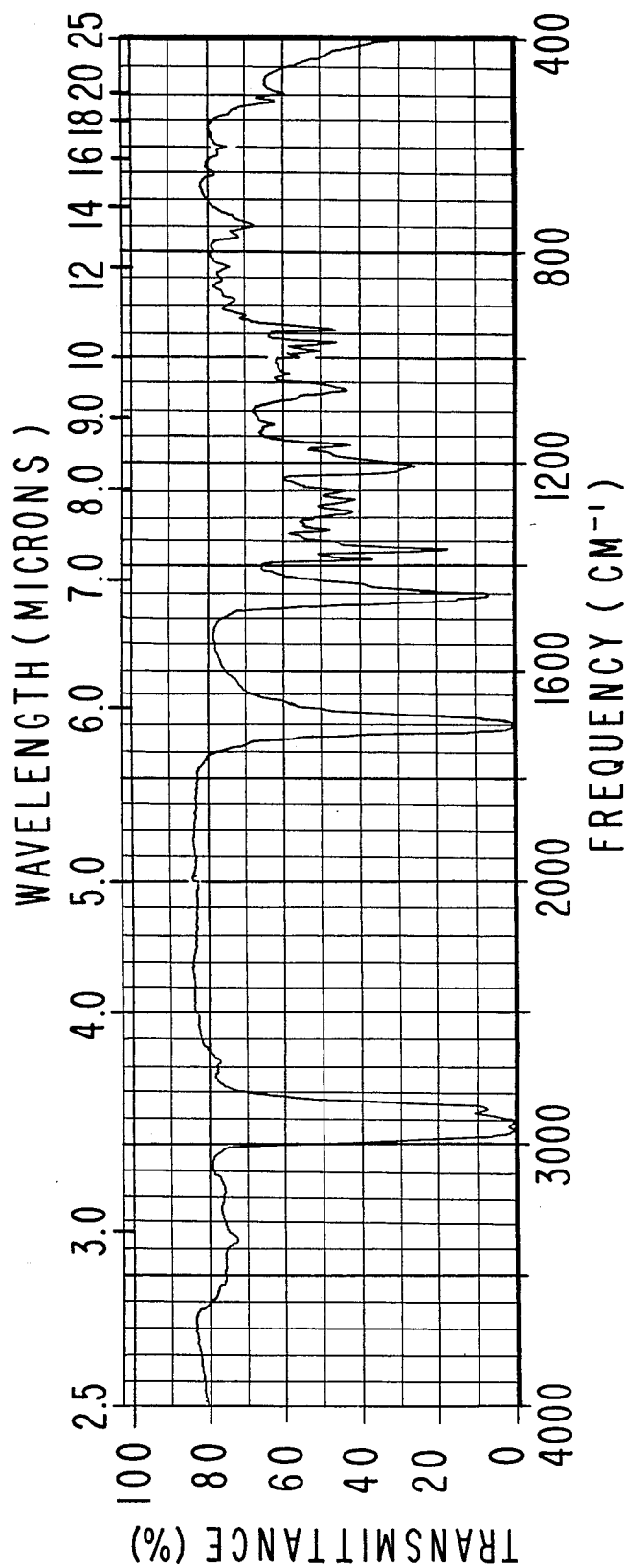

FIG. 27 is the infra-red spectrum for the compound having the structure:

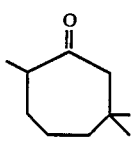

produced according to Example IX.

Figure 28:
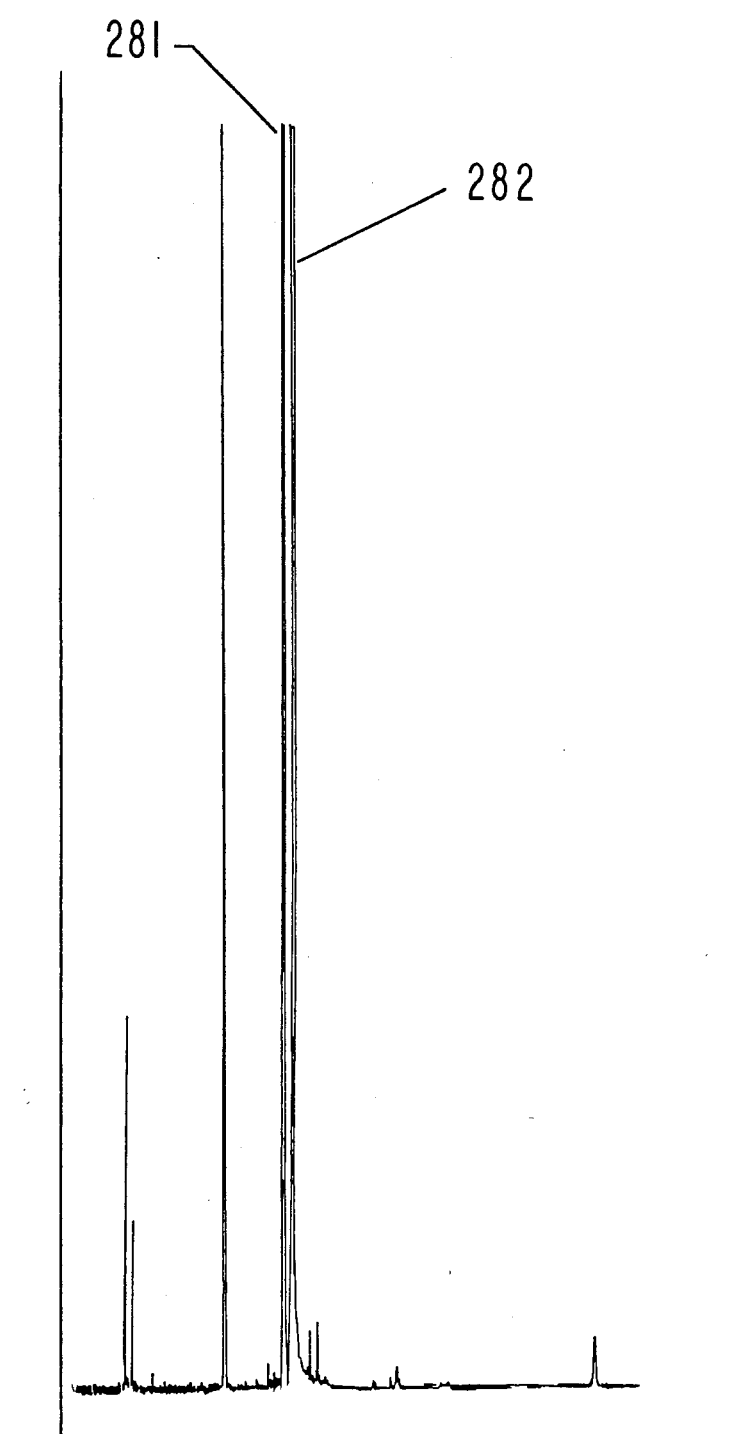

FIG. 28 is the GLC profile for the crude reaction product of Example X containing the compound having the structure:

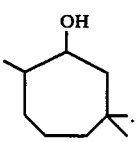

Peaks 281 and 282 are peaks for geometric isomers of the compound having the structure:

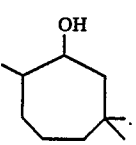

FIG. 29A is the NMR spectrum for one of the isomers of the compound having the structure:

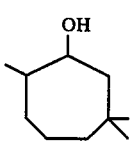

produced according to Example X, the compound of peak 281 of FIG. 28.

FIG. 29B is the NMR spectrum for one of the isomers of the compound having the structure:

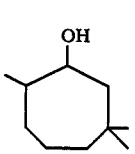

produced according to Example X, the isomer of peak 282 of FIG. 28.

FIG. 30A is the NMR spectrum for one of the isomers of the compound having the structure:

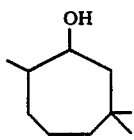

produced according to Example X, the isomer of peak 281 of FIG. 28.

FIG. 30B is the infra-red spectrum for peak 282 of FIG. 28 for one of the isomers of the compound having the structure:

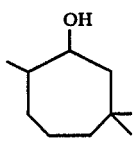

produced according to Example X.

Figure 31:
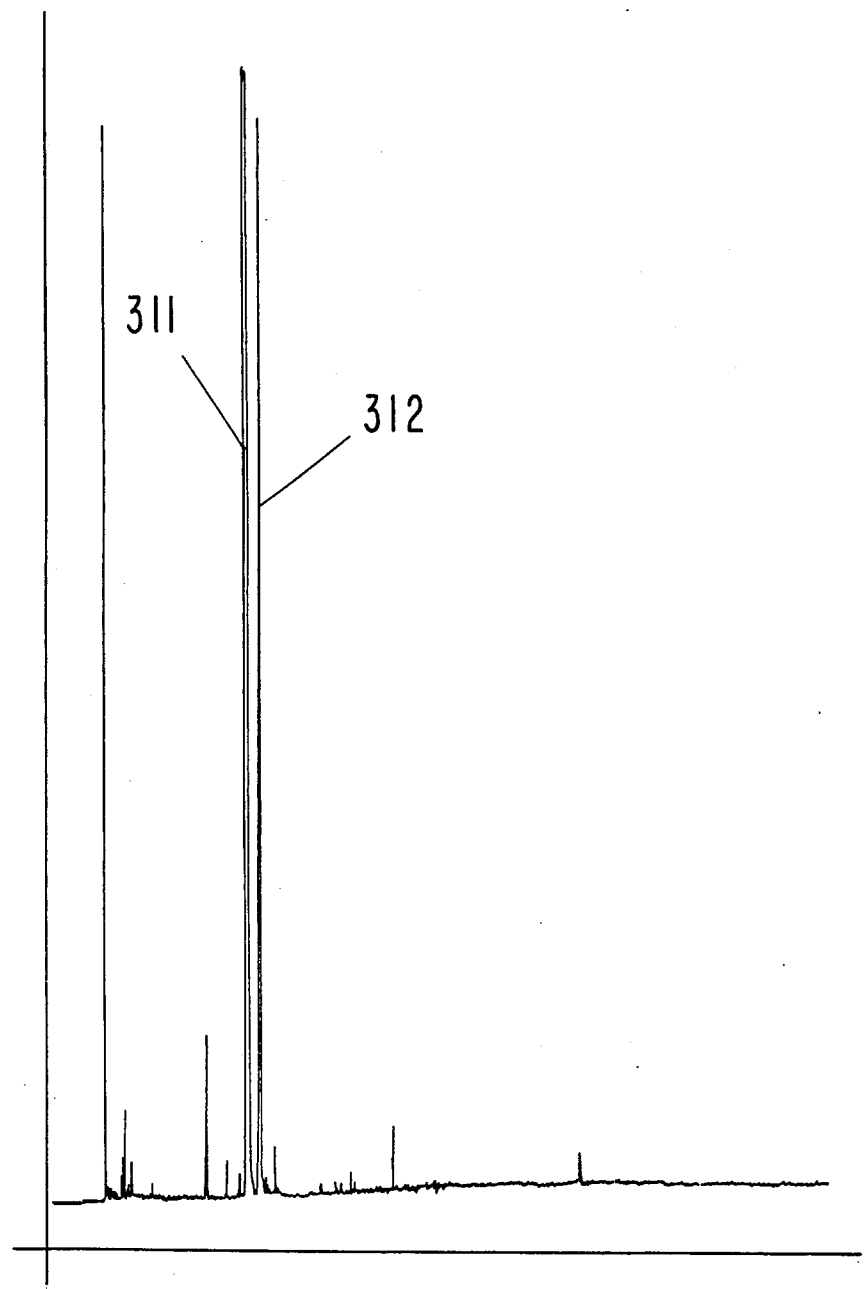

FIG. 31 is the GLC profile for the crude reaction product produced according to Example XI containing the compound having the structure:

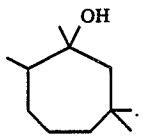

The peak indicated by reference numeral 311 is the peak for one of the isomers of the compound having the structure:

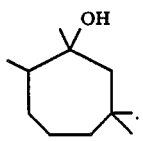

The peak indicated by reference numeral 312 is the peak for the other of the isomers having the structure:

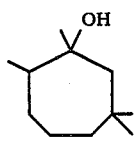

(Conditions: 30 m×0.32mm supelcowax-10 (carbowax) column programmed at 100°–180° C. at 8° C. per minute).

Figure 32:
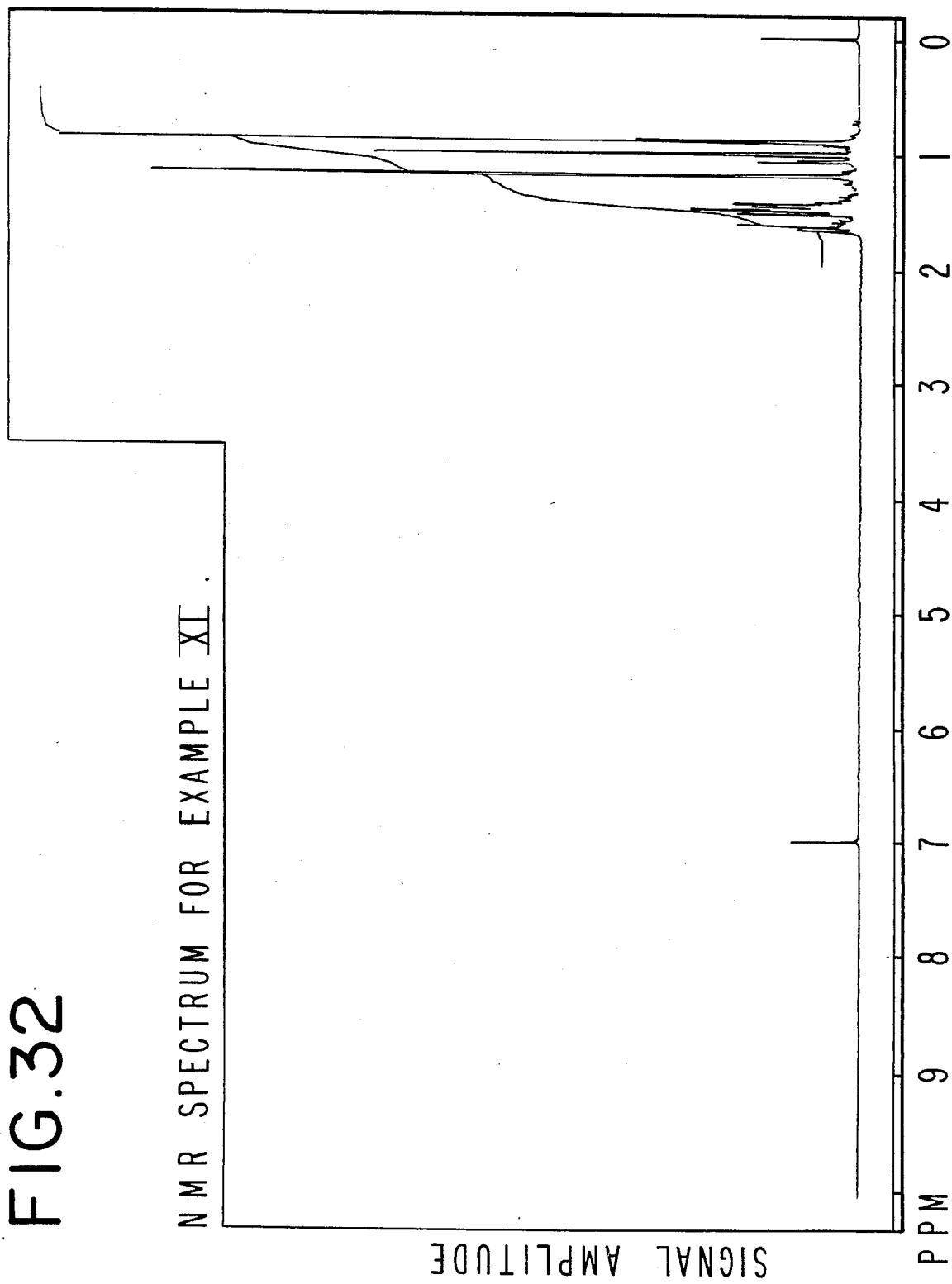

FIG. 32 is the NMR spectrum for the compound having the structure:

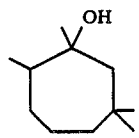

produced according to Example XI.

Figure 33:
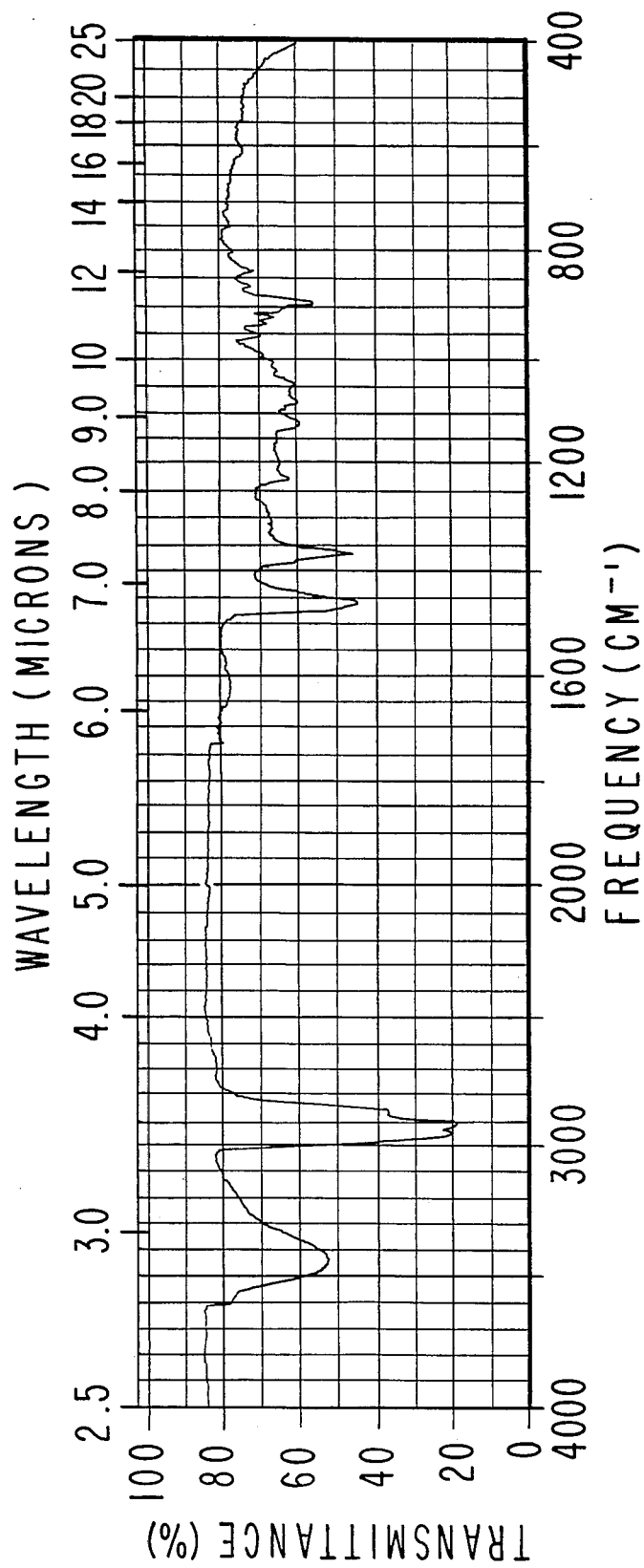

FIG. 33 is the infra-red spectrum for the compound having the structure:

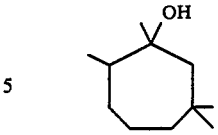

produced according to Example XI.

Figure 34:
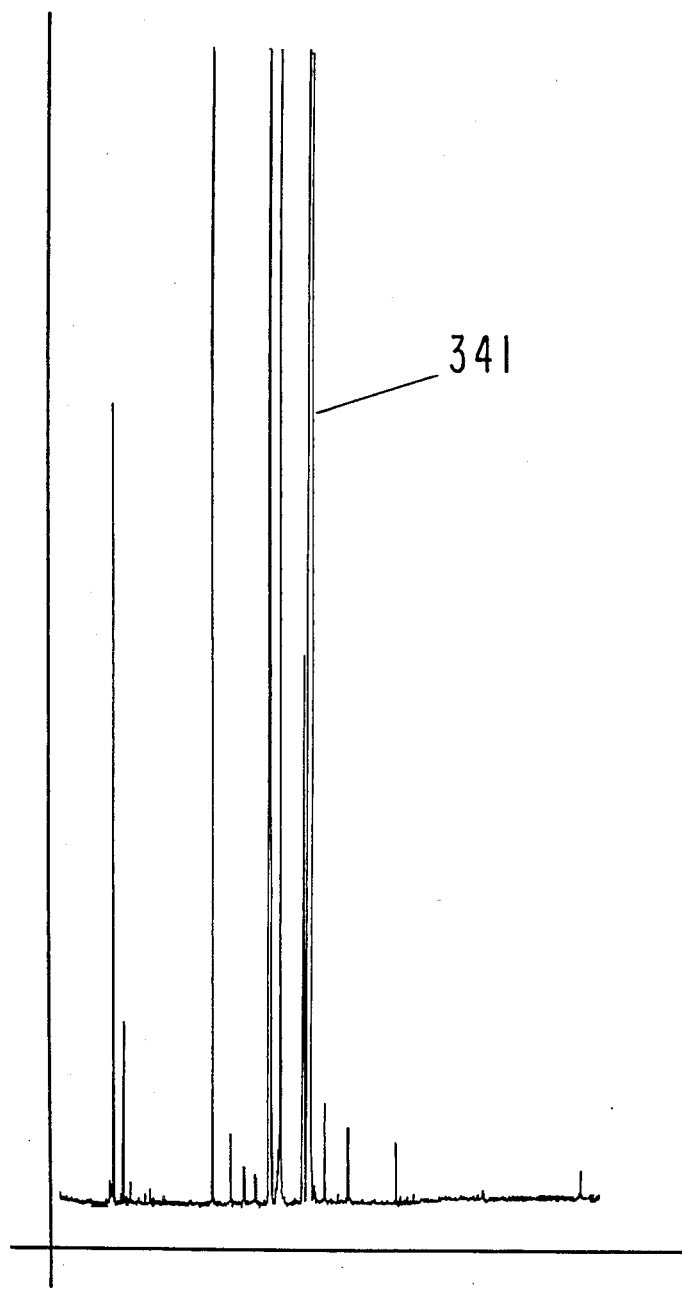

FIG. 34 is the GLC profile for the crude reaction product of FIG. XII containing the compound having the structure:

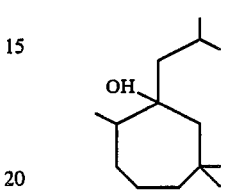

(Conditions: 30 m×0.32 mm supelcowax-10 (carbowax) column programmed at 100°–180° C. at 8° C. per minute.)

Figure 35:
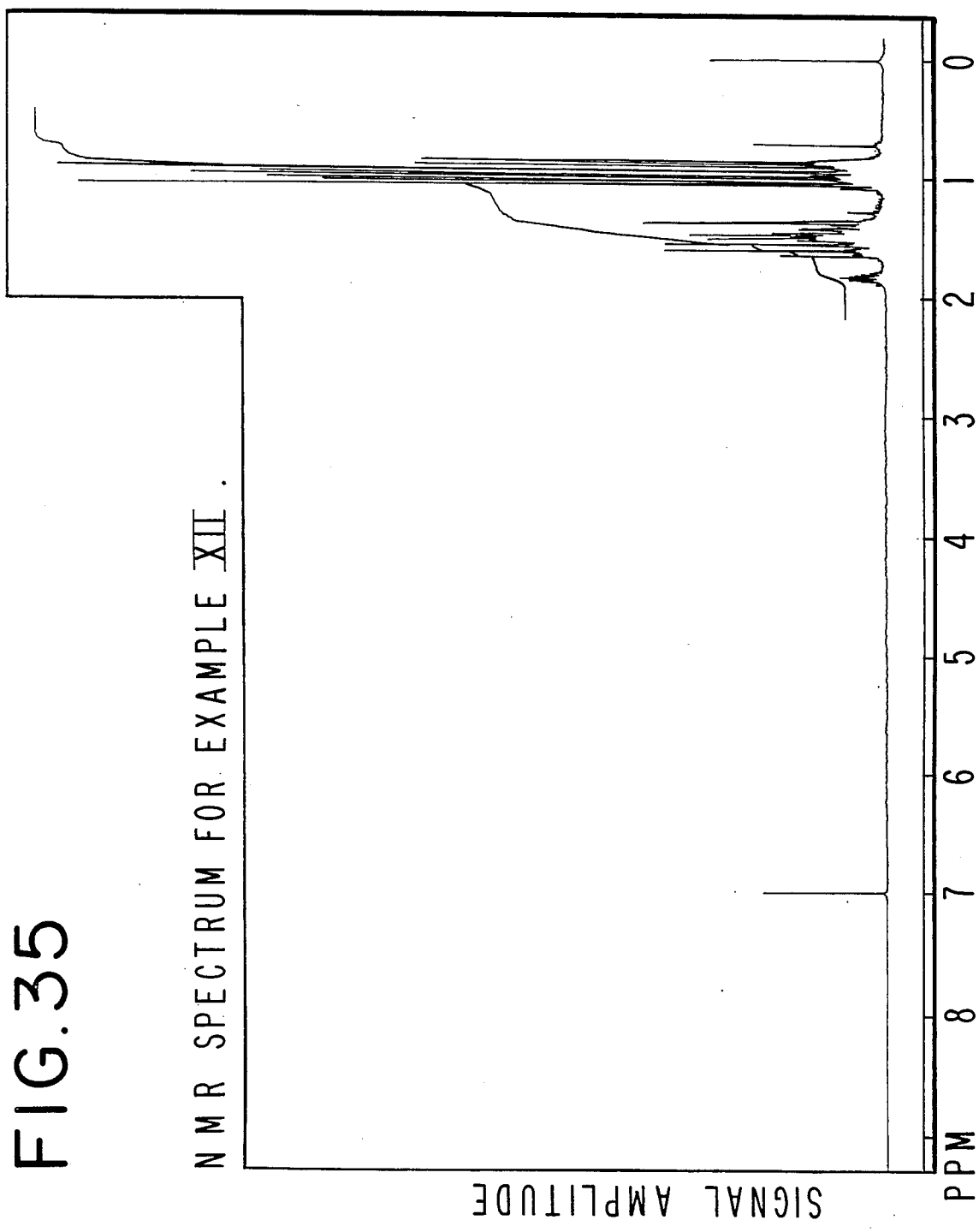

FIG. 35 is the NMR spectrum for the compound having the structure:

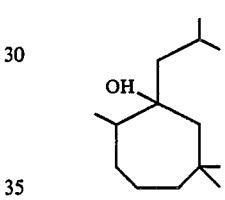

produced according to Example XII.

Figure 36:
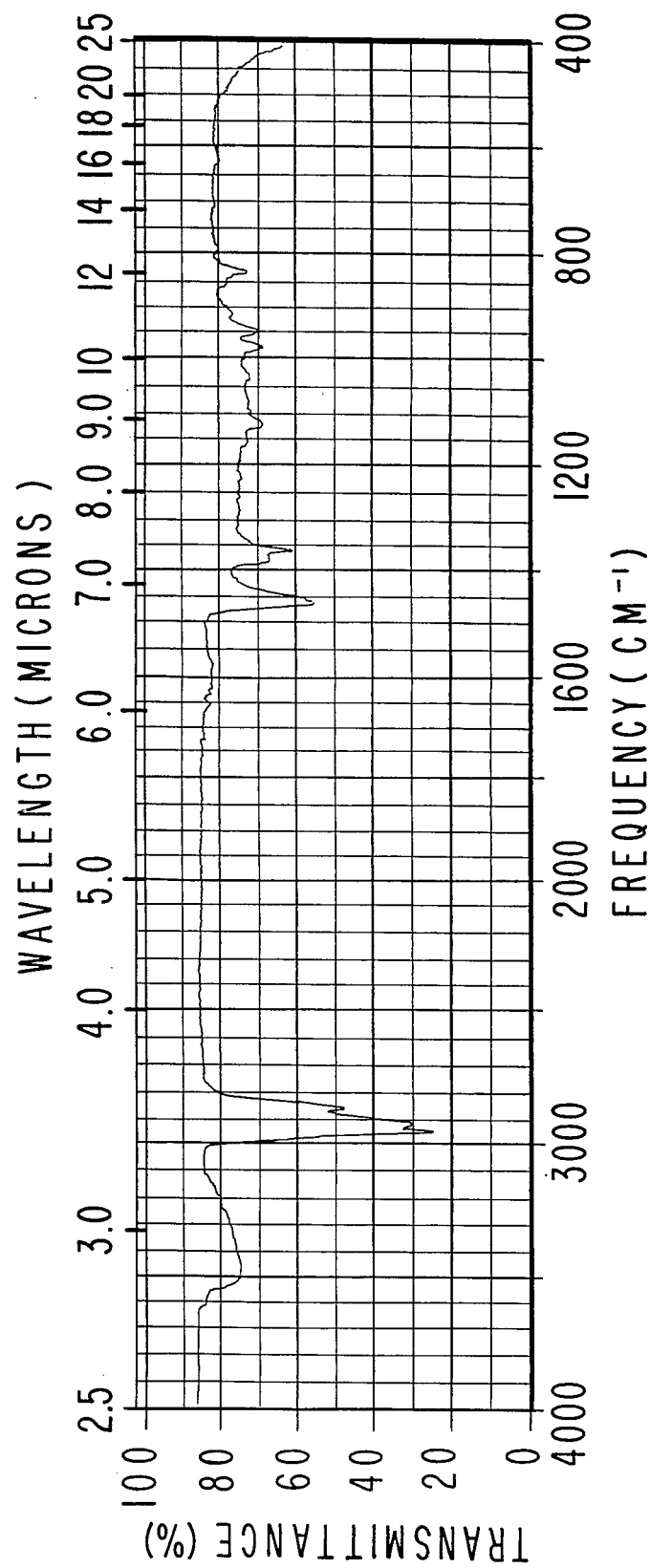

FIG. 36 is the infra-red spectrum for the compound having the structure:

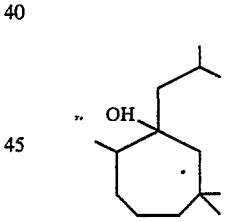

produced according to Example XII.

Figure 37:
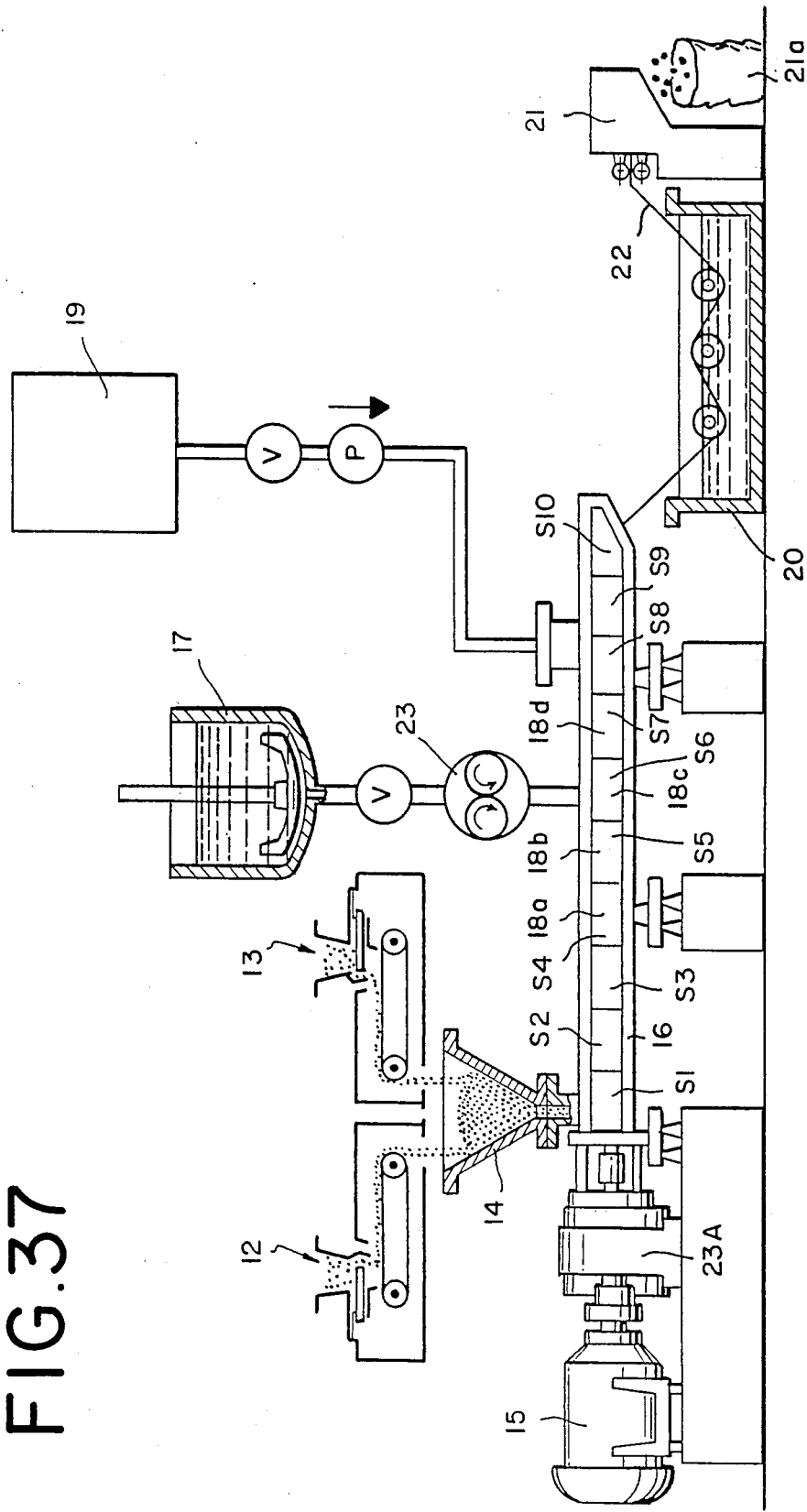

FIG. 37 is a schematic cut-away elevation diagram of the extrusion and pelletizing apparatus useful in producing perfumed polymers containing the polyalkyl-substituted oxocycloheptane derivatives of our invention during the operation of said apparatus.

DETAILED DESCRIPTION OF THE DRAWINGS

Figure 1:
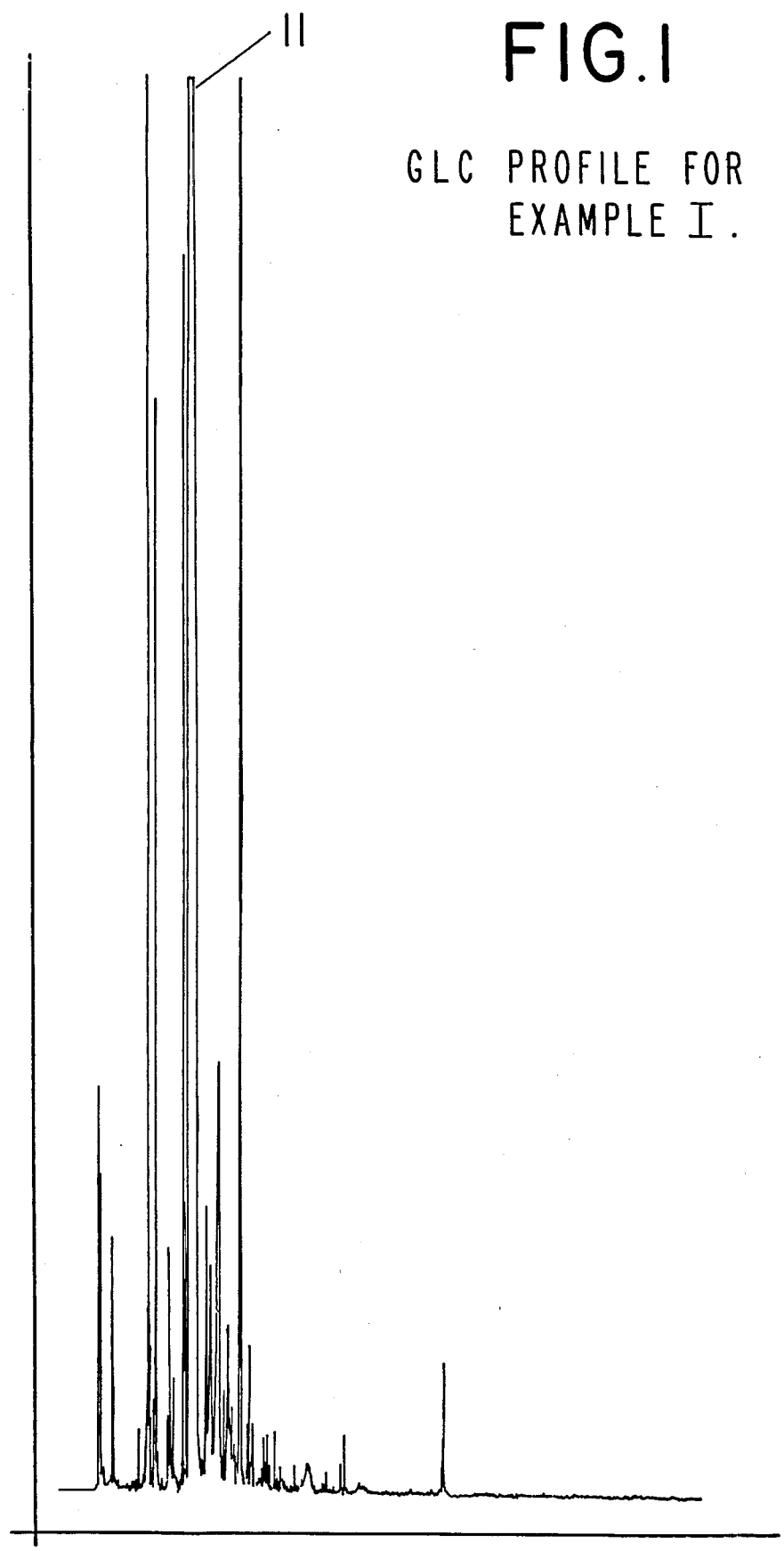
FIG. 1 is the GLC profile of the crude reaction product produced according to Example I containing the compounds having the structures.

FIG. 1 is the GLC profile for the crude reaction product produced according to Example I containing the compound having the structure:

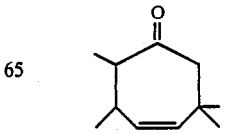

as well as the compound having the structure:

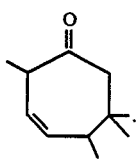

The peak indicated by reference numeral 11 is the peak for the compounds having the structures:

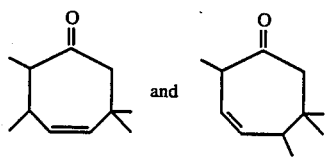

(Conditions: 30 m×0.32 mm SE-30 column programmed at 100°-180° C. at 8° C. per minute).

FIG. 4 is the GLC profile for the crude reaction product of Example II containing isomers of the compounds having the structures:

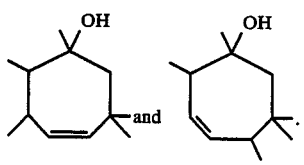

The peaks indicated by reference numerals 41, 42, 43, 44 and 45 are peaks for isomers (geometric isomers) of compounds having the structures:

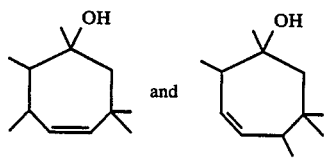

(Conditions: 30 m×0.32 mm supelcowax-10 (carbowax) column programmed at 100°-180° C. at 8° C. per minute).

FIG. 7 is the GLC profile for the crude reaction product of Example III containing the compound having the structure:

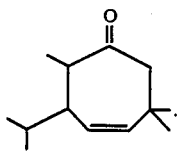

The peak indicated by reference numeral 71 is the peak for the compound having the structure:

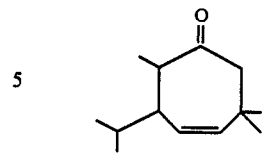

(Conditions: 30 m×0.32 mm supelcowax-10 (carbowax) column programmed at 100°-180° C. at 8° C. per minute).

FIG. 10 is the GLC profile for the crude reaction product of Example IV containing isomers of the compound having the structure:

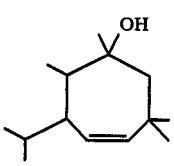

The peaks indicated by reference numerals 101 and 102 are peaks for geometric isomers of the compound having the structure:

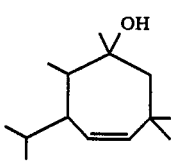

(Conditions: 30 m×0.32 mm supelcowax-10 (carbowax) column programmed at 100°-180° C. at 8° C. per minute).

FIG. 13 is the GLC profile for the crude reaction product of Example V containing the compound having the structure:

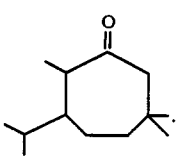

The peak indicated by reference numeral 131 is the peak for the compound having the structure:

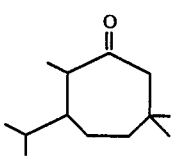

(Conditions: 30 m×0.32 mm supelcowax-10 (carbowax) column programmed at 100°-180° C. at 8° C. per minute).

FIG. 16 is the GLC profile for the crude reaction product of Example VI containing isomers of the compound having the structure:

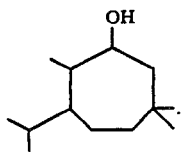

The peaks indicated by reference numerals 161 and 162 are peaks for the geometric isomers of the compound having the structure:

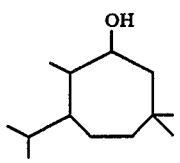

(Conditions: 30 m×0.32 mm supelcowax-10 (carbowax) column programmed at 100°-180° C. at 8° C. per minute).

FIG. 19 is the GLC profile for the crude reaction product of Example VII containing isomers of the compound having the structure:

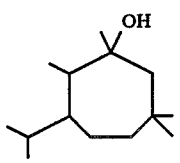

The peaks indicated by reference numerals 191 and 192 are peaks for geometric isomers of the compound having the structure:

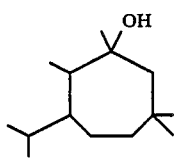

(Conditions: 30 m×0.32 mm supelcowax-10 (carbowax) column programmed at 100°-180° C. at 8° C. per minute).

FIG. 22 is the GLC profile for the crude reaction product of Example VIII containing the compound having the structure:

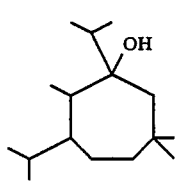

The peak indicated by reference numeral 221 is the peak for the compound having the structure:

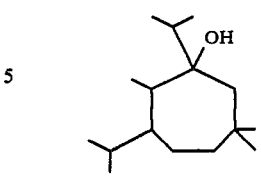

(Conditions: 30 m×0.32 mm supelcowax-10 (carbowax) column programmed at 100°-180° C. at 8° C. per minute).

FIG. 25 is the GLC profile for the crude reaction product of Example IX containing the compound having the structure:

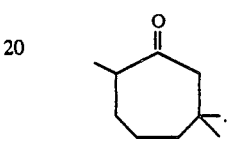

The peak indicated by reference numeral 251 is the peak for the compound having the structure:

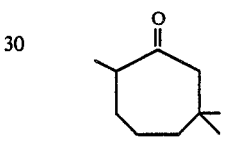

(Conditions: 30 m×0.32 mm supelcowax-10 (carbowax) column programmed at 100°-180° C. at 8° C. per minute).

FIG. 28 is the GLC profile for the crude reaction product produced according to Example X containing the compound having the structure:

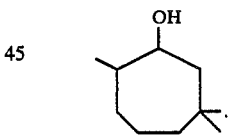

The peaks indicated by reference numerals 281 and 282 are peaks for geometric isomers of the compound having the structure:

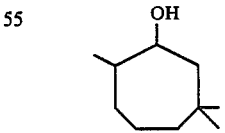

(Conditions: 30 m×0.32 mm supelcowax-10 (carbowax) column programmed at 100°-180° C. at 8° C. per minute).

FIG. 31 is the GLC profile for the crude reaction product produced according to Example XI containing geometric isomers of the compound having the structure:

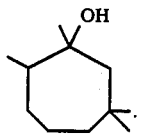

The peaks indicated by reference numerals 311 and 312 are peaks for geometric isomers of the compound having the structure:

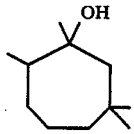

(Conditions: 30 m×0.32 mm supelcowax-10 (carbowax column programmed at 100°-180° C. at 8° C. per minute).

FIG. 34 is the GLC profile for the crude reaction product produced according to Example XII containing the compound having the structure:

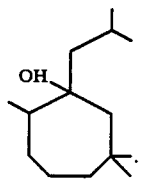

The peak indicated by reference numeral 341 is the peak for the compound having the structure:

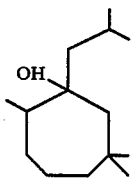

(Conditions: 30 m×0.32 mm supelcowax-10 (carbowax) column programmed at 100°-180° C. at 8° C. per minute).

FIG. 37 is a schematic cut-away elevation diagram of the extrusion and pelletizing apparatus useful in carrying out a process for forming perfumed polymers using the polyalkyl-substituted oxocycloheptane derivatives of our invention during the operation of said apparatus. Motor 15 drives the extruder screws located at 23A in barrel 16, the extruder being operated at temperatures in the range of about 150° C. up to about 250° C. At the beginning of the barrel resin at source 12 together with the processing aids at location 13 is added via addition funnel 14 into the extruder. Simultaneously (when the operation reaches "steady state"), at least one of the polyalkyl-substituted oxocycloheptane derivatives of our invention is added to the extruder at 1, 2 or more of barrel segments S-3, S-4, S-5, S-6, S-7 and S-8 of the extruder (which may be a twin screw or single screw extruder) at locations 18A, 18B, 18C and 18D, for example, by means of gear pump 23 from source 17. From source 19 into barrel segments S-5, S-6, S-7, S-8, S-9 and S-10, optionally, the gaseous or liquid blowing agents, e.g., nitrogen, carbon dioxide and the like as described, infra, are added simultaneously with the addition of at least one of the polyalkyl-substituted oxocycloheptane derivatives of our invention. The feed rate range of the resin is about 80-300 pounds per hour. The feed rate range of at least one of the polyalkyl-substituted oxocycloheptane derivatives of our invention is between 1 and 35% of the feed rate range of the resin. The blowing agent rate range (when the blowing agent is used) is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

THE INVENTION

The present invention provides polyalkyl-substituted oxocycloheptane derivatives defined according to the generic structure:

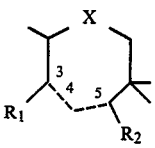

wherein X represents one of the moieties:

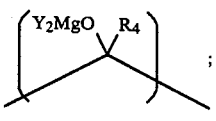

and

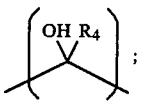

wherein one of the dashed lines is a carbon-carbon double bond and the other of the dashed lines is a carbon-carbon single bond; or both dashed lines are carbon-carbon single bonds; wherein $R_1$ and $R_2$ represents hydrogen or lower alkyl with the proviso that when the dashed line at the 4-5 position is a double bond, $R_2$ is hydrogen and when the dashed line at the 3-4 position is a double bond, $R_1$ is hydrogen; wherein $R_4$ represents $C_1$-$C_4$ lower alkyl; and wherein Y represents chloro or bromo. The present invention also provides processes for preparing such polyalkyl-substituted oxocycloheptane derivatives using as a starting material the commercially available cyclic ketone having the structure:

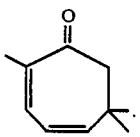

Thus, reaction of the compound having the structure:

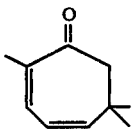

with Grignard reagents gives rise to ring alkylation of the ring and elimination of one of the two double bonds while causing the ketone moiety to remain intact. The thus-produced unsaturated cyclic ketone may then be used "as is" for its perfumery properties or may be further reacted with either hydrogen (to remove the remaining carbon-carbon double bond) or with an additional Grignard reagent to cause the formation of a tertiary alcohol.

It has been found that polyalkyl-substituted oxocycloheptane derivatives of our invention having the formula:

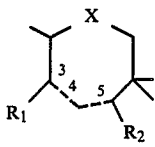

wherein X represents a moiety selected from the group consisting of:

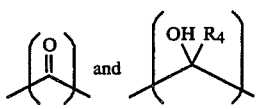

and wherein one of the dashed lines is a carbon-carbon double bond and the other of the dashed line is a carbon-carbon single bond or both dashed lines are carbon-carbon single bonds; wherein $R_1$ and $R_2$ represent hydrogen or lower alkyl; wherein $R_4$ represents hydrogen or lower alkyl; with the proviso that when the dashed line at the 4-5 position is a double bond $R_2$ is hydrogen and when the dashed line at the 3-4 position is a double bond, $R_1$ is hydrogen possess fruity, fresh, minty, earthy, camphoraceous, sweaty, animalic, woody, patchouli-like, rooty, seedy, piney, cedarwood-like, herbaceous, dried fruit and tobacco-like aromas with fruity, dried fruit, rose, orris-like and pennyroyal-like topnotes and with fruity and ionone-like undertones. The polyalkyl-substituted oxocycloheptane derivatives of our invention taken alone or in combination with one another are olfactory agents and can be incorporated into a wide variety of compositions which will be enhanced by their fruity, fresh, minty, earthy, camphoraceous, sweaty, animalic, woody, patchouli-like, rooty, seedy, piney, cedarwood-like, herbaceous, dried fruit and tobacco-like notes. The polyalkyl-substituted oxocycloheptane derivatives of our invention can individually or in combination be added to perfume compositions in their pure form or they can be added in mixtures of materials in fragrance imparting compositions to provide a desired fragrance character to the finished perfume material. The perfume and fragrance compositions obtained according to our invention are suitable in a wide variety of perfumed articles and can also be used to enhance, modify or reenforce natural fragrance materials. It will thus be appreciated that the polyalkyl-substituted oxocycloheptane derivatives of our invention are useful as olfactory agents and fragrances taken alone or in combination with one another.

The polyalkyl-substituted oxocycloheptane derivatives of our invention as stated, supra, are prepared using as a starting material the commercially available eucarvone having the structure:

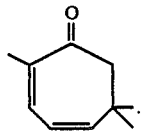

A first process for preparing products of our invention involves reacting the eucarvone having the structure:

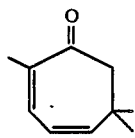

with a Grignard reagent in the formula $R_1$, MgY' wherein $R_1$ represents $C_1$–$C_4$ lower alkyl and Y' represents chloro or bromo according to the reaction:

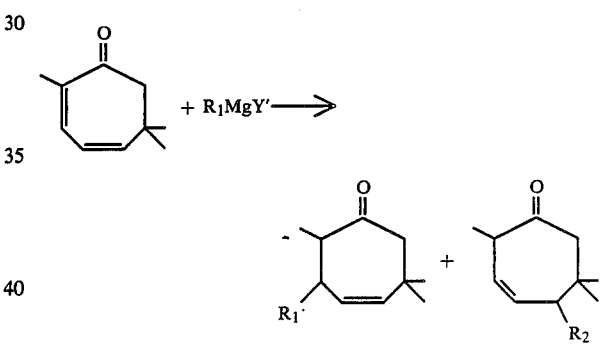

in the presence of a cuprous chloride catalyst at a temperature in the range of from about 0° C. down to about −10° C. and in the presence of an inert solvent, for example, tetrahydrofuran. The mole ratio of Grignard reagent to eucarvone is in the range of from about 1.0:1.0 up to about 1.5:1.0 (Grignard reagent:eucarvone). The mole ratio of catalyst to eucarvone may vary from about 0.005:1 up to about 0.02:1 with a preferred mole ratio of catalyst being 0.01:1.

The resulting product will contain two compounds, each compound having a number of geometric isomers, the compounds having the generic structures:

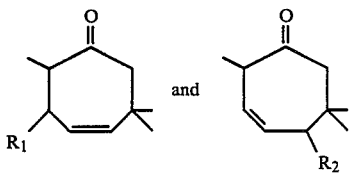

wherein $R_1$ and $R_2$ are the same and each represents $C_1$–$C_4$ lower alkyl. The preferred reaction temperature is between about 0° C. and −5° C. The preferred reaction time is between about one hour and about five hours. At the end of the reaction, the reaction mass is extracted with a solvent such as methylene dichloride and the resulting extract is evaporated and fractionally distilled to yield the desired product.

If the reaction:

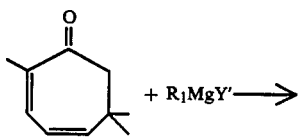

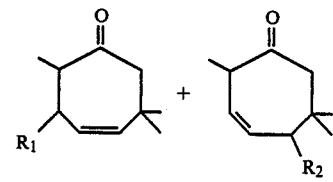

is attempted to be run at reaction temperatures greater than 0° C., e.g., at room temperature or even higher, e.g., at 35° C., the reaction:

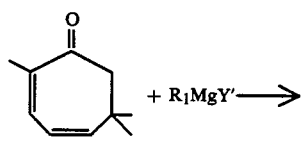

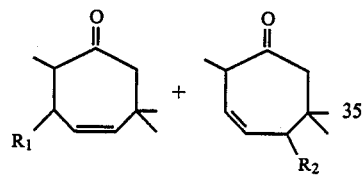

will take place to some extent; however a side reaction will also occur to an appreciable extent, to wit:

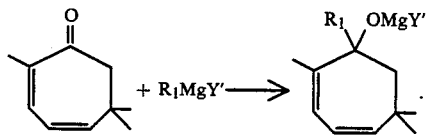

The resulting product having the structure:

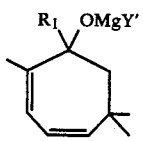

necessarily must be hydrolyzed and acetic acid is used for this purpose thereby causing the hydrolysis reaction to occur, to wit:

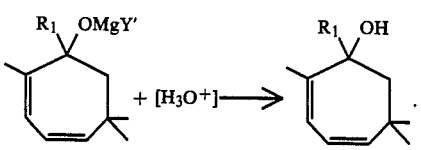

The resulting product having the structure:

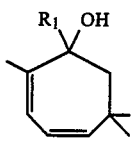

(not part of the genus of the instant invention) is then further reacted according to the reaction:

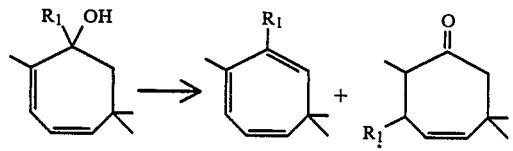

using a strong protonic acid catalyst, e.g., paratoluene sulfonic acid and the mixture of compounds having the structures:

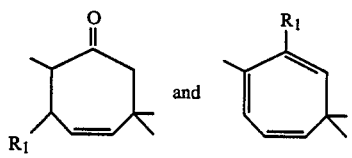

is separated by means of fractional distillation.

The foregoing reaction,

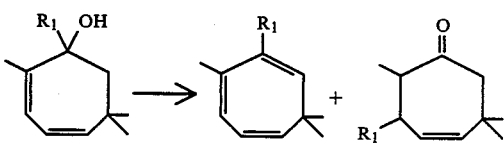

takes place in the presence of an inert solvent, preferably n-hexane. The mole ratio of catalyst, for example, paratoluene sulfonic acid, to reactant is preferably 0.01:1. The concentration of reactant in solvent is approximately from 0.25 grams per ml up to about 0.5 grams per ml.

Thus, broadly, the reaction:

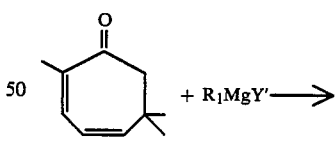

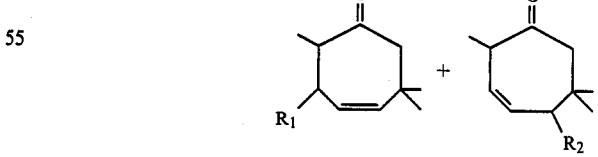

can take place at a temperature of from between about −10° C. up to about +40° C. but at the higher temperatures the biproduct formation becomes a problem and the resulting biproducts must be converted to useable perfumery products.

The ketone products resulting from the foregoing reactions may be used "as is" or they may be converted to other useful perfumery products.

Thus, the resulting products may be reacted with an additional Grignard reagent, e.g., $R_4MgY''$ wherein $Y''$ is chloro or bromo and $R_4$ is $C_1$–$C_4$ lower alkyl according to the reactions:

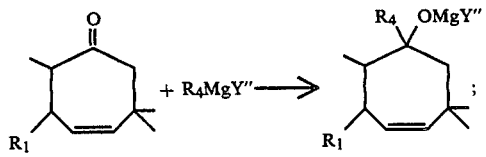

and followed by:

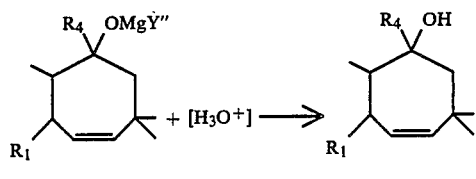

and

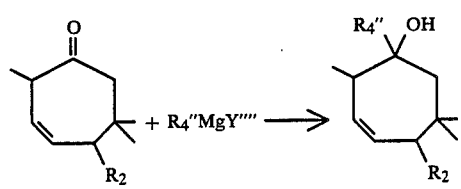

followed by:

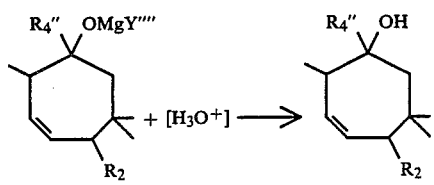

wherein $Y''''$ also represents chloro or bromo and $R_4''$ represents $C_1$–$C_4$ alkyl.

The resulting tertiary alcohols having the structures:

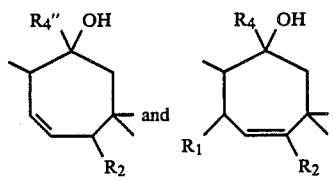

are extracted and separated from the reaction mass by means of fractional distillation.

The reaction to form the organometallic salts takes place at room temperature, e.g., from about 20° C. up to about 30° C. at atmospheric pressure in the presence of an inert solvent having a high vapor pressure at room temperature, e.g., tetrahydrofuran and/or diethyl ether.

The mole ratio of Grignard reagent:ketone may vary from about 1:1 up to 2:1 (Grignard reagent:ketone) with a preferred mole ratio of Grignard reagent:ketone being about 1.2:1.0. The reaction time may vary from about 0.25 hours up to about 1 hour with a preferred reaction time being about 0.5 hours.

The resulting product is a mixture of geometric isomers as described in more detail, infra.

The resulting mixture of products which are organometallic salts are then hydrolyzed in the presence of weak acid such as acetic acid diluted with water. The hydrolysis takes place at a temperature in the range of from about +10° C. down to about −20° C. with a preferred hydrolysis reaction temperature being approximately −10°—−20° C. The preferred acid hydrolysis reagent is 15% aqueous acetic acid.

The resulting reaction mass is then neutralized, and extracted into a solvent such as methylene dichloride. The resulting extract is evaporated and fractionally distilled yielding a mixture of tertiary alcohols and further, a mixture of geometric isomers of tertiary alcohols.

The resulting ketone, e.g., ketones of the generic structure:

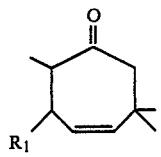

may be also reduced to their corresponding ring-saturated ketones defined according to the structure:

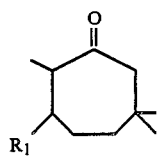

according to the reaction:

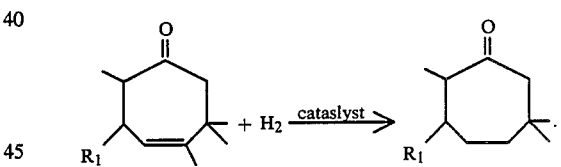

This reaction takes place in the presence of a solvent such as isopropyl alcohol. The temperature of reaction is approximately room temperature; between about 20° C. up to about 30° C. The pressure of reaction is between about 150 up to about 250 psig. The catalyst used is 10% palladium on carbon or 10% palladium on calcium carbonate. The concentration of ketone having the structure:

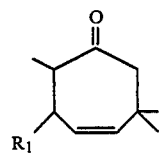

in the reaction mass is from about 0.2 grams per ml down to about 0.05 grams per ml. The ratio (weight ratio) of catalyst (including support) to ketone having the structure:

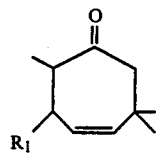

is from about 0.05:1 up to about 0.2:1 with a preferred weight ratio of 0.1:1.

The resulting product having the structure:

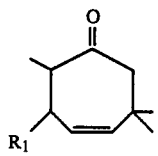

may be used "as is" for its organoleptic properties (after fractionally distilling same from the reaction mass) or it may be further reacted with a Grignard reagent to form ultimately a tertiary alcohol according to the reactions:

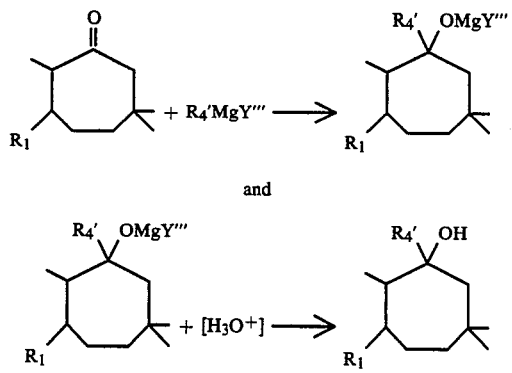

wherein in the Grignard reagent $R_4'MgY'''$, $R_4'$ represents $C_1$-$C_4$ lower alkyl and $Y'''$ represents chloro or bromo.

The conditions for the Grignard reaction to form the organometallic salt are the same as previously set forth Grignard reagents whereby tertiary alcohols are formed. Thus, the mole ratio of Grignard reagent to ketone having the structure:

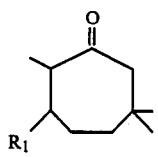

may vary from about 1.5:1 down to about 1:1 with a preferred mole ratio of 1.2:1. The reaction takes place in a solvent which is inert to the reactants and to the reaction products, to wit: tetrohydrofuran and/or diethyl ether. The temperature of the reaction to form the organometallic compound may vary from about 20° C. up to about 30° C. The time of reaction may vary from about 0.25 hours up to about 1 hour with a time of reaction of about 0.5 hours being preferred. The resulting product is an organometallic salt defined according to the structure:

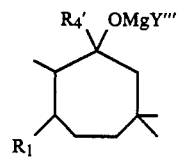

where $R_1$, $R_4'$ and $Y'''$ are defined, supra. At the end of this reaction to form the organometallic salt, the reaction mass is treated with weak acid such as dilute acetic acid at a temperature of between about $-5°$ C. and about $+5°$ C. Thus, the reaction:

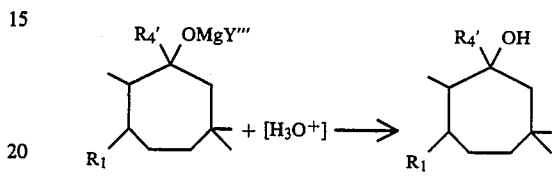

takes place.

At the end of this reaction the reaction mass is extracted with such materials as methylene chloride and the organic layer is then washed and neutralized with such materials as dilute aqueous sodium bicarbonate. The organic phase is then fractionally distilled yielding compounds defined according to the generic structure:

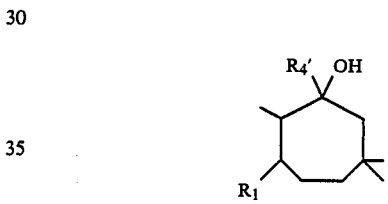

In addition, the resulting reaction product defined according to the structure:

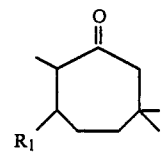

may be further reduced as with an alkali metal borohydride according to the reaction:

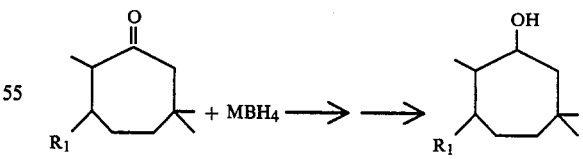

(wherein M represents alkali metal, e.g., sodium, potassium or lithium).

The reaction takes place in the presence of a solvent such as anhydrous ethyl alcohol. The temperature of reaction is at approximately ambient temperature, from about 15° C. up to about 30° C. The mole ratio of alkali metal borohydride to ketone may vary from about 1.5:0.5 down to about 1:1 with a preferred mole ratio of alkali metal borohydride:ketone being about 1:1. The concentration of the ketone in the reaction mass may vary from about 0.6 grams per ml up to about 1 gram per ml with a preferred concentration of ketone of about 0.2 grams per ml.

At the end of the reaction the reaction mass is neutralized with a weak acid such as dilute hydrochloric acid. The reaction mass is then extracted with an extracting agent such as methylene dichloride and washed with such materials as dilute aqueous sodium bicarbonate and then fractionally distilled.

The ketone having the structure:

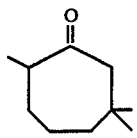

may be prepared from eucarvone having the structure:

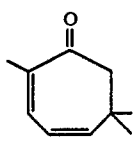

also by means of hydrogenation using a palladium on carbon catalyst according to the reaction:

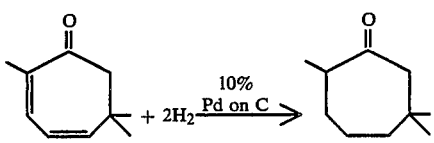

This reaction takes place in a solvent such as isopropyl alcohol at temperatures in the range of from about 15° C. up to about 35° C. and at pressures in the range of from about 50 psig up to about 250 psig with a preferred pressure range of 200–205 psig. The time of reaction is approximately 0.5 hours but may vary up to about one hour. The catalyst which may be used is 10% palladium on carbon or 10% palladium on calcium carbonate. The concentration of eucarvone in the reaction mass is preferred to be from about 3 moles per liter up to about 5 moles per liter. The percentage of catalyst in the reaction mass (including support) is from about 0.3% up to about 1% with a preferred percentage of catalyst being about 0.4%. The resulting product having the structure:

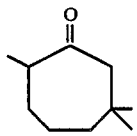

may be further reduced to its corresponding alcohol having the structure:

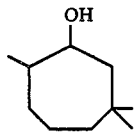

using an alkali metal borohydride or it may be further reacted with a Grignard reagent or the compound having the structure:

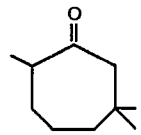

may be used "as is" for its organoleptic properties.

In reducing the compound having the structure:

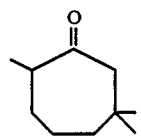

using an alkali metal boro hydride the reaction taking place is exemplified as follows:

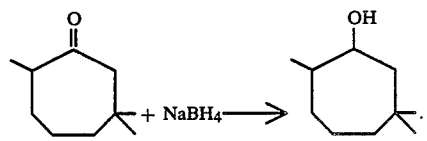

In place of the sodium borohydride used as set forth in the above reaction other alkali metal borohydrides may be used including potassium borohydride and lithium borohydride. Thus, the reaction taking place is generically set forth, thusly:

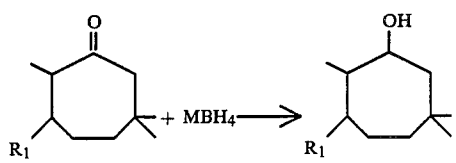

wherein $R_1$ represents hydrogen and M represents alkali metal. The reaction conditions for the reaction of the ring-saturated ketone with the alkali metal borohydride are set forth, supra.

In addition, the resulting ketone having the structure:

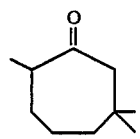

may be reacted with a Grignard reagent in order to ultimately form a tertiary alcohol in accordance with the reaction sequence:

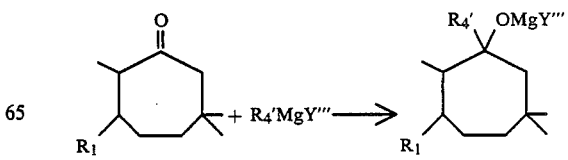

and

-continued

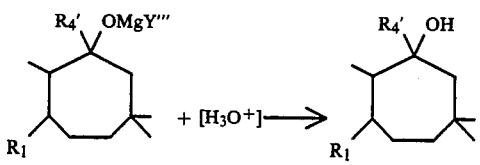

wherein $R_1$ is hydrogen and $R_4'$ and $Y''$ have been defined, supra. The reaction conditions in carrying out the aforementioned Grignard reaction and the resulting hydrolysis reaction are the same as those for similar Grignard reactions and subsequent hydrolysis reactions set forth, supra.

The resulting tertiary alcohols produced are in the form of a number of geometric isomers, for example, those having the structures:

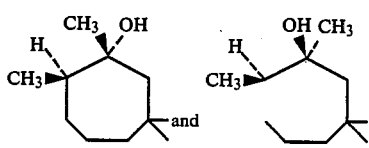

when methyl magnesium chloride or methyl magnesium bromide is used as the reacting Grignard reagent.

The following polyalkyl-substituted oxocycloheptane derivatives are examples of those which can be produced using the aforementioned processes and the following table sets forth the perfumery characteristics of said polyalkyl-substituted oxocycloheptane derivatives:

TABLE I

| Structure of Compound | Perfumery Property |
|---|---|
| Compounds having the structures:<br>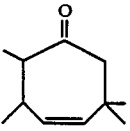<br>and<br>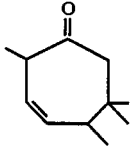<br>(mixture) produced according to Example I. | A fruity (apple), minty aroma with dried fruit and rose topnotes. |
| Mixture of compounds having the structures:<br>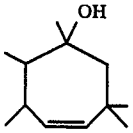<br>and<br>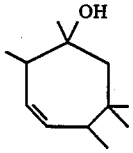<br>produced according to Example II | An earthy, camphoraceous, sweaty, animalic, woody and patchouli-like aroma. |
| Compound having the structure:<br>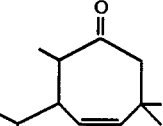<br>produced according to Example III. | A woody, rooty and seedy aroma with orris-like topnotes. |
| Compound having the structure:<br>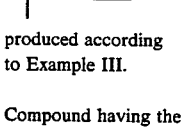<br>produced according to Example IV. | A woody, fruity, floral (violet) aroma with rose and dried fruit topnotes. |
| Compound having the structure:<br>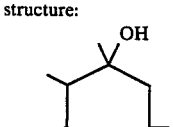<br>produced according to Example V. | A woody and piney aroma with fruity undertones. |
| Compound having the structure:<br>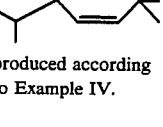<br>produced according to Example VI. | A woody, fruity and cedarwood aroma. |
| Compound having the structure:<br>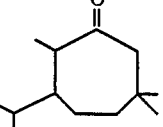<br>produced according to Example VII. | A woody, fruity and camphoraceous aroma. |
| Compound having the structure:<br>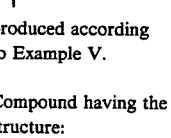<br>produced according to Example VIII. | A fresh and minty aroma. |

TABLE I-continued

| Structure of Compound | Perfumery Property |
|---|---|
| Compound having the structure: 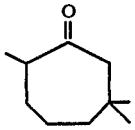 produced according to Example IX. | A minty (peppermint) and herbaceous aroma with pennyroyal-like topnotes. |
| Compound having the structure: 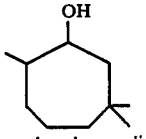 produced according to Example X. | A dried fruit (figs, dates), tobacco-like, minty, camphoraceous and earthy aroma with ionone-like undertones. |
| Compound having the structure: 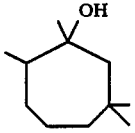 produced according to Example XI. | A patchouli-like, earthy, rooty and camphoraceous aroma profile. |
| Compound having the structure: 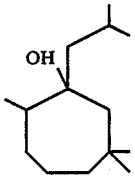 produced according to Example XII. | A woody and camphoraceous aroma with fruity topnotes. |

One or more polyalkyl-substituted oxocycloheptane derivatives prepared in accordance with the processes of our invention as set forth, supra, and in the examples, infra, and one or more auxiliary perfume ingredients including, for example, alcohols other than those of our invention, aldehydes, ketones other than those of our invention, terpenic hydrocarbons, nitriles, esters, lactones, natural essential oils and synthetic essential oils may be admixed so that the combined odors of the individual components produce a pleasant and desired fragrance particularly and preferably rosy, minty, woody and animalic/musky fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, one or more polyalkyl-substituted oxocycloheptane derivatives prepared in accordance with the process of our invention, can be used to alter, modify or enhance the aroma characteristics of a perfume composition, for example, by utilizing or moderating the olfactory reaction contributed by another ingredient in the composition.

The amount of one or more of the polyalkyl-substituted oxocycloheptane derivatives prepared in accordance with the processes of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients present in the composition, their amounts and the effects which are desired. It has been found that perfume compositions containing as little as 0.01% of one or more of the polyalkyl-substituted oxocycloheptane derivatives prepared in accordance the processes of our invention and less than 70% of one or more of the polyalkyl-substituted oxocycloheptane derivatives prepared in accordance with the processes of our invention or even less (e.g., 0.005%) can be used to impart fresh, fruity, minty, earthy, camphoraceous, sweaty, animalic, woody, patchouli-like, rooty, seedy, piney, cedarwood-like, herbaceous, dried fruit and tobacco-like aroma nuances with fruity, dried fruit, rose, orris-like and pennyroyal-like topnotes and with fruity and ionone-like undertones to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on consideration of cost, nature of the end product, the effect desired on the finished product and the particular fragrance sought.

One or more of the polyalkyl-substituted oxocycloheptane derivatives prepared in accordance with the processes of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture to produce said perfumed polymers. When used as (an) olfactory component(s) as little as 0.2% of one or more of the polyalkyl-substituted oxocycloheptane derivatives prepared in accordance with the processes of our invention will suffice to impart an intense fruity, fresh, minty, earthy, camphoraceous, sweaty, animalic, woody, patchouli-like, rooty, seedy, piney, cedarwood-like, herbaceous, dried fruit and tobacco-like aromas with fruity, dried fruit, rose, orris-like and pennyroyal-like topnotes and with fruity and ionone-like undertones to rosy, woody, minty or musky/animalic formulations.

Generally, no more than 6% of one or more of the polyalkyl-substituted oxocycloheptane derivatives of our invention based on the ultimate end product is required in the perfumed article composition. Accordingly, the range of polyalkyl-substituted oxocycloheptane derivatives in the perfumed article is from about 0.2% by weight of the polyalkyl-substituted oxocycloheptane derivatives up to about 6% by weight of the polyalkyl-substituted oxocycloheptane derivatives based on the perfumed article.

In addition, the perfume composition or fragrance composition of our invention can contain a vehicle or carrier for one or more polyalkyl-substituted oxocycloheptane derivatives prepared in accordance with the processes of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation; or such as a urea-formaldehyde polymer forming a capsule shell around a liquid perfume center).

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at lease one of the structures:

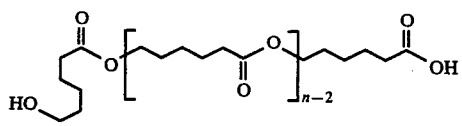

and/or

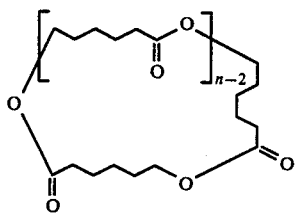

wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$ being the average number of repeating monomeric units for the epsilon polycaprolactone polymer. The perfumed material's release rate from such polymer mixture is close to "zero order". As a general rule, the release rate in a polymeric matrix is proportional to $t-\frac{1}{2}$ until about 60% of the functional fluid is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods Theory, and Applications" (cited, supra, the amount of perfume composition released in proportional to time as long as the concentration of perfume material present, e.g., the polyalkyl-substituted oxocycloheptane derivatives of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release constant (zero order) as long as the surface area does not change during the erosion process. This is the case with the polymers containing the polyalkyl-substituted oxocycloheptane derivatives of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxbenzenes such hydroquinone or compounds having the formula:

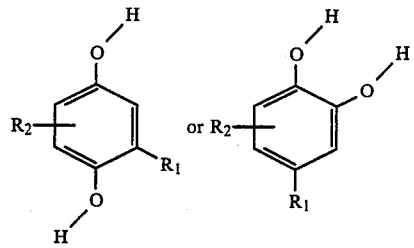

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating the polyalkyl-substituted oxocycloheptane derivatives of our invention or perfume compositions containing same into the polymers is set forth, supra, in the detailed description of the drawings and furthermore, may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, using U.S. Pat. No. 3,505,432, a first amount of liquid polyethylene-polyepsilon caprolactone polymer mixture (50:50) is mixed with one of the polyalkyl-substituted oxocycloheptane derivatives of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50(weight:weight)polyepsilon caprolactone, e.g., PCL-700:polyethylene in molten form is admixed with a high percentage of one of the polyalkyl-substituted oxocycloheptane derivatives of our invention and the mixture is solidified in the form of pellets or beads. These pellets or beads thus contain a high percentage of polyalkyl-substituted oxocycloheptane derivatives (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention at least one of the polyalkyl-substituted oxocycloheptane derivatives of our invention is added to the polymer in a large closed container or drum which is maintained under controlled temperature conditions while the polymer in a melted condition is mixed with at least one of the polyalkyl-substituted oxocycloheptane derivatives under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the polyalkyl-substituted oxocycloheptane derivatives of our invention is permitted to drip through the orifices onto a continuously moving, cooled conveyor upon which the polymer containing at least one of the polyalkyl-substituted oxocycloheptane derivatives of our invention solidifies into small size pellets with the perfume imprisoned therein. The apparatus useful in conjunction with this process advantageously includes a conveyor of a material which will not adhere to the polymer which contains at least one of the polyalkyl-substituted oxocycloheptane derivatives of our invention.

In order that the droplets form into uniform pellets or beads, the conveyor is continuously washed with a liquid such as water to maintain the surface relatively cool. The pellets are delivered by the conveyor into a container and packaged for shipment.

The following Examples I–XII serve to illustrate processes for preparing the polyalkyl-substituted oxocycloheptane derivatives of our invention. The examples following Example XII are illustrative of the organoleptic utilities of the polyalkyl-substituted oxocycloheptane derivatives of our invention. All parts and percentages given herein are by weight unless otherwise specified.

EXAMPLE A

PREPARATION OF EUCARVONE

Reaction:

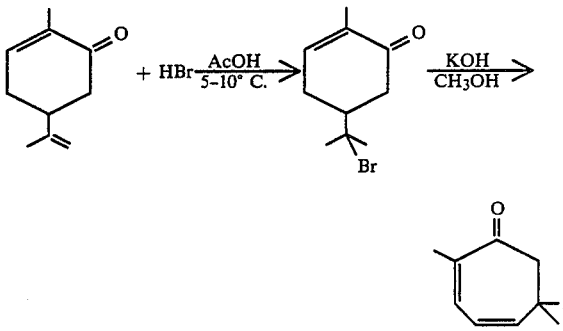

Into a 3 liter three neck round bottom flask equipped with mechanical stirrer, Y-Tube, thermometer, hydrogen bromide outlet to Primol ®Bubbler; hydrogen bromide inlet to bubbler to empty trap to hydrogen bromide cylinder; wet ice bath; dry ice/isopropyl alcohol bath; and addition funnel is placed 1,350 ml of glacial acetic acid. Under a nitrogen blanket, the acetic acid is saturated with hydrogen bromide gas. Thus, over a period of 4 hours while maintaining the reaction temperature at 15°–25° C., hydrogen bromide gas is bubbled into the acetic acid.

The reaction mass is then cooled to 5°–10° C. using the dry ice/isopropyl alcohol bath and the hydrogen bromide inlet is replaced with an addition funnel. Over a period of 1 hour while maintaining the reaction temperature at 0°–15° C., 682 grams (4.55 moles) of carvone is added to the reaction mass.

The reaction mass is then placed in a 12 liter separatory funnel containing 7 liters of water and the resulting mixture is stirred for a period of 5 minutes.

The reaction mass then separates into two layers, an organic phase and an aqueous phase. The aqueous phase is extracted with 500 ml toluene. The organic layer is combined with the toluene extract and washed with two 1200 ml portions of water; and then dried over anhydrous sodium sulfate.

Into a 5 liter three neck flask equipped with Y tube, condenser, thermometer, addition funnel, ice water bath and heating mantle is placed 491 grams of potassium hydroxide and 1860 ml anhydrous methyl alcohol. Over a period of 1 hour, dropwise, the resulting carvone hydrobromide produced above is added to the reaction mass while maintaining the temperature at 24°–28° C.

To a 12 liter separatory funnel, 8 liters of ice/water and 122 ml sulfuric acid (concentrated) is placed. With stirring, the carvone hydrobromide reaction mixture is added to the reaction mass. 500 ml Toluene is then added to the reaction mass and the reaction mass is continued to be stirred. The reaction mass now exists in two phases; an aqueous phase and an organic phase. The aqueous phase is discarded and the organic phase is washed with 2 liters of water. The reaction mass is then added to a mixture of 200 ml saturated sodium bicarbonate and 1000 ml water. The resulting product has the structure:

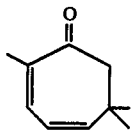

(crude reaction mass).

The reaction mass is then evaporated (toluene is removed at 55° C. and 150–120 mm/Hg pressure).

The reaction mass is then fractionally distilled on a 12" Vigreux column yielding the following fractions:

| Fraction No. | Vapor Temp. (°C.) | Liquid Temp. (°C.) | Vacuum mm/Hg. Pressure | Weight of Fraction (g) |
|---|---|---|---|---|
| 1 | 55/55 | 64/67 | 150/120 | 150.1 |
| 2 | 55 | 69 | 120 | 366.4 |
| 3 | 56 | 75 | 100 | 154.4 |
| 4 | 53/55 | 75/76 | 100/95 | 149.8 |
| 5 | 45 | 93 | 25 | 161.9 |
| 6 | 61 | 78 | 3.2 | 10.2 |
| 7 | 62 | 78 | 3.2 | 131.1 |
| 8 | 62 | 79 | 3.2 | 169.4 |
| 9 | 63 | 82 | 3.2 | 75.2 |
| 10 | 67 | 92 | 3.2 | 70.8 |
| 11 | 68 | 95 | 3.0 | 10.4 |

Fractions 6–10 are bulked for further reaction in Examples I–XII, infra.

The foregoing procedure is taken from Pinder "The Chemistry of The Terpenes", John Wiley & Sons Inc., 1960, at pages 72 and 73 (the text of which is incorporated herein by reference).

EXAMPLE I

PREPARATION OF MIXTURE OF 2,3,6,6-TETRAMETHYL-4-CYCLOHEPTENE-1-ONE AND 1,4,5,5-TETRAMETHYL-3-CYCLOHEPTENE-1-ONE

Reaction:

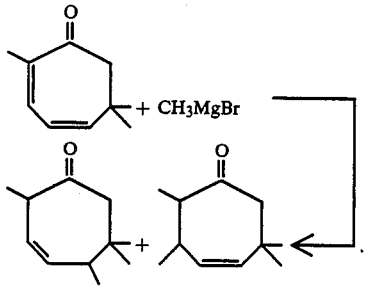

Into a 500 ml 3 neck flask equipped with mechanical stirrer, thermometer, nitrogen blanket apparatus, addition funnel and dry ice/isopropyl alcohol cooling bath is placed, under a nitrogen blanket 56 ml of methyl magnesium bromide (concentration: 2.85 molar in diethyl ether) and 56 ml of tetrahydrofuran (total moles of methyl magnesium bromide: 0.16).

The resulting mixture is cooled to +5° C.

While maintaining the pot temperature at +5° C. 0.13 grams of anhydrous cuprous chloride is added to the reaction mass with stirring. The reaction mass is then cooled to between 0° C. and −5° C.

While maintaining the reaction mass at a temperature of between 0° and −5° C., over a period of one hour, a mixture of 20 grams (0.1333 moles) of eucarvone having the structure:

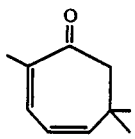

and 10 ml tetrahydrofuran is added to the reaction mass with stirring.

The reaction mass is then stirred for an additional 15 minutes at −2° C.−−3° C.

The reaction mass, while being maintained at −2° C., is admixed with 70.4 grams of 15% acetic acid.

500 ml Water is added to the reaction mass with stirring. The reaction mass is then extracted with one 200 ml portion of methylene dichloride. The reaction mass now exists in two phases; an aqueous phase and an organic phase. The organic phase is separated from the aqueous phase. The organic phase is washed with:

(a) one 300 ml portion of water;
(b) one 200 ml portion of 3.5% aqueous sodium bicarbonate; and
(c) one 200 ml portion of water.

The organic phase is then dried and filtered and then concentrated to a weight of 22.2 grams.

FIG. 1 is the GLC profile for the crude reaction product. (Conditions: 30 m×0.32 mm SE-30 column programmed at 100°–180° C. at 8° C. per minute). The peak indicated by reference numeral 11 is the peak for the mixture of the compounds having the structures:

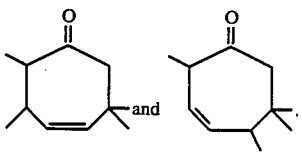

Two additional GLC traps are taken from the crude reaction product. A first trap contains 60% of the compound having the structure:

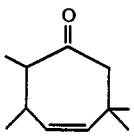

and 40% of the compound having the structure:

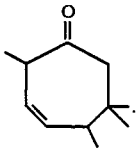

A second trap using carbowax yields 47% of the compound having the structure:

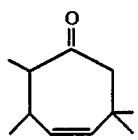

and 53% of the compound having the structure:

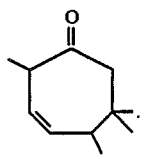

The resulting product is fractionally distilled yielding the following fractions:

| Fraction No. | Vapor Temp. (°C.) | Liquid Temp. (°C.) | Vacuum mm/Hg. Pressure | Weight of Fraction (g) |
|---|---|---|---|---|
| 1 | 70/95 | 77.5/78 | 2.7/2.7 | 2.0 |
| 2 | 70 | 78.5 | 2.75 | 1.5 |
| 3 | 71 | 79 | 2.85 | 2.5 |
| 4 | 71 | 80 | 2.9 | 2.8 |
| 5 | 72 | 86 | 3.0 | 4.4 |
| 6 | 72 | 98 | 3.0 | 2.8 |
| 7 | 74 | 110 | 3.0 | 0.8 |
| 8 | 80 | 139 | 3.0 | 1.0. |

Fractions 2–6 are bulked. Fraction 2–6 have a fruity (apple), minty aroma with dried fruit and rose topnotes.

FIG. 2 is the NMR spectrum for the mixture of compounds of bulked fractions 2–6 having the structures:

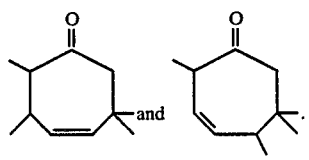

FIG. 3 is the infra-red spectrum for the mixture of compounds having the structures:

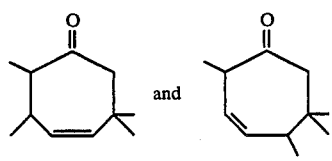

of bulked fractions 2–6 of the foregoing distillation.

EXAMPLE II

PREPARATION OF MIXTURE OF 1,2,3,6,6-PENTAMETHYL-4-CYCLOHEPTENE-1-OL AND 1,2,5,6,6-PENTAMETHYL-3-CYCLOHEPTENE-1-OL

Reaction:

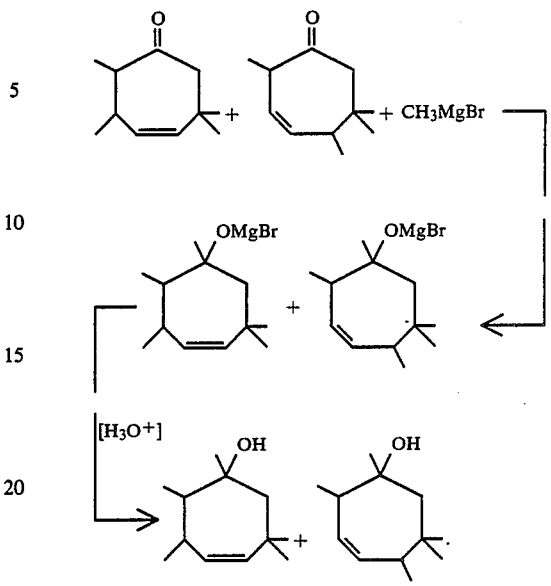

Into a 25 ml Erlenmeyer flask equipped with magnetic stirrer and nitrogen blanket apparatus with cold water bath is placed a mixture of 2.5 ml of a 2.85 molar solution of methyl magnesium bromide in diethyl ether (0.0072 moles of methyl magnesium bromide) and 3 ml of tetrahydrofuran. While maintaining the temperature at 10° C., over a period of 3 minutes 1.0 grams of a mixture of the ketones of bulked fractions 2–6 produced according to Example I (having the structures:

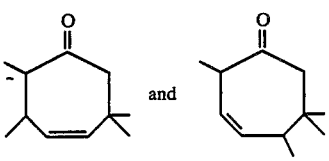

in 1 ml of tetrahydrofuran (0.006 moles of ketones) is added dropwise with stirring to the reaction mass. The reaction mass is then stirred at 0°–10° C. for a period of 5 minutes.

At this point in time the mixture of organometallic salts having the structures:

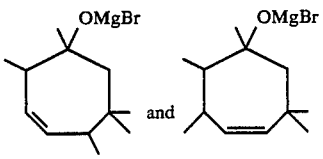

are produced.

Over a period of 10 minutes, 15% aqueous acetic acid (10 ml) is added to the reaction mass. Over an additional period of 10 minutes while maintianing the reaction mass at 5° C., 10 ml of water is added. The reaction mixture is then extracted with 15 ml of methylene dichloride. The reaction mass now exists in two phases; an organic phase and an aqueous phase. The organic phase is separated from the aqueous phase. The organic phase is washed with:

(a) 10 ml water;

(b) 10 ml of a 5% aqueous sodium bicarbonate solution; and (c) 15 ml of water (to a pH of 7).

The resulting product is then dried over anhydrous sodium sulfate and concentrated on a rotary evaporator.

The resulting reaction products are trapped using preparative GLC apparatus. FIG. 4 is the GLC profile for the crude reaction product (Conditions: 30 m×0.32 mm supelcowax-10 [carbowax] column programmed at 100°–180° C. at 8° C. per minute). The peaks indicated by reference numerals 41, 42, 43, 44 and 45 are peaks for isomers of the compounds having the structures:

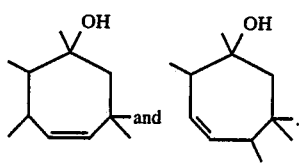

These compounds may be further separated from one another by further GLC trapping (preparative).

The bulked isomers of peaks 41, 42, 43, 44 and 45 have an earthy, camphoraceous, sweaty, animalic, woody and patchouli-like aroma profile.

FIG. 5 is the NMR spectrum for bulked peaks 41, 42, 43, 44 and 45 which contain isomers of the compounds having the structures:

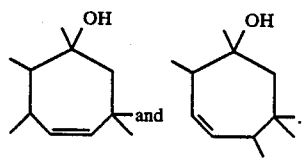

FIG. 6 is the infra-red spectrum for bulked peaks 41, 42, 43, 44 and 45 of FIG. 4 containing isomers of the compounds having the structures:

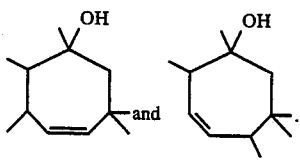

EXAMPLE III

PREPARATION OF 2,6,6-TRIMETHYL-3-(2'-PROPYL)-4-CYCLOHEPTENE-1-ONE

Reactions:

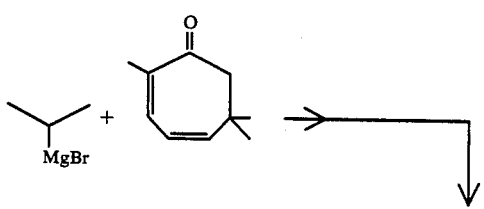

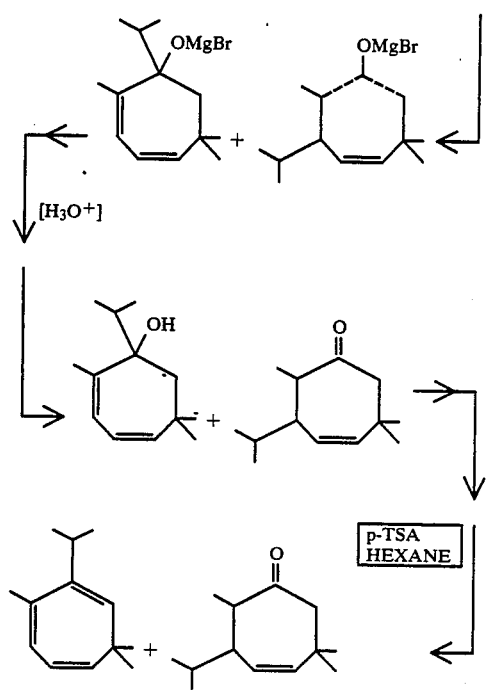

(wherein one of the dashed lines is a carbon-carbon double bond and the other of the dashed lines is a carbon-carbon single bond).

Into a 500 ml three neck reaction flask equipped with mechanical stirrer, Y tube with reflux condenser and thermometer; addition funnel with nitrogen inlet; and cold water bath are placed 5.8 grams (0.24 moles) of magnesium ribbon; 40 ml tetrahydrofuran, 2 ml of 2-bromopropane, 1 ml of 2.85 molar methyl magnesium bromide in diethyl ether and 1 crystal of iodine. While maintaining the temperature at 32°–38° C. over a period of 0.5 hours, 20.5 ml of 2-bromopropane and 60 ml of tetrahydrofuran is added to the reaction mass. The reaction mass is then stirred for a period of 10 minutes.

100 ml Tetrahydrofuran is then added to the reaction mass. 0.2 Grams of Cuprous chloride is the added to the reaction mass and the reaction mass is then cooled (using an isopropyl alcohol dry ice bath) to 0°–10° C. While maintaining the reaction temperature with stirring at 0°–10° C. over a period of 0.5 hours, 30 grams of eucarvone having the structure:

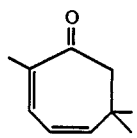

in 30 ml tetrahydrofuran is added to the reaction mass. The reaction mass is then stirred for a period of two hours at 0°–10° C.

At this point in time, the compounds having the structures:

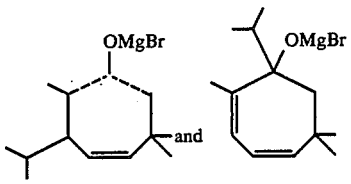 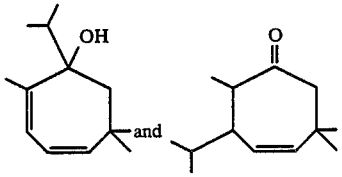

(wherein one of the dashed lines is a carbon-carbon double bond and the other of the dashed lines is a carbon-carbon single bond) have been produced.

173 Grams of 10% acetic acid is added to a 2 liter Erlenmeyer flask cooled in ice. The reaction mass is slowly added to the diluted acetic acid mixture in the Erlenmeyer flask with stirring. 500 ml of Water are then added to the reaction mass. The reaction mass is then extracted with one 300 ml portion of methylene dichloride. The reaction mass now exists in two phases; an organic phase and an aqueous phase. The organic phase is separated from the aqueous phase. The organic phase is washed as follows:

(a) one—500 ml portion of water;
(b) one—250 ml portion of 2% sodium bicarbonate; and
(c) one—500 ml portion of water.

The organic phase is then dried over anhydrous sodium sulfate and concentrated on a rotary evaporator to 35.5 grams.

The reaction product now contains two compounds having the structures:

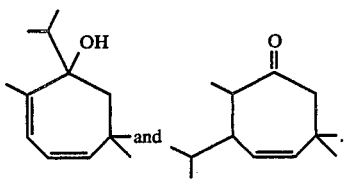

The resulting crude product is then fractionally distilled on a 6" Vigreux column yielding the following fractions:

| Fraction No. | Vapor Temp. (°C.) | Liquid Temp. (°C.) | Vacuum mm/Hg. Pressure | Weight of Fraction (g) |
|---|---|---|---|---|
| 1 | 74/76 | 82/83.5 | 1.5/1.5 | 1.3 |
| 2 | 77 | 85 | 1.5 | 2.5 |
| 3 | 79 | 87 | 1.5 | 1.0 |
| 4 | 63/73 | 88.5/90.5 | 1.5/1.5 | 1.5 |
| 5 | 79 | 92.5 | 1.5 | 1.3 |
| 6 | 79 | 92 | 1.5 | 1.2 |
| 7 | 79.5 | 92 | 1.5 | 1.5 |
| 8 | 77.5/80 | 92/92.5 | 1.5/1.5 | 1.5 |
| 9 | 80 | 93.5 | 1.5 | 2.4 |
| 10 | 78 | 94 | 1.5 | 2.5 |
| Residue | | | | 20.9. |

The two compounds were unable to be separated by distillation. The distillation was discontinued and fractions 6–10 were bulked with the residue and treated as follows:

Into a 250 ml one neck round bottom flask equipped with reflux condenser, boiling chips and heating mantle is placed 30 grams of bulked fractions 6–10 and residue of the aforementioned distillation containing the compounds having the structures:

(0.15 moles); 80 ml of anhydrous hexane and 0.3 grams (0.0015 moles) of para-toluene sulfonic acid. With stirring the reaction mass is heated to reflux and refluxed for a period of one hour.

At the end of the one hour reflux period the reaction mass is washed as follows:

(a) one—150 ml portion of water; and
(b) one—50 ml portion of water.

The reaction mass is then concentrated on a rotary evaporator to 27 grams.

At this point in time the reaction mass contains the following products:

(a) the product having the structure:

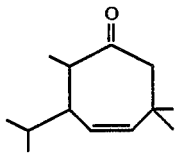

and (b) the product having the structure:

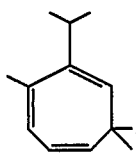

FIG. 7 is the GLC profile of the crude reaction product prior to distillation. The peak indicated by reference numerals 71 is the peak for the compound having the structure:

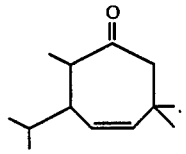

The resulting reaction product is then distilled on a 6" Vigreux column yielding the following fractions:

| Fraction No. | Vapor Temp. (°C.) | Liquid Temp. (°C.) | Vacuum mm/Hg. Pressure | Weight of Fraction (g) |
|---|---|---|---|---|
| 1 | 58 | 81/85 | 1.6 | 1.8 |
| 2 | 58 | 91 | 1.6 | 1.6 |
| 3 | 62 | 95 | 1.7 | 1.0 |
| 4 | 81 | 97 | 1.6 | 1.5 |
| 5 | 82 | 99 | 1.6 | 1.4 |
| 6 | 81.5 | 98.5 | 1.55 | 0.7 |
| 7 | 82 | 100 | 1.65 | 1.4 |
| 8 | 82 | 100/101.5 | 1.7 | 1.4 |
| 9 | 82 | 108 | 1.5 | 2.6 |
| 10 | 79 | 119 | 1.0 | 2.4 |

-continued

| Fraction No. | Vapor Temp. (°C.) | Liquid Temp. (°C.) | Vacuum mm/Hg. Pressure | Weight of Fraction (g) |
|---|---|---|---|---|
| 11 | 79 | 131 | 0.9 | 0.9 |
| 12 | 83 | 148 | 0.7 | 0.8 |

Fractions 5-9 are bulked. Fractions 5-9 as bulked have a woody, rooty, seedy aroma profile with orris-like topnotes.

FIG. 8 is the NMR spectrum for the compound having the structure:

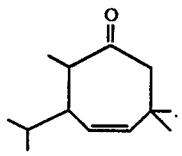

FIG. 9 is the infra-red spectrum for the compound having the structure:

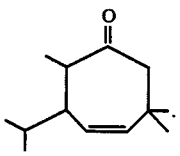

EXAMPLE IV

PREPARATION OF 1,2,6,6-TETRAMETHYL-3-(2'-PROPYL)-4-CYCLOHEPTENE-1-OL IN RECOVERED FORM

Reactions:

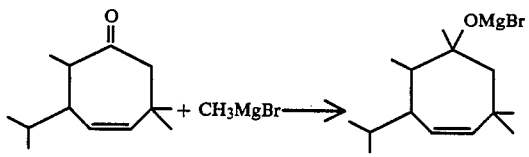

and

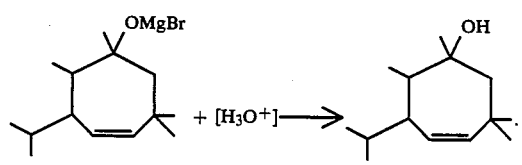

Into a 25 ml Erlenmeyer flask equipped with magnetic stirrer, nitrogen blanket apparatus and cold water bath is placed 2.5 ml of a 2.85 molar solution of methyl magnesium bromide in diethyl ether (0.0072 moles of methyl magnesium bromide) and 3 ml of tetrahydrofuran. The resulting mixture is stirred in a cold water bath.

Over a period of 3 minutes, 1.2 grams of the ketone, bulked fractions 5-9 of the final distillation product of the reaction product of Example III (containing the compound having the structure:

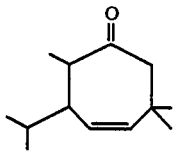

in recovered form) in 1.2 ml of tetrahydrofuran is added to the reaction mass, dropwise with stirring. Thus, 0.006 moles of the compound having the structure:

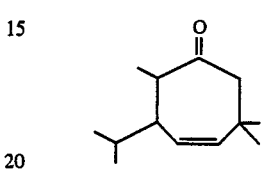

is added to the reaction mass.

The reaction mass is stirred for a period of 0.5 hours. At this point in time the compound having the structure:

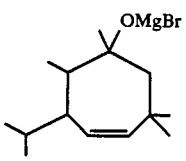

has been prepared.

The resulting reaction mass is cooled. Over a period of 0.5 hours, 10 ml of 15% aqueous acetic acid is added to the reaction mass. Over a period of 0.5 hours, 15 ml of H₂O is added to the reaction mass.

With stirring over a period of 0.5 hours, 10 ml of methylene dichloride is added to the reaction mass. The reaction mass now exists in two phases; an organic phase and an aqueous phase. The organic phase is washed as follows:

(a) 10 ml water;
(b) 10 ml 5% aqueous sodium bicarbonate; and
(c) 10 ml water.

The organic phase is then dried over anhydrous sodium sulfate and concentrated on a rotary evaporator to a weight of 0.7 grams. The organic phase contains geometric isomers of one compound in recovered form, that is, the compound having the structure:

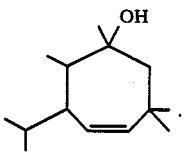

FIG. 10 is the GLC profile of the crude reaction product containing geometric isomers of the compound having the structure:

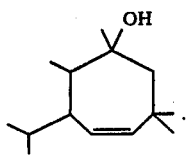

The peak indicated by reference numeral 101 is the peak for one of the geometric isomers of the compound having the structure:

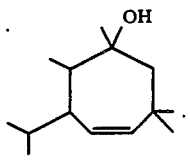

The peak indicated by reference numeral 102 is a peak for another of the geometric isomers of the compound having the structure:

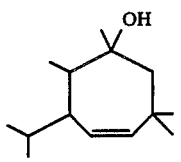

(GLC Conditions: 30 m×0.32 mm supelcowax-10 (carbowax) column programmed at 100°-180° C. at 8° C. per minute).

The resulting product has a woody, fruity, floral (violet) aroma with rose and dried fruit topnotes.

FIG. 11A is the NMR spectrum for the peak indicated by reference numeral 101 of the GLC profile of FIG. 10.

FIG. 11B is the NMR spectrum for the peak indicated by reference numeral 102 of the GLC profile of FIG. 10.

FIG. 12A is the infra-red spectrum for the peak indicated by reference numeral 101 of the GLC profile of FIG. 10.

FIG. 12B is the IR spectrum for the peak indicated by reference numeral 102 of the GLC profile of FIG. 10.

EXAMPLE V

PREPARATION OF 1,5,5-TRIMETHYL-3(2'-PROPYL)CYCLOHEPTA-NONE-1

Reaction:

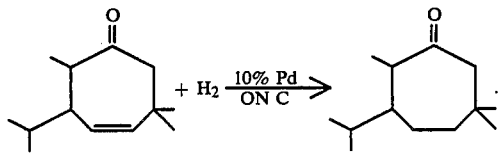

Into a Parr pressure apparatus cooled with a water bath is placed 5 grams (0.026 moles) of bulked fractions 5-9 of Example III (final distillation) consisting essentially of the ketone having the structure:

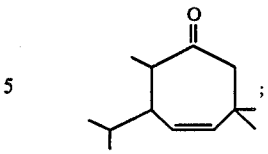

70 ml of isopropyl alcohol and 0.5 grams of a 10% palladium on carbon (dry) catalyst (manufactured by The Degussa S. A. Organizatio). The pressure apparatus is closed and pressurized with hydrogen for a period of 4 hours at a temperature of 20°-23° C. at a pressure 180-205 psig while cooling with a cold water bath.

At the end of the 4 hour period, the pressure is released from the Parr pressure apparatus and the contents are removed and filtered. The contents are then evaporated on a rotary evaporator to a weight of 4.2 grams.

The resulting product contains the compound having the structure:

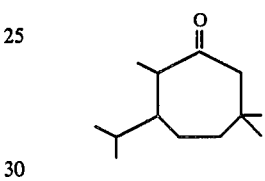

in recovered form. The resulting product has a woody and piney aroma with fruity undertones.

FIG. 13 is the GLC profile for the crude reaction product. (Conditions: 30 m×0.32 mm supelcowax-10 (carbowax) column programmed at 100°-180° C. at 8° C. per minute). The peak indicated by reference numeral 131 is the peak for the compound having the structure:

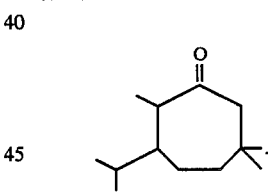

FIG. 14 is the NMR spectrum for the compound having the structure:

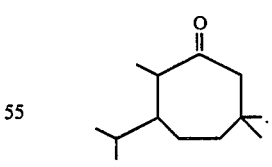

FIG. 15 is the infra-red spectrum for the compound having the structure:

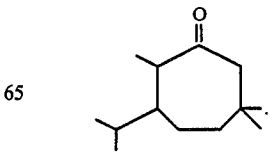

EXAMPLE VI

PREPARATION OF 2,6,6-TRIMETHYL-3-(2'-PROPYL)CYCLOHEPTANOL-1

Reaction:

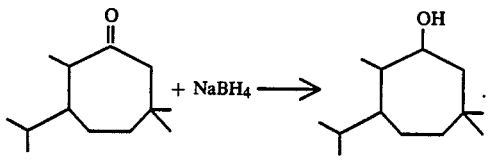

Into a 15 ml three neck flask equipped with magnetic stirrer, thermometer, nitrogen inlet and reflux condenser is placed (under nitrogen flow) 0.10 grams of sodium borohydride (0.00255 moles) in 2 ml of anhydrous ethyl alcohol at a temperature of 23°–24° C. While maintaining the temperature of the reaction mass at 23°–24° C. over a period of 2 minutes, 0.5 grams of the compound having the structure:

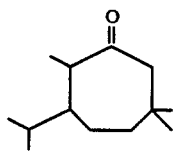

prepared according to Example V (in recovered form) in 0.5 ml of ethyl alcohol (anhydrous) (0.00255 moles of ketone) is added to the reaction mass with stirring. The reaction mass is then stirred for a period of one hour at 23°–24° C.

At the end of the one hour period, the reaction mass is added dropwise to 10 ml of 5% aqueous hydrochloric acid in a cooled (23°–34° C.) 25 ml three neck flask equipped with cooling bath.

The resulting reaction product is extracted with 10 ml of methylene dichloride and the resulting extract is washed with water, followed by dilute aqueous sodium bicarbonate, followed by water. The resulting product is dried on anhydrous sodium sulfate and concentrated on a rotary evaporator to 0.3 grams.

The resulting product consists essentially of geometric isomers of the compound having the structure:

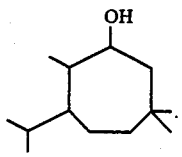

FIG. 16 is the GLC profile of the resulting product containing geometric isomers of the compound having the structure:

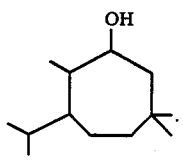

The peak indicated by reference numeral 161 is the peak for one of the geometric isomers of the compound having the structure:

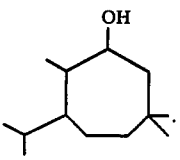

The peak indicated by reference numeral 162 is the peak for another of the geometric isomers of the compound having the structure:

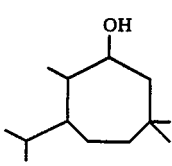

(GLC Conditions: 30 m×0.32 mm supelcowax-10 (carbowax) column programmed at 100°–180° C. at 8° C. per minute).

The mixture of geometric isomers of compounds having the structure:

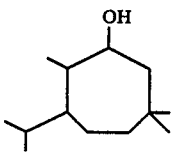

has a woody, fruity, cedarwood aroma profile.

FIG. 17A is the NMR spectrum for the peak indicated by reference numeral 161 on the GLC profile of FIG. 16.

FIG. 17B is the NMR spectrum for the peak indicated by reference numeral 162 on the GLC profile of FIG. 16.

FIG. 18A is the infra-red spectrum for the peak indicated by reference numeral 161 on the GLC profile of FIG. 16.

FIG. 18B is the infra-red spectrum for the peak indicated by reference numeral 162 on the GLC profile of FIG. 16.

EXAMPLE VII

PREPARATION OF 1,2,6,6-TETRAMETHYL-3-(2'-PROPYL)CYCLOHEPTANOL-1

Reactions:

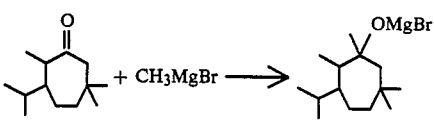

and

-continued

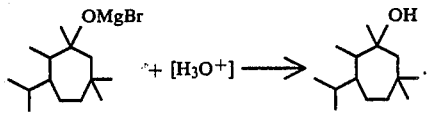

Into a 25 ml Erlenmeyer flask equipped with magnetic stirrer, nitrogen flow apparatus and cold water bath is placed 2.5 ml of a 2.85 molar solution of methyl magnesium bromide in diethyl ether and 3 ml of tetrahydrofuran (0.0072 moles of methyl magnesium bromide). The methyl magnesium bromide solution is stirred and cooled to 15° C. Over a period of 3 minutes 1.2 grams of the ketone having the structure:

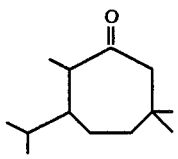

produced according to Example V (0.006 moles) in 1.2 ml tetrahydrofuran is added with stirring to the reaction mass while maintaining the reaction mass at 15° C.

The reaction mass is then stirred for a period of one hour.

At this point in time, the reaction product consists essentially of the compound having the structure:

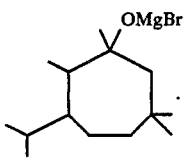

The reaction mixture is slowly added to 15 ml of cooled 15% aqueous acetic acid. The resulting product is then slowly added to 15 ml of cooled water.

The resulting reaction mass is extracted with 15 ml of methylene dichloride.

The reaction mass now exists in two phases; an aqueous phase and an organic phase. The organic phase is washed with water followed by 5% aqueous sodium bicarbonate, followed by water. The resulting product is then dried over anhydrous sodium sulfate and concentrated on a rotary evaporator to a weight of 0.9 grams.

The resulting product is a mixture of geometric isomers of the compound having the structure:

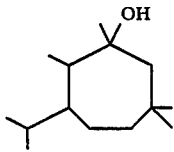

in recovered form.

FIG. 19 is the GLC profile of the crude reaction product containing the compound having the structure:

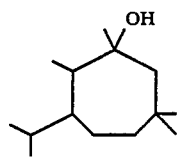

in recovered form (several geometric isomers). (Conditions: 30 m×0.32 mm supelcowax-10 (carbowax) column programmed at 100°-180° C. at 8° C. per minute). The peaks indicated by reference numerals 191 and 192 are peaks for geometric isomers of the compound having the structure:

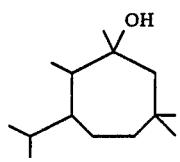

The resulting product has a woody, fruity and camphoraceous aroma.

FIG. 20A is the NMR spectrum for the peak indicated by reference numeral 191 on the GLC profile of FIG. 19.

FIG. 20B is the NMR spectrum for the peak indicated by reference numeral 192 on the GLC profile of FIG. 19.

FIG. 21A is the infra-red spectrum for the peak indicated by reference numeral 191 on the GLC profile of FIG. 19.

FIG. 21B is the infra-red spectrum for the peak indicated by refernce numeral 192 on the GLC profile of FIG. 19.

EXAMPLE VIII

PREPARATION OF 1,3-DI(2'-PROPYL)-2,6,6-TRIMETHYL-CYCLOHEPTANOL-1

Reactions:

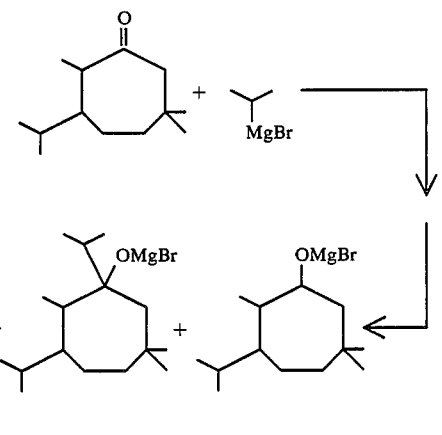

-continued

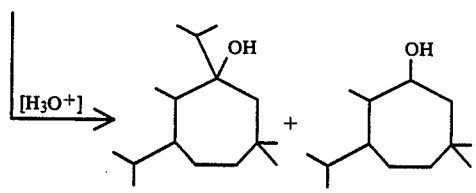

Into a 25 ml three neck flask equipped with magnetic stirrer, thermometer, nitrogen, inlet, reflux condenser and heating mantle is placed 17.4 ml of a 0.7 molar solution of isopropyl magnesium bromide in tetrahydrofuran prepared according to the process of Example III, supra, (0.0122 moles of isopropyl magnesium bromide). While maintaining the reaction mass at 23° C., over a period of 3 minutes, a mixture of 1.0 grams of the ketone of Example V having the structure:

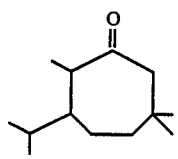

in 1 ml tetrahydrofuran (0.0051 moles) is added, dropwise, to the reaction mass. The reaction mass is then heated to reflux at 68° C. and maintained at reflux for a period of one hour.

The reaction mass at this point in time contains the compound having the structure:

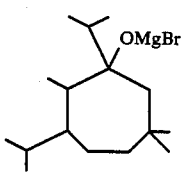

as well as the compound having the structure:

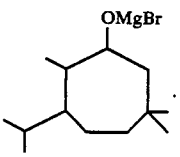

The reaction mass is then gradually added to 15% aqueous acetic acid with cooling.

The resulting mixture is extracted with methylene dichloride and washed with:
(a) water;
(b) 5% aqueous sodium bicarbonate; and
(c) water.

The reaction mass is then concentrated to a weight of 0.35 grams yielding the compounds having the structures:

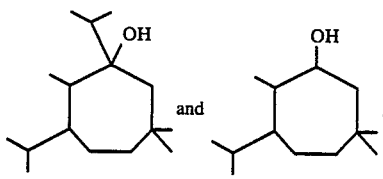

FIG. 22 is the GLC profile for the crude reaction product containing the compounds having the structures:

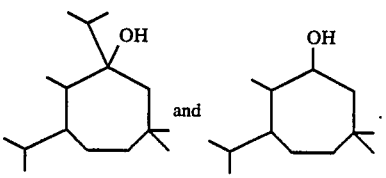

The peak for the product having the structure:

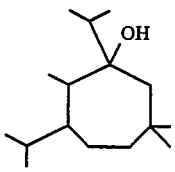

is indicated by the reference numeral 221. (Conditions: 30 m×0.32 mm supelcowax-10 column programmed at 100°-180° C. at 8° C. per minute).

The compound having the structure:

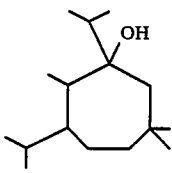

has a fresh, minty aroma.

FIG. 23 is the NMR spectrum for the compound having the structure:

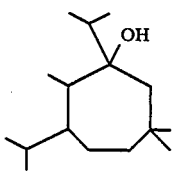

FIG. 24 is the infra-red spectrum for the compound having the structure:

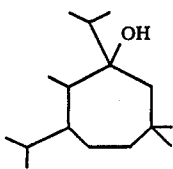

EXAMPLE IX

PREPARATION OF 2,6,6-TRIMETHYL-CYCLOHEPTANONE-1

Reaction:

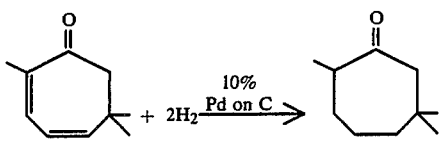

Into a Parr pressure apparatus equipped with cooling water and a cold water bath and equipped for pressurization using hydrogen is placed 50 grams (0.333 moles) of eucarvone (bulked fractions 6-11 of Example A) having the structure:

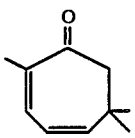

100 ml isopropyl alcohol and 0.6 grams of 10% palladium-on-carbon catalyst produced by Degussa S. A.

The Parr pressure apparatus is closed (sealed) and pressurized with hydrogen at a temperature of 20°-32° C. at a pressure of 150-210 psig for a period of 1.5 hours. At the end of the 1.5 hour period, the apparatus is opened (depressurized) and cooled to room temperature.

The reaction mass is filtered and the filtrate is concentrated to a weight of 46.4 grams.

At this point in time, the reaction mass consists essentially of the compound having the structure:

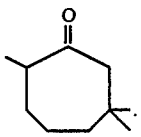

FIG. 25 is the GLC profile for the crude reaction product (Conditions: 30 m×0.32 mm supelcowax-10 column programmed at 100°-180° C. at 8° C. per minute).

The peak indicated by reference numeral 251 is the peak for the compound having the structure:

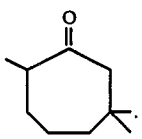

FIG. 26 is the NMR spectrum for the compound having the structure:

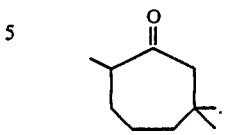

FIG. 27 is the IR spectrum for the compound having the structure:

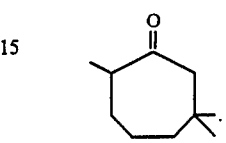

The compound having the structure:

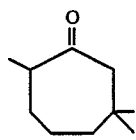

has a minty (peppermint) and herbaceous aroma with pennyroyal-like topnotes.

EXAMPLE X

PREPARATION OF 2,6,6-TRIMETHYL-CYCLOHEPTANOL

Reaction:

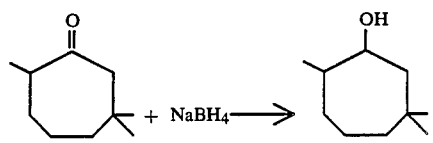

Into a 25 ml three neck flask equipped with magnetic stirrer, reflux condenser, nitrogen inlet and thermometer is placed 0.25 grams of sodium borohydride (0.0065 moles) and 3 ml of anhydrous ethyl alcohol. Over a period of 3 minutes, the ketone having the structure:

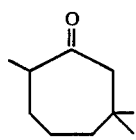

produced according to Example IX is added to the reaction mass (in admixture with anhydrous ethyl alcohol) (1 gram ketone and 1 ml anhydrous ethyl alcohol) (moles ketone: 0.0065 moles).

The reaction mass is then stirred for a period of 1 hour. At the end of the 1 hour period, the reaction mass is admixed with 100 ml of 5% hydrochloric acid (aqueous) in a 50 ml three neck flask. The resulting reaction product is stirred for a period of 1 hour. The reaction mass is then extracted with methylene dichloride and washed with water, dilute sodium bicarbonate and then water.

The resulting product is concentrated in an evaporator to a weight of 0.6 grams.

The resulting product, having the structure:

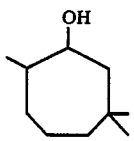

has a dried fruit (figs, dates) tobacco-like, minty, camphoraceous and earthy aroma with ionone-like undertones.

FIG. 28 is the GLC profile for the reaction product containing geometric isomers of the compound having the structure:

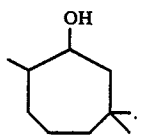

The peaks indicated by reference numerals 281 and 282 are peaks for the geometric isomers of the compound having the structure:

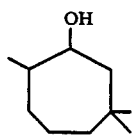

(Conditions: 30 m×0.32 mm supelcowax-10 (carbowax) column programmed at 100°-180° C. at 8° C. per minute).

FIG. 29A is the NMR spectrum for one of the geometric isomers of the compound having the structure:

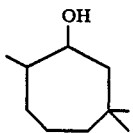

as indicated by the peak 281 on the GLC profile of FIG. 28.

FIG. 29B is the NMR spectrum for the peak indicated by reference numeral 282 in FIG. 28.

FIG. 30A is the infra-red spectrum for the peak indicated by reference numeral 281 in FIG. 28.

FIG. 30B is the infra-red spectrum for the peak indicated by reference numeral 282 in FIG. 28.

EXAMPLE XI

PREPARATION OF 1,2,6,6-TETRAMETHYL-CYCLOHEPTANOL-1

Reactions:

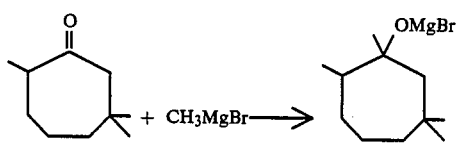

and

-continued

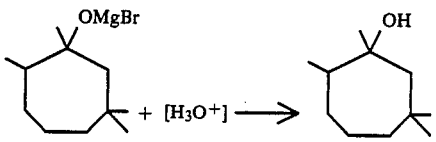

Into a 25 ml Erlenmeyer flask equipped with magnetic stirrer, nitrogen inlet tube and cold water bath is placed a solution of 2.85 molar methyl magnesium bromide in diethyl ether (2.7 ml) in 3 ml tetrahydrofuran (0.0078 moles of methyl magnesium bromide).

To the methyl magnesium bromide solution with cooling over a period of 20 minutes is placed 1.0 grams of the ketone having the structure:

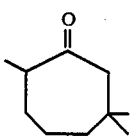

prepared according to Example IX in 1 ml tetrahydrofuran.

The reaction mass now consists essentially of the compound having the structure:

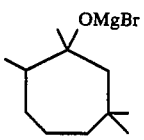

in solution.

The reaction mass is then added to 20 ml dilute acetic acid (aqueous) with cooling. The resulting reaction product is then extracted with methylene dichloride and the methylene dichloride extract is washed with water, followed by 15% sodium bicarbonate solution followed by water. The resulting product is dried over anhydrous sodium sulfate and concentrated to 0.8 grams.

The reaction product now consists essentially of geometric isomers of the compound having the structure:

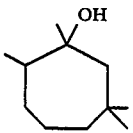

including the isomers having the structures:

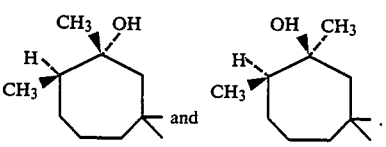

The product has a patchouli-like, earthy, rooty and camphoraceous aroma profile.

FIG. 31 is the GLC profile for the crude reaction product containing the compound having the structure:

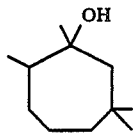

(Conditions: 30 m×0.32 mm supelcowax-10 (carbowax) column programmed at 100°–180° C. at 8° C. per minute). The peaks indicated by reference numerals 311 and 312 are peaks for the geometric isomers of the compound having the structure:

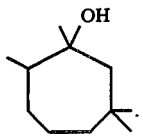

FIG. 32 is the NMR spectrum for the peak indicated by reference numeral 311, a geometric isomer of the compound having the structure:

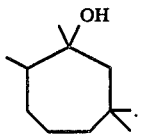

FIG. 33 is the infra-red spectrum for the peak indicated by reference numeral 311, a geometric isomer of the compound having the structure:

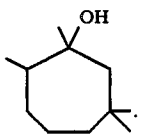

EXAMPLE XII

PREPARATION OF 1-(2'METHYL-1'PROPYL)-2,6,6-TRIMETHYL-CYCLOHEPTANOL-1

Reactions:

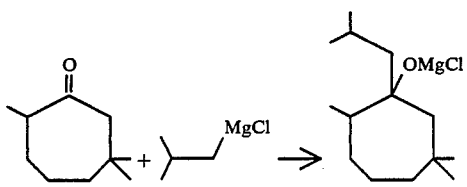

and

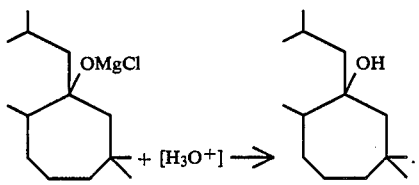

Into a 25 ml Erlenmeyer flask equipped with magnetic stirrer, nitrogen inlet tube and cold water bath is placed a 2 molar solution of isobutyl magnesium chloride in diethyl ether (3.9 ml)(0.0078 moles of isobutyl magnesium chloride) and 4 ml of tetrahydrofuran. With cooling over a period of 7 minutes, the ketone having the structure:

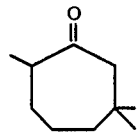

prepared according to Example IX (1.0 grams; 0.0065 moles) in (1 ml tetrahydrofuran) is added to the reaction mass.

At this point in time the reaction mass consists essentially of the compound having the structure:

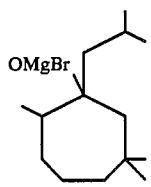

in solution.

The reaction mass is then added to 25 ml of 15% aqueous acetic acid. The reaction mass is then extracted with methylene dichloride and washed with water, followed by saturated sodium bicarbonate, followed by additional water. The reaction mass is then evaporated to a weight of 0.8 grams.

The reaction mass at this point in time consists essentially of the compound having the structure:

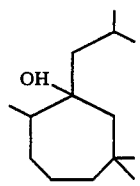

(mixture of geometric isomers).

The reaction product having the structure:

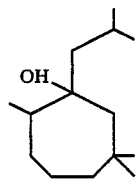

(mixture of geometric isomers) has a woody, camphoraceous aroma with a fruity topnote.

FIG. 34 is the GLC profile for the crude reaction product (Conditions: 30 m×0.32 mm supelcowax-10 (carbowax) column programmed at 100°–180° C. at 8° C. per minute). The peak indicated by reference numeral 341 is a peak for a geometric isomer of the compound having the structure:

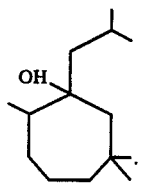

FIG. 35 is the NMR spectrum for the compound having the structure:

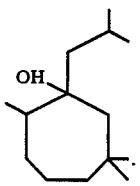

FIG. 36 is the infra-red spectrum for the compound having the structure:

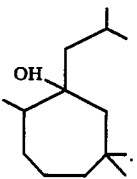

EXAMPLE XIII

PRECIOUS WOODY FRAGRANCE

The following precious woody fragrance formulations are prepared:

| Ingredients | Parts by Weight | | | | |
|---|---|---|---|---|---|
| | (A) | (B) | (C) | (D) | (E) |
| 2,5,5-Trimethyl Cycloheptane prepared by the process of Example I of U.S. Letters Pat. No. 3,869,411 | 50 | 50 | 50 | 50 | 50 |
| 6,7-Dihydro-1,1,2,3,3-Pentamethyl-4-(5H)Indanone Produced according to Preparation A of Swiss Patent 523,962 | 5 | 5 | 5 | 5 | 5 |
| Cedrol Methyl Ether having the structure: | 15 | 15 | 15 | 15 | 15 |
| [structure with O—CH₃] | 15 | 15 | 15 | 15 | 15 |
| Vertofix Coeur (Reaction product of Acetic Anhydride and Polyphosphoric acid with American Cedarwood Oil (Runeberg, Acta. Chem. Scand-15,592 (1961) | 15 | 15 | 15 | 15 | 15 |
| 1,3,4,6,7,8-Hexahydro-4,6,6,7,8,8-Hexamethyl Cyclopenta-gamma-2-benzopyran | 5 | 5 | 5 | 5 | 5 |

-continued

| Ingredients | Parts by Weight | | | | |
|---|---|---|---|---|---|
| | (A) | (B) | (C) | (D) | (E) |
| Grisalva (Produced by the 50% sulfuric acid treatment of 3-Ethyl-1[2,2,6-Trimethyl Cyclohexene-5-yl-1] hexen-3-ol-6) | 3 | 3 | 3 | 3 | 3 |
| Cedrenal having the structure: [structure] | 10 | 10 | 10 | 10 | 10 |
| Mixture containing primarily Methyl-2,6,10-Trimethyl-2,5,9-dodecatrien-1-yl-Ketone, produced according to the process of Example I of Canadian Patent 864,592 | 5 | 5 | 5 | 5 | 5 |
| Sandalwood E.I. | 10 | 10 | 10 | 10 | 10 |
| 8,9 Epoxy Cedrane | 10 | 10 | 10 | 10 | 10 |
| Mixture of alcohols produced according to Example II having the structures: [two OH structures] | 50 | 0 | 0 | 0 | 0 |
| Compound having the structure: [ketone structure] produced according to Example III. | 0 | 50 | 0 | 0 | 0 |
| Compound having the structure: [OH structure] produced according to Example X. | 0 | 0 | 50 | 0 | 0 |
| Compound having the structure: [OH structure] | 0 | 0 | 0 | 50 | 0 |

-continued

| Ingredients | Parts by Weight | | | | |
|---|---|---|---|---|---|
| | (A) | (B) | (C) | (D) | (E) |
| produced according to Example XI. | | | | | |
| Compound having the structure: | 0 | 0 | 0 | 0 | 50 |

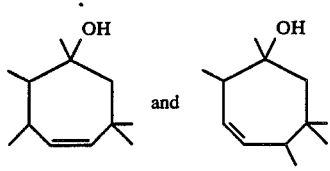

produced according to Example XII.

Addition of the mixture of compounds having the structures:

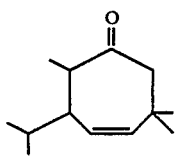

imparts to this precious woody formulation earthy, camphoraceous, sweaty, animalic, woody and patchouli-like undertones. Accordingly, the formulation of Example XIII(A) can be described as "precious woody with earthy, camphoraceous, sweaty, animalic, woody and patchouli-like undertones".

Addition of the compound having the structure:

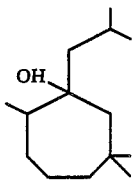

imparts to this precious woody formulation imparts to the precious woody formulation woody, rooty and seedy undertones and orris-like topnotes. Accordingly, the formulation of Example XIII(B) can be described as "precious woody with woody, rooty and seedy undertones and orris-like topnotes".

Addition of the compound having the structure:

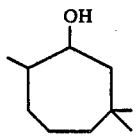

to this precious woody formulation imparts to it dried fruit, tobacco-like, minty, camphoraceous, earthy and ionone-like undertones. Accordingly, the formulation of Example XIII(C) can be described as "precious woody with dried fruit, tobacco-like, minty, camphoraceous, earthy and ionone-like undertones".

Addition of the compound having the structure:

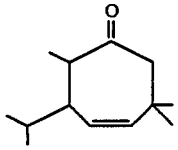

produced according to Example III imparts to this precious woody formulation patchouli-like, earthy, rooty and camphoraceous undertones. Accordingly, the formulation of Example XIII(D) can be described "precious woody with patchouli-like, earthy, rooty and camphoraceous undertones".

Addition of the compound having the structure:

imparts to this precious woody formulation camphoraceous undertones and fruity topnotes. Accordingly, the formulation of Example XIII(E) can be described as "precious woody with camphoraceous undertones and fruity topnotes".

EXAMPLE XIV

PINE FRAGRANCE

The following pine fragrance formulations are prepared:

| Ingredients | Parts by Weight | | |
|---|---|---|---|
| | XIV(A) | XIV(B) | XIV(C) |
| Isobornyl acetate | 100 | 100 | 100 |
| Camphor | 10 | 10 | 10 |
| Terpineol | 25 | 25 | 25 |
| Fir balsam absolute (50% in diethyl phthalate) | 20 | 20 | 20 |
| Coumarin | 4 | 4 | 4 |
| Linalool | 30 | 3 | 30 |
| Frenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-trimethyl-1-cyclohexene-1-carboxaldehyde | 12 | 12 | 12 |
| Maltol (1% in diethyl phthalate) | 5 | 5 | 5 |
| Compound having the structure: | 28 | 0 | 0 | produced according to Example V.

| Compound having the structure: | 0 | 28 | 0 |

-continued

| Ingredients | Parts by Weight | | |
|---|---|---|---|
| | XIV(A) | XIV(B) | XIV(C) |
| Compound having the structure: 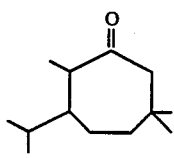 produced according to Example VI. | | | |
| Compound having the structure: 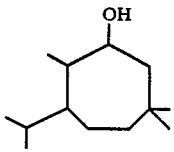 produced according to Example VII. | 0 | 0 | 28 |

The compound having the structure:

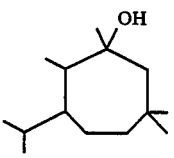

produced according to Example V imparts to this piney formulation woody and fruity undertones. Accordingly, the formulation of Example XIV(A) can be described as "piney with woody and fruity undertones".

Addition of the compound having the structure:

produced according to Example VI imparts to this piney formulation fruity and cedarwood undertones. Accordingly, the formulation of Example XIV(B) can be described as "piney with fruity and cedarwood undertones".

Addition of the compound having the structure:

produced according to Example VII imparts to this piney formulation fruity and camphoraceous undertones. Accordingly, the formulation of Example XIV(C) can be described as "piney with fruity and camphoraceous undertones".

EXAMPLE XV

FLORAL PERFUME COMPOSITIONS

The following floral fragrance is prepared:

| Ingredients | Parts by Weight | | | |
|---|---|---|---|---|
| | XIV(A) | XIV(B) | XIV(C) | XIV(D) |
| Citronellol | 12.3 | 12.3 | 12.3 | 12.3 |
| Geraniol | 2.5 | 2.5 | 2.5 | 2.5 |
| Amyl Cinnamic Aldehyde | 24.6 | 24.6 | 24.6 | 24.6 |
| Galaxolide ® 50 (Trademark Tricyclic Isochroman of International Flavors & Fragrances Inc.) | 9.8 | 9.8 | 9.8 | 9.8 |
| Vertenex High Cis (Cis-t-Butylcyclohexenyl Acetate; Para Isomer) | 7.4 | 7.4 | 7.4 | 7.4 |
| Rose Oxide | 0.7 | 0.7 | 0.7 | 0.7 |
| Cinnamic Alcohol | 19.6 | 19.6 | 19.6 | 19.6 |
| Aldehyde C-11 (n-Undecylenic Aldehyde | 0.5 | 0.5 | 0.5 | 0.5 |
| Aldehyde C-12 (n-Dodecyl Aldehyde in 10% solution in diethyl phthalate) | 0.5 | 0.5 | 0.5 | 0.5 |
| Citronellal (10% solution in diethyl phthalate) | 0.5 | 0.5 | 0.5 | 0.5 |
| Phenyl Ethyl Acetate | 2.5 | 2.5 | 2.5 | 2.5 |
| Ylang Oil | 1.2 | 1.2 | 1.2 | 1.2 |
| Indisan (Hydrogenated derivative of reaction product of Camphene and Resorcinol | 3.7 | 3.7 | 3.7 | 3.7 |
| Musk Ketone | 5.0 | 5.0 | 5.0 | 5.0 |
| Oakmoss Resin | 0.5 | 0.5 | 0.5 | 0.5 |
| Liatrix Absolute (10% in diethyl phthalate | 2.5 | 2.5 | 2.5 | 2.5 |
| Vetiver Acetate | 1.2 | 1.2 | 1.2 | 1.2 |
| Diethyl Phthalate | 5.0 | 5.0 | 5.0 | 5.0 |
| Mixture of Compounds having the structures: and produced according to Example I. | 5.0 | 0.0 | 0.0 | 0.0 |
| Compound having the structure: | 0.0 | 5.0 | 0.0 | 0.0 |

-continued

| Ingredients | Parts by Weight | | | |
|---|---|---|---|---|
| | XIV(A) | XIV(B) | XIV(C) | XIV(D) |
| 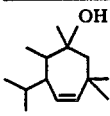 produced according to Example IV. | | | | |
| Compound having the structure 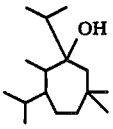 produced according to Example VIII. | 0.0 | 0.0 | 5.0 | 0.0 |
| Compound having the structure:  produced according to Example IX. | 0.0 | 0.0 | 0.0 | 5.0 |

The mixture of compounds having the structures:

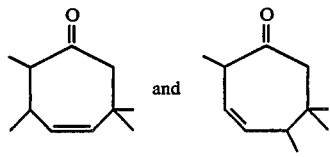

produced according to Example I imparts to this floral fragrance fruity and minty undertones with dried fruit and rose topnotes. Accordingly, this floral fragrance can be described as "floral with fruity (apple) and minty undertones and dried fruit and rose topnotes".

Addition of the compound having the structure:

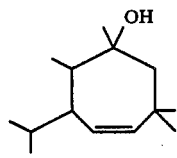

produced according to Example IV to this floral fragrance imparts thereto woody and fruity undertones with rose and dried fruit topnotes. Accordingly, the fragrance of Example XV(B) can be described as "floral with woody and fruity undertones and rose and dried fruit topnotes.

Addition of the compound having the structure:

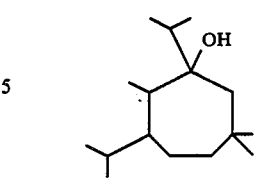

produced according to Example VIII imparts to the floral formulation of Example XV(C) fresh and minty undertones. Accordingly, the floral fragrance of Example XV(C) can be described as "floral with fresh and minty undertones".

Addition of the compound having the structure:

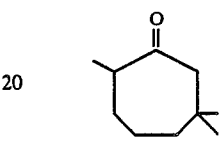

produced according to Example IX to the floral fragrance of Example XV(D) imparts to this floral fragrance peppermint and herbaceous undertones and pennyroyal-like topnotes. Accordingly, the floral formulation of Example XV(D) can be described as "floral with peppermint and herbaceous undertones and pennyroyal-like topnotes".

EXAMPLE XVI

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| SUBSTANCE | AROMA DESCRIPTION |
|---|---|
| Mixture of compounds having the structures: 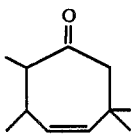 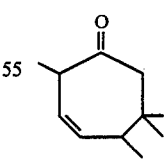 and | A fruity (apple) minty aroma profile with dried fruit and rose topnotes. |
| Mixture of compounds having the structures: 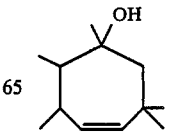 and | An earthy, camphoraceous, sweaty, animalic, woody and patchouli-like aroma profile. |

TABLE II-continued

| SUBSTANCE | AROMA DESCRIPTION |
|---|---|
| 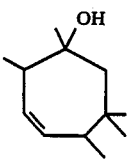<br>produced according to Example II. | |
| Compound having the structure:<br>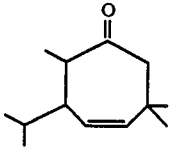<br>produced according the Example III. | A woody, rooty and seedy aroma with orris-like topnotes. |
| Compound having the structure:<br>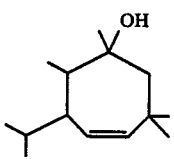<br>produced according to Example IV. | A woody, fruity, floral (violet) aroma profile with rose and dried fruit topnotes. |
| Compound having the structure:<br>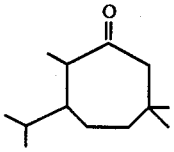<br>produced according to Example V. | A woody and piney aroma with fruity undertones. |
| Compound having the structure:<br>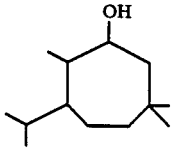<br>produced according to Example VI. | A woody, fruity and cedarwood aroma profile. |
| Compound having the structure:<br>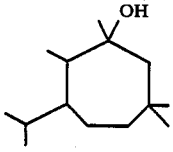 | A woody, fruity and camphoraceous aroma profile. |

TABLE II-continued

| SUBSTANCE | AROMA DESCRIPTION |
|---|---|
| produced according to Example VII. | |
| Compound having the structure:<br>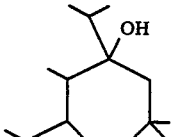<br>produced according to Example VIII. | A fresh and minty aroma. |
| Compound having the structure:<br>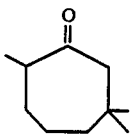<br>produced according to Example IX. | A minty (peppermint) and herbaceous aroma profile with Pennyroyal-like topnotes. |
| Compound having the structure:<br>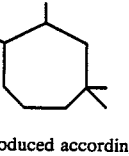<br>produced according to Example X. | A dried fruit (figs and dates), tobacco-like, minty, camphoraceous and earthy aroma profile with ionone-like undertones. |
| Compound having the structure:<br>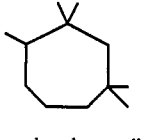<br>produced according to Example XI. | A patchouli-like, earthy, rooty and camphoraceous aroma profile. |
| Compound having the structure:<br>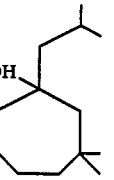<br>produced according to Example XII. | A rooty and camphoraceous aroma with fruity topnotes. |
| Perfume formulation of Example XIII(A). | Precious woody with earthy, camphoraceous, sweaty, animalic, woody and patchouli-like undertones. |
| Perfume formulation | Precious woody with woody, rooty |

TABLE II-continued

| SUBSTANCE | AROMA DESCRIPTION |
| --- | --- |
| of Example XIII(B). | and seedy undertones and orris-like topnotes. |
| Perfume formulation of Example XIII(C). | Precious woody with dried fruit, totacco-like, minty, camphoraceous, earthy and ionone-like undertones. |
| Perfume formulation of Example XIII(D). | Precious woody with patchouli-like, earthy, rooty and camphoraceous undertones. |
| Perfume formulation of Example XIII(E). | Precious woody with camphoraceous undertones and fruity topnotes. |
| Perfume formulation of Example XIV(A). | Piney with woody and fruity undertones. |
| Perfume formulation of Example XIV(B). | Piney with fruity and cedarwood undertones. |
| Perfume formulation of Example XIV(C). | Piney with fruity and camphoraceous undertones. |
| Perfume composition of Example XV(A). | Floral with fruity (apple) and minty undertones and dried fruit and rose topnotes. |
| Perfume composition of Example XV(B). | Floral with woody and fruity undertones and rose and dried fruit topnotes. |
| Perfume composition of Example XV(C). | Floral with fresh and minty undertones. |
| Perfume composition of Example XV(D). | Floral with peppermint and herbaceous undertones and pennyroyal-like topnotes. |

EXAMPLE XVII

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example XVI are prepared containing 0.10%, 0.15%, 0.20%, 0.25%, 0.30% and 0.35% of the substance set forth in Table II of Example XVI. They are prepared by adding and homogeneously mixing the appropriate quantity of substance set forth in Table II of Example XVI in the liquid detergent. The detergents all possess excellent aromas as set forth in Table II of Example XVI, the intensity increasing with greater concentrations of substances as set forth in Table II of Example XVI.

EXAMPLE XVIII

PREPARATION OF COLOGNES AND HANDKERCHIEF PERFUMES

Compositions as set forth in Table II of Example XVI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XVI are imparted to the colognes and to the handkerchief perfumes at all levels indicated.

EXAMPLE XIX

PREPARATION OF SOAP COMPOSITION

One hundred grams of soap chips (per sample)-(IVORY ®, produced by the Procter & Gamble Company of Cincinnati, Ohio), are each mixed with one gram sample of substances as set forth in Table II of Example XVI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example XVI.

EXAMPLE XX

PREPARATION OF SOLID DETERGENT COMPOSITIONS

Detergents are prepared using the following ingredients according to Example I of Canadian Pat. No. 1,007,948 (incorporated herein by reference):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example XVI. Each of the detergent samples has an excellent aroma as indicated in Table II of Example XVI.

EXAMPLE XXI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table II of Example XVI.

Fabric softening compositions prepared according to Example I at column 15 of U.S. Pat. No. 3,632,396 having aroma characteristics as set forth in Table II of Example XVI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XVI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example XVI, supra.

EXAMPLE XXII

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

|  | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example XVI, supra | 0.10 |

The perfume substances are set forth in Table II of Example XVI add aroma characteristics as set forth in Table II of Example XVI which are rather intense and aesthetically pleasing to the users of the soft-feel, good-hold pump hair sprays.

EXAMPLE XXIII

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol disterate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ® 755N polymer (manufactured by GAF Corporation of 140 West 51st Street, New York, N.Y.)(5.0 weight percent) is admixed with 0.1 weight percent sodium sulfite and 1.4 weight percent polyethylene glycol 6000 disterate produced by Armak Corporation. This material is "COMPOSITION B"

The resulting "COMPOSITION A" and "COMPOSITION B" are then mixed in a 50:50 wt ratio of A:B and cooled to 45° C. and 0.3 wt percent of perfuming substance as set forth in Table II of Example XVI is added to the mixture. The resulting mixture is cooled to 40° C. and blending is carried out for an additional one hour in each case. At the end of this blending period, the resulting material has a pleasant fragrance as indicated in Table II of Example XVI.

What is claimed is:

1. A mixture of compounds having the structures:

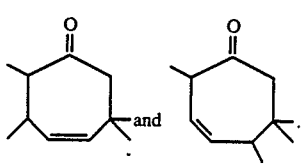

2. A mixture of compounds having the structures:

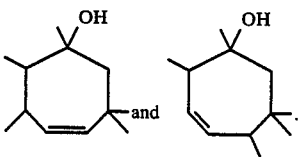

3. A compound having the structure:

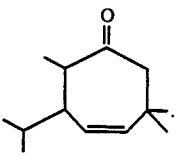

4. A compound having the structure:

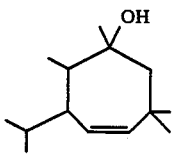

5. A compound having the structure:

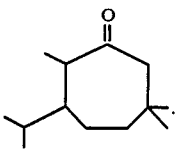

6. A compound having the structure:

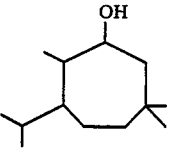

7. A compound having the structure:

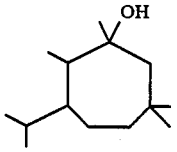

8. A compound having the structure:

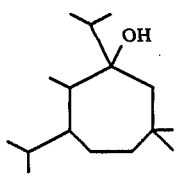

9. A compound having the structure:

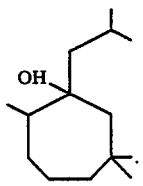

10. A compound defined according to the generic structure:

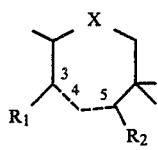

wherein X represents the moiety:

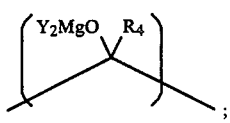

wherein one of the dashed lines is a carbon-carbon double bond and the other of the dashed lines is a carbon-carbon single bond or both dashed lines are carbon-carbon single bonds; wherein $R_1$ and $R_2$ each represent H or lower alkyl; wherein $R_4$ represents lower alkyl; wherein Y represents chloro or bromo; with the proviso that when the dashed line at the 4–5 position is a double bond then $R_2$ is hydrogen and when the dashed line at the 3–4 position is a double bond, $R_1$ is hydrogen.

11. A process for augmenting or enhancing the aroma of a perfume composition, perfumed article or cologne comprising the step of admixing with a perfume base, a perfumed article base or a cologne base, an aroma augmenting or enhancing quantity of at least one polyalkyl-substituted oxocycloheptane derivative composition selected from the group consisting of:

(i) a mixture of compounds having the structures:

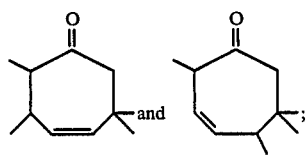

(ii) a mixture of compounds having the structures:

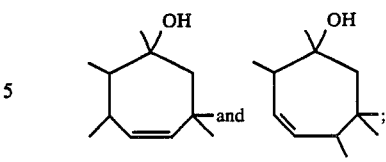

(iii) the compound having the structure:

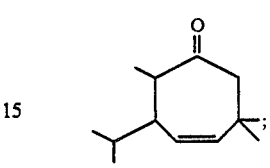

(iv) the compound having the structure:

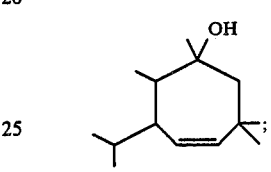

(v) the compound having the structure:

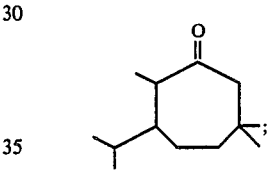

(vi) the compound having the structure:

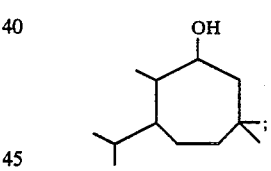

(vii) the compound having the structure:

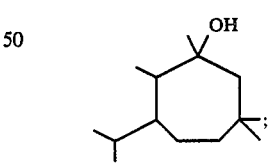

(viii) the compound having the structure:

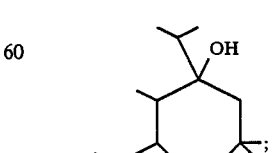

and
(ix) the compound having the structure:

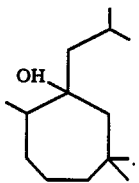

12. The process of claim 11 wherein the polyalkyl-substituted oxocycloheptane derivative augments a perfume composition.

13. The process of claim 11 wherein the polyalkyl-substituted oxocycloheptane derivative augments a perfumed article and the perfumed article is a solid or liquid anionic, cationic, nonionic or zwitterionic detergent.

14. The process of claim 11 wherein the polyalkyl-substituted oxocycloheptane derivative augments the aroma of a perfumed article and the perfumed article is a fabric softener article or fabric softener composition.

15. The process of claim 11 wherein the polyalkyl-substituted oxocycloheptane derivative augments the aroma of a perfumed article and the perfumed article is a perfumed polymer.

* * * * *